United States Patent

Peschke et al.

[11] Patent Number: 5,922,770
[45] Date of Patent: Jul. 13, 1999

[54] COMPOUNDS WITH GROWTH HORMONE RELEASING PROPERTIES

[75] Inventors: Bernd Peschke, Måløv; Michael Ankersen, Frederiksberg; Thomas Kruse Hansen, Herlev; Henning Thøgersen, Farum, all of Denmark

[73] Assignee: Novo Nordisk A/S, Bagsvaerd, Denmark

[21] Appl. No.: 08/896,550

[22] Filed: Jul. 17, 1997

[30] Foreign Application Priority Data

Jul. 22, 1996 [DK] Denmark ................................ 0803/96

[51] Int. Cl.$^6$ ...................... A61K 31/165; C07C 233/11; C07C 235/34; C07C 237/22
[52] U.S. Cl. .................... 514/619; 514/255; 514/307; 514/319; 514/400; 514/419; 514/428; 514/438; 514/443; 544/400; 546/146; 546/205; 548/338.1; 548/495; 548/567; 548/568; 549/58; 549/76; 564/157
[58] Field of Search ............................ 546/205; 514/319, 514/619; 564/157

[56] References Cited

FOREIGN PATENT DOCUMENTS

WO 95/17423 A1 6/1995 WIPO .
WO 96/22997 A1 8/1996 WIPO .
WO 97/23508 A1 7/1997 WIPO .

*Primary Examiner*—Johann Richter
*Assistant Examiner*—Jane C. Osvecki
*Attorney, Agent, or Firm*—Steve T. Zelson; Valeta Gregg; Carol E. Rozek

[57] ABSTRACT

Novel peptide derivatives, compositions containing them, and their use for treating medical disorders resulting from a deficiency in growth hormone are disclosed. The peptides have the formula (I):

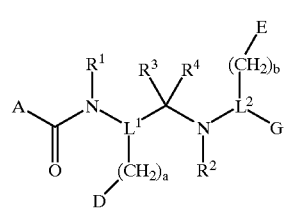

wherein a, b, A, $R^1$, $L^1$, D, $R^3$, $R^4$, $R^2$, $L^2$, E and G are as defined in the specification. These peptides exhibit improved resistance to proteolytic degradation, and hence, improved bioavailability.

16 Claims, No Drawings

COMPOUNDS WITH GROWTH HORMONE RELEASING PROPERTIES

CROSS-REFERENCE TO RELATED APPLICATIONS

This application claims priority under 35 U.S.C. 119 of Danish application Ser. No. 0803/96 filed Jul. 22, 1996, the contents of which are fully incorporated herein by reference.

FIELD OF INVENTION

The present invention relates to novel compounds, pharmaceutical compositions containing them, a method of stimulating the release of growth hormone from the pituitary, a method for increasing the rate and extent of growth of animals to increase their milk and wool production, or for the treatment of ailments, and to use of the compounds for the preparation of medicaments.

BACKGROUND OF THE INVENTION

Growth hormone is a hormone which stimulates growth of all tissues capable of growing. In addition, growth hormone is known to have a number of effects on metabolic processes, e.g., stimulation of protein synthesis and free fatty acid mobilization and to cause a switch in energy metabolism from carbohydrate to fatty acid metabolism. Deficiency in growth hormone can result in a number of severe medical disorders, e.g., dwarfism.

Growth hormone is released from the pituitary. The release is under tight control of a number of hormones and neurotransmitters either directly or indirectly. Growth hormone release can be stimulated by growth hormone releasing hormone (GHRH) and inhibited by somatostatin. In both cases the hormones are released from the hypothalamus but their action is mediated primarily via specific receptors located in the pituitary. Other compounds which stimulate the release of growth hormone from the pituitary have also been described. For example arginine, L-3,4-dihydroxyphenylalanine (L-Dopa), glucagon, vasopressin, PACAP (pituitary adenylyl cyclase activating peptide), muscarinic receptor agonists and a synthethic hexapeptide, GHRP (growth hormone releasing peptide) release endogenous growth hormone either by a direct effect on the pituitary or by affecting the release of GHRH and/or somatostatin from the hypothalamus.

In disorders or conditions where increased levels of growth hormone is desired, the protein nature of growth hormone makes anything but parenteral administration nonviable. Furthermore, other directly acting natural secretagogues, e.g., GHRH and PACAP, are longer polypeptides for which reason oral administration of them is not viable.

The use of certain compounds for increasing the levels of growth hormone in mammals has previously been proposed, e.g. in EP 18 072, EP 83 864, WO 89/07110, WO 89/01711, WO 89/10933, WO 88/9780, WO 83/02272, WO 91/18016, WO 92/01711, WO 93/04081, WO 95/17422, WO 95/17423, WO 95/14666, WO 96/15148 and WO 96/10040.

The composition of growth hormone releasing compounds is important for their growth hormone releasing potency as well as their bioavailability. It is therefore an object of the present invention to provide novel compounds with growth hormone releasing properties.

SUMMARY OF INVENTION

Accordingly, the present invention relates to a compound of the general formula I

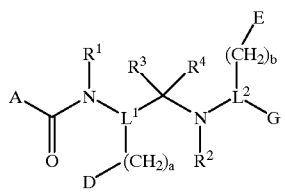

formula I wherein
A is $A^1$ or $A^2$;
G is $G^1$ or $G^2$;
D is hydrogen, $—O—(CH_2)_k—R^{5a}$,

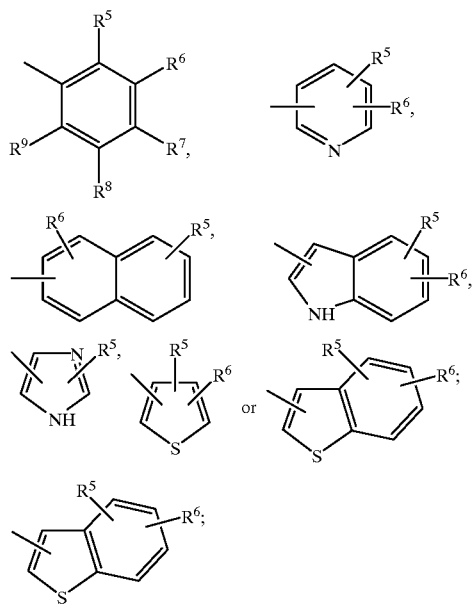

wherein $R^5$, $R^6$, $R^7$, $R^8$, and $R^9$ independently are hydrogen, halogen, aryl, $C_{1-6}$-alkyl or $C_{1-6}$-alkoxy;
$R^{5a}$ is hydrogen, aryl optionally substituted with halogen or $C_{1-6}$-alkyl, or $C_{1-6}$-alkyl optionally substituted with halogen or $C_{1-6}$-alkyl, k is 0, 1, 2, or 3;
E is hydrogen, $—O—(CH_2)_l—R^{10a}$,

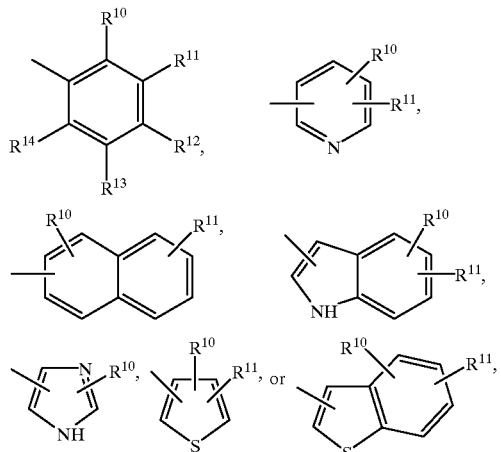

-continued

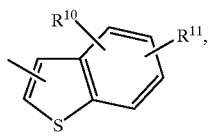

wherein $R^{10}$, $R^{11}$, $R^{12}$, $R^{13}$ and $R^{14}$ independently are hydrogen, halogen, aryl, $C_{1-6}$-alky, $C_{1-6}$-alkoxy, —$CONR^{15}R^{16}$, —$(CH_2)_v$—$NR^{15}SO_2R^{17}$, —$(CH_2)_v$—$NR^{15}COR^{16}$, —$(CH_2)_v$—$OR^{17}$, —$(CH_2)_v$—$OR^{17}$, —$(CH_2)_{v-OCOR}{}^{16}$, —$CH(R^{15})R^{16}$, —$(CH_2)_v$—$NR^{15}$—$CS$—$NR^{16}R^{18}$, —$(CH_2)_v$—$NR^{15}$—$CO$—$NR^{16}R^{18}$,

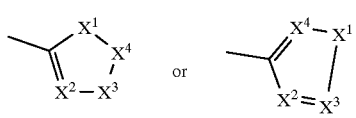

wherein $X^1$ is —$N(R^{19})$—, —O— or —S—, $X^2$ is —$C(R^{20})$= or —N=, $X^3$ is —$C(R^{21})$= or —N=, $X^4$ is —$C(R^{22})$= or —N=;

$R^2$ and $R^{10}$ may be taken together to form —$CH_2$— or —$CH_2$—$CH_2$—, $R^{19}$ is hydrogen or $C_{1-6}$-alkyl optionally substituted with aryl, $R^{20}$, $R^{21}$ and $R^{22}$ independently are hydrogen, —$COOR^{23}$, —$CONR^{24}R^{25}$, —$(CH_2)_wNR^{24}R^{25}$, —$(CH_2)_wOR^{23}$, —$(CH_2)_wR^{23}$ or halogen;

$R^{15}$, $R^{16}$, $R^{23}$, $R^{24}$ and $R^{25}$ independently are hydrogen or $C_{1-6}$-alkyl optionally substituted with halogen, —$N(R^{26})R^{27}$, hydroxyl, $C_{1-6}$-alkoxy, $C_{1-6}$-alkoxycarbonyl, $C_{1-6}$-alkyl-carbonyloxy or aryl, or $R^{16}$ is

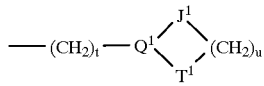

wherein $Q^1$ is —CH< or —N<, $T^1$ and $J^1$ are independently —$CH_2$—, —CO—, —O—, —S—, —$NR^{28}$— or a valence bond, where $R^{28}$ is hydrogen or linear or branched $C_{1-6}$-alkyl;

t and u are independently 0, 1, 2, 3 or 4;

$R^{17}$ is $C_{1-6}$ alkyl or phenyl optionally substituted with hydroxyl or aryl;

$R^{18}$ is $C_{1-6}$ alkyl;

$R^{26}$ and $R^{27}$ are independently hydrogen or $C_{1-6}$-alkyl;

v and w are independently 0, 1, 2 or 3;

$R^{10a}$ is hydrogen, aryl optionally substituted with halogen or $C_{1-6}$-alkyl, or $C_{1-6}$-alkyl optionally substituted with halogen or $C_{1-6}$-alkyl, l is 0, 1, 2, or 3;

$A^1$ is

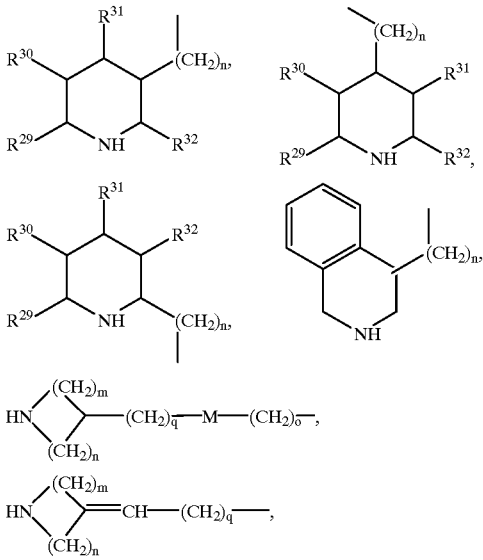

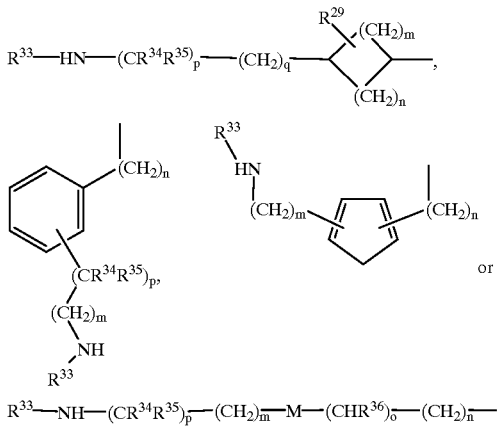

wherein $R^{29}$, $R^{30}$, $R^{31}$, $R^{32}$, $R^{33}$, $R^{34}$, $R^{35}$ and $R^{36}$ are independently hydrogen or $C_{1-6}$-alkyl optionally substituted with halogen, amino, hydroxyl or aryl;

$R^{33}$ and $R^{34}$, $R^{33}$ and $R^{35}$, or $R^{34}$ and $R^{35}$ may optionally form —$(CH_2)_i$—Z—$(CH_2)_j$, wherein i and j independently are 1 or 2 and Z is —O—, —S— or a valence bond;

n, m and q are independently 0, 1, 2, or 3;

o and p are independently 0 or 1;

M is —$CR^{37}$=$CR^{38}$—, —O—, —S—, or a valence bond;

$R^{37}$ and $R^{38}$ are independently hydrogen, or $C_{1-6}$-alkyl optionally substituted with aryl;

$A^2$ is

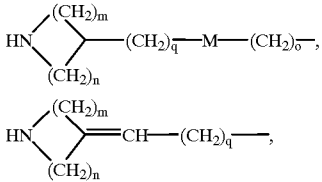

-continued

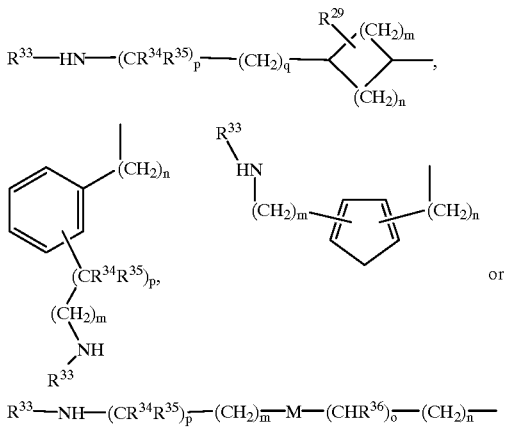

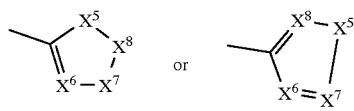

wherein $R^{29}$, $R^{30}$, $R^{31}$, $R^{32}$, $R^{33}$, $R^{34}$, $R^{35}$ and $R^{36}$ are independently hydrogen or $C_{1-6}$-alkyl optionally substituted with halogen, amino, hydroxyl or aryl;

$R^{33}$ and $R^{34}$, $R^{33}$ and $R^{35}$ or $R^{34}$ and $R^{35}$ may optionally form —$(CH_2)_i$—Z—$(CH_2)_j$—, wherein i and j independently are 1 or 2 and Z is —O—, —S— or a valence bond;

n, m and q are independently 0, 1, 2, or 3;

o and p are independently 0 or 1;

M is —$CR^{37}$=$CR^{38}$—, —O—, or —S—;

$R^{37}$ and $R^{38}$ are independently hydrogen, or $C_{1-6}$-alkyl optionally substituted with aryl; $G^1$ is hydrogen, halogen, aryl, $C_{1-6}$-alkyl, $C_{1-6}$-alkoxy, —$CONR^{39}R^{40}$, —$(CH_2)_e$—$NR^{39}SO_2R^{41}$, —$(CH_2)_e$—$NR^{39}COR^{40}$, —$(CH_2)_e$—$OR^{41}$, —$(CH_2)_e$—$OCOR^{40}$, —$CH(R^{39})R^{40}$, —$CON^{39}$—$NR^{40}R^{42}$, —$(CH_2)_e$—$NR^{39}$—CS—$NR^{40}R^{42}$, —$(CH_2)_e$—$NR^{39}$—CO—$NR^{40}R^{42}$,

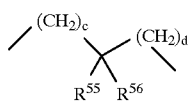

wherein $X^5$ is —$N(R^{43})$—, —O— or —S—, $X^6$ is —$C(R^{44})$= or —N=, $X^7$ is —$C(R^{45})$= or —N=, $X^8$ is —$C(R^{46})$= or —N=, $R^{43}$ is hydrogen or $C_{1-6}$-alkyl optionally substituted with aryl, $R^{43}$, $R^{45}$ and $R^{46}$ independently are hydrogen, —$COOR^{47}$, —$CONR^{48}R^{49}$, —$(CH_2)_f NR^{48}R^{49}$, —$(CH_2)_f OR^{47}$, —$(CH_2)_f R^{47}$ or halogen;

$R^{39}$, $R^{40}$, $R^{47}$, $R^{48}$ and $R^{49}$ independently are hydrogen or $C_{1-6}$-alkyl optionally substituted with halogen, —$N(R^{50})R^{51}$, hydroxyl, $C_{1-6}$alkoxy, $C_{1-6}$-alkoxycarbonyl, $C_{1-6}$-alkylcarbonyloxy or aryl, or $R^{40}$ is

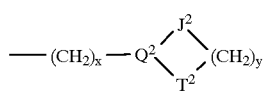

wherein $Q^2$ is —CH< or —N<, $J^2$ and $T^2$ are independently —$CH_2$—, —CO—, —O—, —S—, —$NR^{52}$— or a valence bond, where $R^{52}$ is hydrogen or $C_{1-6}$-alkyl;

x and y are independently 0, 1, 2, 3 or 4;

$R^{41}$ is $C_{1-6}$ alkyl substituted with aryl;

$R^{42}$ is $C_{1-6}$ alkyl;

$R^{50}$ and $R^{51}$ are independently hydrogen or $C_{1-6}$-alkyl;

e and f are independently 0, 1, 2 or 3;

$G^2$ is hydrogen or $C_{1-6}$-alkyl;

$R^1$ is hydrogen or $C_{1-6}$-alkyl;

$R^2$ is hydrogen, —C(=O)—$R^{54}$ or $C_{1-6}$-alkyl;

$R^1$ and $R^2$ may be taken together to form a bridge of type

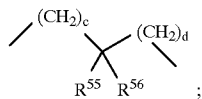

wherein $R^{55}$ and $R^{56}$ independently of each other are hydrogen, $C_{1-6}$-alkyl, optionally substituted with hydroxyl, $C_{1-6}$-alkoxyl or aryl;

$R^{55}$ and $R^{56}$ may be taken together to form =O or =S;

c and d are independently 0, 1, or 2;

c+d is 0, 1, or 2;

$R^{54}$ is hydrogen or $C_{1-6}$-alkyl, $R^3$ and $R^4$ are hydrogen, $C_{1-6}$-alkyl, optionally substituted with hydroxyl, $C_{1-6}$-alkoxyl, halogen, or aryl;

$R^3$ and $R^4$ may be taken together to form =S, =O;

$L^1$ is $CR^{57}$ or N;

$L^2$ is $CR^{58}$ or N;

$R^{57}$ and $R^{58}$ independently are hydrogen, $C_{1-6}$-alkyl, optionally substituted with hydroxyl, halogen, $C_{1-6}$-alkoxy, or aryl;

a and b independently are 0, 1, 2, or 3;

with the proviso that when G is $G^2$ and $L^1$ is $CR^{55}$ and $L^2$ is $CR^{56}$, then A is $A^2$;

when G is $G^1$ and $L^{1\ is\ CR55}$ and $L^2$ is $CR^{56}$, then A is $A^1$ and $R^2$ is —C(=O)—$R^{54}$ or $R^1$ and $R^2$ are taken together to form a bridge of the type

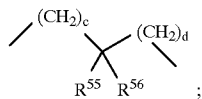;

when either of $L^1$ or $L^2$ is N, then G is $G^1$ and A is $A^1$;

or a pharmaceutically acceptable salt thereof.

In one embodiment of the compound of formula I A is

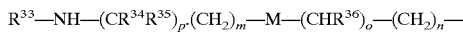

wherein $R^{33}$ is hydrogen or $C_{1-6}$, alkyl optionally substituted with hydroxyl, preferably hydrogen, methyl or hydroxypropyl, e.g. (2R)-2-hydroxypropyl, $R^{34}$ and $R^{35}$ are independently of each other $C_{1-6}$ alkyl, preferably methyl, $R^{36}$ is hydrogen, M is —$CR^{37}$=$CR^{38}$— or —O—, wherein $R^{37}$ and $R^{38}$ are hydrogen or $C_{1-6}$ alkyl, preferably —CH=CH— or O, p is 1, m is 1, o is 0 or 1 and n is 0 or 1.

In another embodiment of the compound of formula I A is

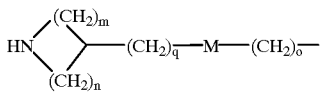

wherein M is —O— or —S—, preferably —O—, o is 0 or 1, preferably 1, q is 0, 1 or 2, preferably 1, and m+n is 3 or 4, preferably 3.

In a further embodiment of the compound of formula I A is

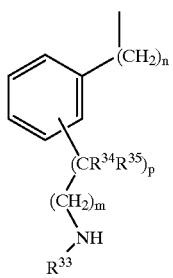

wherein $R^{33}$ is hydrogen or $C_{1-6}$ alkyl, preferably, hydrogen, $R^{34}$ and $R^{35}$ independently of each other are hydrogen or $C_{1-6}$ alkyl, preferably hydrogen or methyl, m is 0 or 1, n is 0 or 1, preferably 0 and p is 0 or 1. In particular the phenylen moiety is meta-substituted, however it might be ortho- or para-substituted as well and the invention is by no means limited hereto.

In the above compound of formula I A is preferably (1E)-4-amino-4-methylbut-1-enyl, (1E)-4-amino-4-methylpent-1-enyl (2-amino-2-methylpropyxy)methyl, ((2S)-pyrrolidin-2-yl)methoxymethyl, 4-piperidinyl, (1E)-4-((2R)-2-hydroxypropylamino)-4-methylbut-1-enyl, (1E)-4-((2R)-2-hydroxypropylamino)-4-methylpent-1-enyl, (1E)-4-methyl-4-methylaminopent-1-enyl, 3-(1-aminoethyl)phenyl or 3-(aminomethyl)phenyl. In one embodiment hereof A is (1 E)-4-amino4-methylbut-1-enyl, (2-amino-2-methylpropoxy)methyl, ((2S)-pyrrolidin-2-yl)methoxymethyl, 4-piperidinyl or (1E)-4-((2R)-2-hydroxypropylamino)-4-methylbut-1-enyl.

In one embodiment of the compound of formula I D is

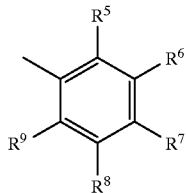

wherein $R^5$, $R^6$, $R^7$, $R^8$ and $R^9$ independently of each other are hydrogen or aryl, preferably hydrogen or phenyl. More preferred $R^5$, $R^6$, $R^8$ and $R^9$ are hydrogen and $R^7$ is phenyl.

In a further embodiment of the compound of formula I D is

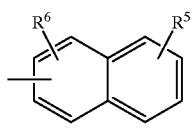

wherein $R^5$ and $R^6$ independently of each other are hydrogen or $C_{1-6}$ alkyl, preferably hydrogen.

In the above compound of formula I D is preferably (2-naphthyl), benzyloxy, or biphenyl-4-yl. More preferred (2-naphthyl) or biphenyl-4-yl.

In one embodiment of the compound of formula I E is

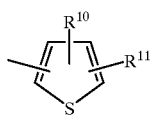

wherein $R^{10}$ and $R^{11}$ independently of each other are hydrogen or $C_{1-6}$ alkyl, preferably hydrogen.

In a further embodiment of the compound of formula I E is

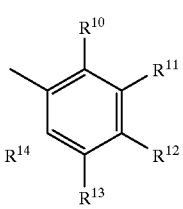

wherein $R^{10}$, $R^{11}$, $R^{12}$, $R^{13}$ and $R^{14}$ independently of each other are hydrogen, —(CH$_2$)$_v$—NR$^{15}$SO$_2$R$^{17}$, —(CH$_2$)$_v$—NR$^{15}$COR$^{16}$ or —(CH$_2$)$_v$—OR$^{17}$, wherein v is 0 or 1, preferably 0, $R^{15}$ is hydrogen or $C_{1-6}$ alkyl, preferably hydrogen, $R^{16}$ is hydrogen or $C_{1-6}$ alkyl optionally substituted with —N(R$^{26}$)R$^{27}$, wherein R$^{26}$ and R$^{27}$ independently of each other are hydrogen or $C_{1-6}$ alkyl, preferably R$^{16}$ is hydrogen or $C_{1-6}$ alkyl substituted with amino, $R^{17}$ is $C_{1-6}$ alkyl or phenyl optionally substituted with hydroxyl or phenyl, preferably methyl, $C_{1-6}$ alkyl substituted with hydroxyl, e.g. —CH$_2$CH$_2$OH or —CH$_2$CH$_2$CH$_2$OH, or phenyl. In particular the phenylen moiety is ortho-substituted, however it may also be meta- or para-substituted and the invention is by no means limited hereto. In one embodiment, when $R^{10}$ or $R^{14}$ is —(CH$_2$)$_v$—NR$^{15}$SO$_2$R$^{17}$, v is 0, $R^{15}$ is hydrogen, and $R^{17}$ is $C_{1-6}$ alkyl or phenyl, preferably methyl or phenyl. In a second embodiment, when $R^{10}$ or $R^{14}$ is —(CH$_2$)$_v$—NR$^{15}$COR$^{16}$, v is 0, $R^{15}$ is hydrogen and $R^{16}$ is hydrogen or $C_{1-6}$ alkyl substituted with —NH$_2$, preferably aminomethyl. In a third embodiment, when $R^{10}$ or $R^{14}$ is —(CH$_2$)$_v$—OR$^{17}$, v is 0, and $R^{17}$ is $C_{1-6}$ alkyl substituted with hydroxyl, preferably —CH$_2$CH$_2$OH or —CH$_2$CH$_2$CH$_2$OH.

In the above compound of formula I E is preferably phenyl, 2-thienyl, 2-(2-hydroxyethoxy)phenyl, 2-(3-hydroxypropoxy)phenyl, biphenyl-4-yl, 2-(aminoacetylamino)phenyl, 2-(phenylsulfonylamino)phenyl or 2-(methylsulfonylamino)phenyl. In one embodiment hereof E is phenyl, 2-thienyl or 2-(methylsulfonylamino)phenyl.

In one embodiment of the compound of formula I G is hydrogen or —CONR$^{39}$R$^{40}$, wherein R$^{39}$ and R$^{40}$ independently of each other are hydrogen or $C_{1-6}$ alkyl, preferably hydrogen, methyl or ethyl. In the above compound of formula I G is preferably hydrogen, methyl, methylcarbamoyl, or ethylcarbamoyl.

In one embodiment of the compound of formula I $R^1$ is hydrogen or $C_{1-6}$ alkyl, preferably hydrogen or $C_{1-4}$ alkyl.

In the above compound of formula I $R^1$ is preferably hydrogen or methyl.

In one embodiment of the compound of formula I $R^2$ is hydrogen, —C(=O)—$R^{54}$ or $C_{1-6}$ alkyl, wherein $R^{54}$ is $C_{1-6}$ alkyl, preferably hydrogen, $C_{1-6}$ alkyl or —C(=O)—$CH_3$.

In the above compound of formula I $R^2$ is preferably methyl, hydrogen, or acetyl.

In the above compound of formula I $R^1$ and $R^2$ may be taken together to form a bridge of type

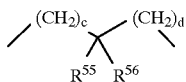

wherein $R^{55}$ and $R^{56}$ are hydrogen, or $R^{55}$ and $R^{56}$ may be taken together to form =O or =S, preferably =O;

c and d are independently 0, 1, or 2, preferably 0 or 1;
c+d is 0, 1, or 2, preferably 1.
In the above compound of formula I $R^1$ and $R^2$ may be taken together to form a bridge of type —$CH_2$—C(=O)— or —$CH_2$—$CH_2$—.

In the above compound of formula I $R^2$ and $R^{10}$ may be taken together to form —$(CH_2)_r$—, wherein r is 1, 2 or 3, preferably 1 or 2, more preferred 1. In a preferred embodiment E is phenyl, wherein $R^{11}$ to $R^{14}$ is hydrogen and $R^{10}$ is taken together with $R^2$ to form —$(CH_2)_r$—.

In one embodiment of the compound of formula I $R^3$ is hydrogen or $C_{1-6}$ alkyl, preferably hydrogen.

In one embodiment of the compound of formula I $R^4$ is hydrogen or $C_{1-6}$ alkyl, preferably hydrogen.

In the above compound of formula I $R^3$ and $R^4$ may be taken together to form =O.

In the above compound of formula I a is preferably 1.
In the above compound of formula I b is preferably 0 or 1.

In the above compound of formula I $L^1$ is preferably —CH—.

In the above compound of formula I $L^2$ is preferably —CH— or >N—.

One embodiment of the compound of formula I relates to a compound of the general formula II

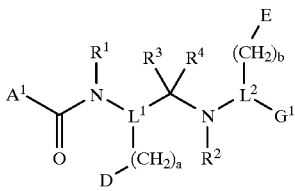

wherein
$L^1$ is $CR^{57}$ or N;
$L^2$ is $CR^{58}$ or N;
$R^{57}$ and $R^{58}$ independently are hydrogen, $C_{1-6}$-alkyl, optionally substituted with hydroxyl, halogen, $C_{1-6}$-alkoxy, or aryl;
with the proviso that either $L^1$ or $L^2$ is N; and $A^1$, $R^1$, $R^2$, $R^3$, $R^4$, $G^1$, D, E, a, and b are defined above;
or a pharmaceutically acceptable salt thereof.

In one embodiment of the compound of formula II $A^1$ is

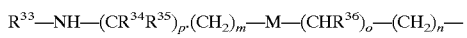

wherein $R^{33}$ is hydrogen or $C_{1-6}$ alkyl optionally substituted with hydroxyl, preferably hydrogen, methyl or hydroxypropyl, e.g. (2R)-2-hydroxypropyl, $R^{34}$ and $R^{35}$ are independently of each other $C_{1-6}$ alkyl, preferably methyl,
$R^{36}$ is hydrogen,
M is —$CR^{37}$=$CR^{38}$— or —O—, wherein $R^{37}$ and $R^{38}$ are hydrogen or $C_{1-6}$ alkyl, preferably —CH=CH— or O
p is 1, m is 1, o is 0 or 1 and n is 0 or 1.

In another embodiment of the compound of formula II $A^1$ is

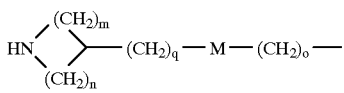

wherein M is —O— or —S—, preferably —O—,
o is 0 or 1, preferably 1,
q is 0, 1 or 2, preferably 1, and
m+n is 3 or 4, preferably 3.

In a further embodiment of the compound of formula II $A^1$ is

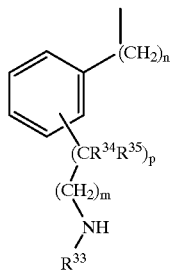

wherein $R^{33}$ is hydrogen or $C_{1-6}$ alkyl, preferably, hydrogen,
$R^{34}$ and $R^{35}$ independently of each other are hydrogen or $C_{1-6}$ alkyl, preferably hydrogen or methyl,
m is 0 or 1, n is 0 or 1, preferably 0 and p is 0 or 1. In particular the phenylen moiety is meta-substituted, however it might be ortho- or para-substituted as well and the invention is by no means limited hereto.

In the above compound of formula II $A^1$ is preferably (1E)-4-amino-4-methylbut-1-enyl, (1E)-4-amino-4-methylpent-1-enyl (2-amino-2-methylpropoxy)methyl, ((2S)-pyrrolidin-2-yl)methoxymethyl, 4-piperidinyl, (1E)-4-((2R)-2-hydroxypropylamino)-4-methylbut-1-enyl, (1E)-4-((2R)-2-hydroxypropylamino)4-methylpent-1-enyl, (1E)-4-methyl-4-methylaminopent-1-enyl, 3-(1-aminoethyl)phenyl or 3-(aminomethyl)phenyl. In one embodiment hereof $A^1$ is (1E)-4-amino-4-methylbut-1-enyl, (2-amino-2-methylpropyxy)methyl, ((2S)-pyrrolidin-2-yl) methoxymethyl, 4-piperidinyl, or (1E)-4-((2R)-2-hydroxypropylamino)-4-methylbut-1-enyl. In another embodiment hereof $A^1$ is (1E)-4-amino-4-methylpent-1-enyl, (2-amino-2-methylpropyxy)methyl or ((2S)-pyrrolidin-2-yl)methoxymethyl.

In one embodiment of the compound of formula II D is

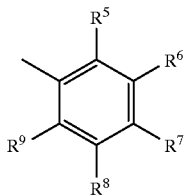

wherein $R^5$, $R^6$, $R^7$, $R^8$ and $R^9$ independently of each other are hydrogen or aryl, prefarably hydrogen or phenyl. More preferred $R^5$, $R^6$, $R^8$ and $R^9$ are hydrogen and $R^7$ is phenyl.

In a further embodiment of the compound of formula II D is

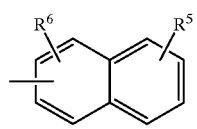

wherein $R^5$ and $R^6$ independently of each other are hydrogen or $C_{1-6}$ alkyl, preferably $R^5$ and $R^6$ are both hydrogen.

In the above compound of formula II D is preferably (2-naphthyl), benzyloxy, or biphenyl-4-yl. More preferred (2-naphthyl) or biphenyl-4-yl. In one embodiment 2-naphthyl.

In one embodiment of the compound of formula II E is

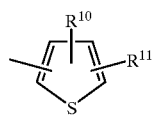

wherein $R^{10}$ and $R^{11}$ independently of each other are hydrogen or $C_{1-6}$ alkyl, preferably hydrogen.

In another embodiment of the compound of formula II E is

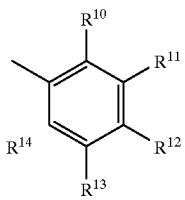

wherein $R^{10}$, $R^{11}$, $R^{12}$, $R^{13}$ and $R^{14}$ independently of each other are hydrogen, —$(CH_2)_v$—$NR^{15}SO_2R^{17}$, —$(CH_2)_v$—$NR^{15}COR^{16}$ or —$(CH_2)_v$—$OR^{17}$, wherein v is 0 or 1, perferably 0, $R^{15}$ is hydrogen or $C_{1-6}$ alkyl, preferably hydrogen, $R^{16}$ is hydrogen or $C_{1-6}$ alkyl optionally substituted with —$N(R^{26})R^{27}$, wherein $R^{26}$ and $R^{27}$ independently of each other are hydrogen or $C_{1-6}$ alkyl, preferably $R^{16}$ is hydrogen or $C_{1-6}$ alkyl substituted with amino, $R^{17}$ is $C_{1-6}$ alkyl or phenyl optionally substituted with hydroxyl or phenyl, preferably methyl, $C_{1-6}$ alkyl substituted with hydroxyl, e.g. —$CH_2CH_2OH$ or —$CH_2CH_2CH_2OH$, or phenyl. In particular the phenylen moiety is ortho—substituted, however it may also be meta- or para—substituted and the invention is by no means limited hereto. In one embodiment, when $R^{10}$ or $R^{14}$ is —$(CH_2)_v$—$NR^{15}SO_2R^{17}$, v is 0, $R^{15}$ is hydrogen, and $R^{17}$ is $C_{1-6}$ alkyl or phenyl, preferably methyl or phenyl. In a second embodiment, when $R^{10}$ or $R^{14}$ is —$(CH_2)_v$—$NR^{15}COR^{16}$, v is 0, $R^{15}$ is hydrogen and $R^{16}$ is hydrogen or $C_{1-6}$ alkyl substituted with —$NH_2$, preferably aminomethyl. In a third embodiment, when $R^{10}$ or $R^{14}$ is —$(CH_2)_v$—$OR^{17}$, v is 0, and $R^{17}$ is $C_{1-6}$ alkyl substituted with hydroxyl, preferably —$CH_2CH_2OH$ or —$CH_2CH_2CH_2OH$.

In the above compound of formula II E is preferably phenyl, 2-thienyl, 2-(2-hydroxyethoxy)phenyl, 2-(3-hydroxypropoxy)phenyl, biphenyl-4-yl, 2-(aminoacetylamino)phenyl, 2-(phenylsulfonylamino) phenyl or 2-(methylsulfonylamino)phenyl. In one embodiment hereof E is phenyl, 2-thienyl or 2-(methylsulfonylamino)phenyl, preferably phenyl, or 2-thienyl, more preferred phenyl.

In one embodiment of the compound of formula II $G^1$ is hydrogen or —$CONR^{39}R^{40}$, wherein $R^{39}$ and $R^{40}$ independently of each other are hydrogen or $C_{1-6}$ alkyl, preferably one of $R^{39}$ or $R^4$ is hydrogen and the other is methyl or ethyl.

In the above compound of formula II $G^1$ is preferably hydrogen, methylcarbamoyl, or ethylcarbamoyl.

In one embodiment of the compound of formula II $R^1$ is $C_{1-6}$ alkyl, preferably hydrogen or $C_{1-4}$ alkyl.

In the above compound of formula II $R^1$ is preferably methyl.

In one embodiment of the compound of formula II $R^2$ is hydrogen, —$C(=O)$—$R^{54}$ or $C_{1-6}$ alkyl, wherein $R^{54}$ is $C_{1-6}$ alkyl, preferably hydrogen, $C_{1-6}$ alkyl or —$C(=O)$—$CH_3$.

In the above compound of formula II $R^2$ is preferably methyl, hydrogen, or acetyl, more preferred methyl or hydrogen, most preferred hydrogen.

In the above compound of formula II $R^1$ and $R^2$ may be taken together to form a bridge of type

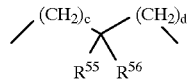

wherein $R^{55}$ and $R^{56}$ are hydrogen, or $R^{55}$ and $R^{56}$ may be taken together to form =O or =S, preferably =O;

c and d are independently 0, 1, or 2, preferably 0 or 1;

c+d is 0, 1, or 2, preferably 1.

In one embodiment of the above compound of formula II $R^1$ and $R^2$ may be taken together to form a bridge of type —$CH_2$—$C(=O)$—. In another embodiment of the above compound of formula II $R^1$ and $R^2$ may be taken together to form a bridge of the type —$CH_2$—$CH_2$—.

In one embodiment of the compound of formula II $R^3$ is hydrogen or $C_{1-6}$ alkyl, preferably hydrogen.

In one embodiment of the compound of formula II $R^4$ is hydrogen or $C_{1-6}$ alkyl, preferably hydrogen.

In the above compound of formula II $R^3$ and $R^4$ may be taken together to form =O.

In the above compound of formula II a is preferably 1.

In the above compound of formula II b is preferably 1.

In the above compound of formula II $L^1$ is preferably —CH—.

In the above compound of formula II $L^2$ is preferably —CH— or >N—.

A further embodiment of the compound of formula I relates to a compound of the general formula III formula III

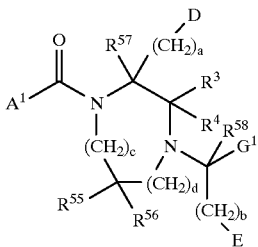

wherein
A¹, D, E, G¹, R³, R⁴, R⁵⁵, R⁵⁶, R⁵⁷, R⁵⁸, a, b, c, and d are defined above; or a pharmaceutically acceptable salt thereof.

In one embodiment of the compound of formula III A¹ is $R^{33}-NH-(CR^{34}R^{35})_p-(CH_2)_m-M-(CHR^{36})_o-(CH_2)_n-$ wherein $R^{33}$ is hydrogen or $C_{1-6}$ alkyl optionally substituted with hydroxyl, preferably hydrogen, methyl or hydroxypropyl, more preferred hydrogen, $R^{34}$ and $R^{35}$ are independently of each other $C_{1-6}$ alkyl, preferably methyl, $R^{36}$ is hydrogen, M is $-CR^{37}=CR^{38}-$ or $-O-$, wherein $R^{37}$ and $R^{38}$ are hydrogen or $C_{1-6}$ alkyl, preferably $-CH=CH-$, p is 1, m is 1, o is 0 or 1, preferably 0 and n is 0 or 1, preferably 0.

In another embodiment of the compound of formula III A¹ is

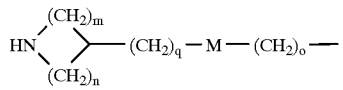

wherein M is $-O-$ or $-S-$, preferably $-O-$,
o is 0 or 1, preferably 1,
q is 0, 1 or 2, preferably 1, and
m+n is 3 or 4, preferably 3.

In a further embodiment of the compound of formula III A¹ is

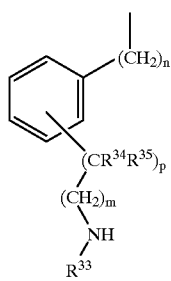

wherein $R^{33}$ is hydrogen or $C_{1-6}$ alkyl, preferably, hydrogen,
$R^{34}$ and $R^{35}$ independently of each other are hydrogen or $C_{1-6}$ alkyl, preferably hydrogen or methyl,
m is 0 or 1, n is 0 or 1, preferably 0 and p is 0 or 1. In particular the phenylen moiety is meta-substituted, however it might be ortho- or para-substituted as well and the invention is by no means limited hereto.

In the above compound of formula III A¹ is preferably (1E)-4-amino-4-methylbut-1-enyl, (1E)-4-amino-4-methylpent-1-enyl (2-amino-2-methylpropyxy)methyl, ((2S)-pyrrolidin-2-yl)methoxymethyl, 4-piperidinyl, (1E)-4-((2R)-2-hydroxypropylamino)-4-methylbut-1-enyl, (1E)-4-((2R)-2-hydroxypropylamino)-4-methylpent-1-enyl, (1E)-4-methyl-4-methylaminopent-1-enyl 3-(1-aminoethyl)phenyl or 3-(aminomethyl)phenyl. In one embodiment hereof A¹ is (1E)-4-amino4-methylbut-1-enyl, (2-amino-2-methylpropyxy)methyl or ((2S)-pyrrolidin-2-yl)methoxymethyl. In another embodiment hereof A¹ is (1E)-4-amino-4-methylpent-1-enyl.

In one embodiment of the compound of formula III D is

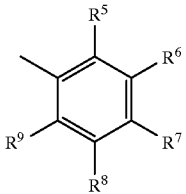

wherein $R^5$, $R^6$, $R^7$, $R^8$ and $R^9$ independently of each other are hydrogen or aryl, preferably hydrogen or phenyl. More preferred $R^5$, $R^6$, $R^8$ and $R^9$ are hydrogen and $R^7$ is phenyl.

In a further embodiment of the compound of formula III D is

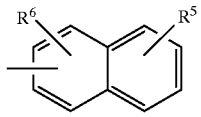

wherein $R^5$ and $R^6$ independently of each other are hydrogen or $C_{1-6}$ alkyl, preferably $R^5$ and $R^6$ are both hydrogen.

In the above compound of formula III D is preferably (2-naphthyl), benzyloxy, or biphenyl-4-yl. More preferred (2-naphthyl).

In one embodiment of the compound of formula III E is

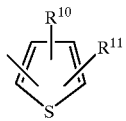

wherein $R^{10}$ and $R^{11}$ independently of each other are hydrogen or $C_{1-6}$ alkyl, preferably hydrogen.

In a further embodiment of the compound of formula III E is

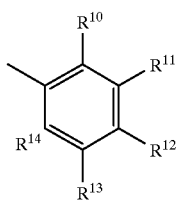

wherein $R^{10}$, $R^{11}$, $R^{12}$, $R^{13}$ and $R^{14}$ independently of each other are hydrogen, $-(CH_2)_v-NR^{15}SO_2R^{17}$, $-(CH_2)_v-NR^{15}COR^{16}$ or $-(CH_2)_v-OR^{17}$, wherein v is 0 or 1, preferably 0, $R^{15}$ is hydrogen or $C_{1-6}$ alkyl, preferably hydrogen, $R^{16}$ is hydrogen or $C_{1-6}$ alkyl optionally substituted with $-N(R^{26})R^{27}$, wherein $R^{26}$ and $R^{27}$ independently of each other are hydrogen or $C_{1-6}$ alkyl, preferably $R^{16}$ is hydrogen or $C_{1-6}$ alkyl substituted with amino, $R^{17}$ is $C_{1-6}$ alkyl or phenyl optionally substituted with hydroxyl or phenyl, preferably methyl, $C_{1-6}$ alkyl substituted with hydroxyl, e.g. —$CH_2CH_2OH$ or —$CH_2CH_2CH_2OH$, or phenyl. In particular the phenylen moiety is ortho-substituted, however it may also be meta- or para-substituted and the invention is by no means limited hereto. In one embodiment, when $R^{10}$ or $R^{14}$ is —$(CH_2)_v$—$NR^{15}SO_2R^{17}$, v is 0, $R^{15}$ is hydrogen, and $R^{17}$ is $C_{1-6}$ alkyl or phenyl, preferably methyl or phenyl. In a second embodiment, when $R^{10}$ or $R^{14}$ is —$(CH_2)_v$—$NR^{15}COR^{16}$, v is 0, $R^{15}$ is hydrogen and $R^{16}$ is hydrogen or $C_{1-6}$ alkyl substituted with —$NH_2$, preferably aminomethyl. In a third embodiment, when $R^{10}$ or $R^{14}$ is —$(CH_2)_v$—$OR^{17}$, v is 0, and $R^{17}$ is $C_{1-6}$ alkyl substituted with hydroxyl, preferably —$CH_2CH_2OH$ or —$CH_2CH_2CH_2OH$.

In the above compound of formula I E is preferably phenyl, 2-thienyl, 2-(2-hydroxyethoxy)phenyl, 2-(3-hydroxypropoxy)phenyl, biphenyl-4-yl, 2-(aminoacetylamino)phenyl, 2-(phenylsulfonylamino) phenyl or 2-(methylsulfonylamino)phenyl. In one embodiment hereof E is phenyl, 2-thienyl or 2-(methylsulfonylamino)phenyl, preferably phenyl.

In one embodiment of the compound of formula III $G^1$ is hydrogen or —$CONR^{39}R^{40}$, wherein $R^{39}$ and $R^{40}$ independently of each other are hydrogen or $C_{1-6}$ alkyl, preferably hydrogen or methyl.

In the above compound of formula III $G^1$ is preferably hydrogen or methylcarbamoyl.

In one embodiment of the compound of formula III $R^3$ is hydrogen or $C_{1-6}$ alkyl, preferably hydrogen.

In one embodiment of the compound of formula III $R^4$ is hydrogen or $C_{1-6}$ alkyl, preferably hydrogen.

In the above compound of formula III $R^3$ and $R^4$ may be taken together to form =O.

In the above compound of formula III a is preferably 1.
In the above compound of formula III b is preferably 1.
In the above compound of formula III $R^{55}$ and $R^{56}$ are hydrogen, or $R^{55}$ and $R^{56}$ may be taken together to form =O;

c and d are independently 0, 1, or 2, preferably 0 or 1;
c+d is 0, 1, or 2, preferably 1.

In the above compound of formula III $R^{57}$ and $R^{58}$ are independently hydrogen or $C_{1-6}$-alkyl, preferably hydrogen.

A still further embodiment of the compound of formula I relates to a compound of the general formula IV Formula IV

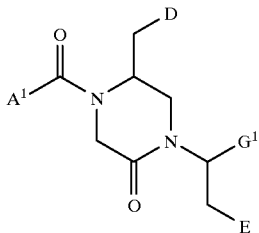

wherein
$A^1$, D, E, and $G^1$ are defined above;
or a pharmaceutically acceptable salt thereof.
In one embodiment of the compound of formula IV $A^1$ is

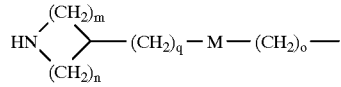

wherein $R^{33}$ is hydrogen or $C_{1-6}$ alkyl optionally substituted with hydroxyl, preferably hydrogen, $R^{34}$ and $R^{35}$ are independently of each other $C_{1-6}$ alkyl, preferably methyl,
M is —$CR^{37}$=$CR^{38}$— or —O—, wherein $R^{37}$ and $R^{38}$ are hydrogen or $C_{1-6}$ alkyl, preferably —CH=CH—,
p is 1, m is 1, o is 0 and n is 0.

In another embodiment of the compound of formula IV $A^1$ is

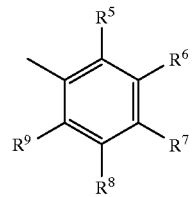

wherein M is —O— or —S—, preferably —O—,
o is 0 or 1, preferably 1,
q is 0, 1 or 2, preferably 1, and
m+n is 3 or 4, preferably 3.

In a further embodiment of the compound of formula IV $A^1$ is

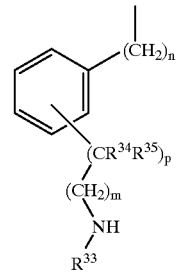

wherein $R^{33}$ is hydrogen or $C_{1-6}$ alkyl, preferably, hydrogen,
$R^{34}$ and $R^{35}$ independently of each other are hydrogen or $C_{1-6}$ alkyl, preferably hydrogen or methyl,
m is 0 or 1, n is 0 or 1, preferably 0 and p is 0 or 1. In particular the phenylen moiety is meta-substituted, however it might be ortho- or para-substituted as well and the invention is by no means limited hereto.

In the above compound of formula IV $A^1$ is preferably (1E)-4-amino-4-methylbut-1-enyl, (1E)-4-amino4-methylpent-1-enyl (2-amino-2-methylpropyxy)methyl, ((2S)-pyrrolidin-2-yl)methoxymethyl, 4-piperidinyl, (1E)-4-((2R)-2-hydroxypropylamino)-4-methylbut-1-enyl, (1E)-4-((2R)-2-hydroxypropylamino)-4-methylpent-1-enyl, (1E)-4-methyl-4-methylaminopent-1-enyl, 3-(1-aminoethyl) phenyl or 3-(aminomethyl)phenyl. In one embodiment hereof $A^1$ is (1E)-4-amino-4-methylbut-1-enyl, (2-amino-2-methylpropyxy)methyl, ((2S)-pyrrolidin-2-yl) methoxymethyl, 4-piperidinyl, or (1E)-4-((2R)-2-hydroxypropylamino)-4-methylbut-1-enyl. In another embodiment hereof $A^1$ is (1E)-4-amino-4-methylpent-1-enyl.

In one embodiment of the compound of formula IV D is $R^{33}$—NH—$(CR^{34}R^{35})_p$-$(CH_2)_m$—M—$(CHR^{36})_o$—$(CH_2)_n$— wherein $R^5$, $R^6$, $R^7$, $R^8$ and $R^9$ independently of each other are hydrogen or aryl, prefarably hydrogen or phenyl. More preferred $R^5$, $R^6$, $R^8$ and $R^9$ are hydrogen and $R^7$ is phenyl.

In a further embodiment of the compound of formula IV D is

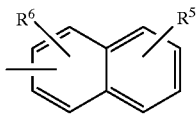

wherein $R^5$ and $R^6$ independently of each other are hydrogen or $C_{1-6}$ alkyl, preferably $R^5$ and $R^6$ are both hydrogen.

In the above compound of formula IV D is preferably (2-naphthyl), benzyloxy, or biphenyl-4-yl. More preferred (2-naphthyl).

In one embodiment of the compound of formula IV E is

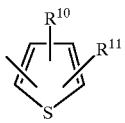

wherein $R^{10}$ and $R^{11}$ independently of each other are hydrogen or $C_{1-6}$ alkyl, preferably hydrogen.

In a further embodiment of the compound of formula IV E is

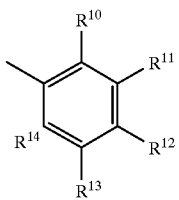

wherein $R^{10}$, $R^{11}$, $R^{12}$, $R^{13}$ and $R^{14}$ independently of each other are hydrogen, —$(CH_2)_v$—$NR^{15}SO_2R^{17}$, —$(CH_2)_v$—$NR^{15}COR^{16}$ or —$(CH_2)_v$—$OR^{17}$, wherein v is 0 or 1, preferably 0, $R^{15}$ is hydrogen or $C_{1-6}$ alkyl, preferably hydrogen, $R^{16}$ is hydrogen or $C_{1-6}$ alkyl optionally substituted with —$N(R^{26})R^{27}$, wherein $R^{26}$ and $R^{27}$ independently of each other are hydrogen or $C_{1-6}$ alkyl, preferably $R^{16}$ is hydrogen or $C_{1-6}$ alkyl substituted with amino, $R^{17}$ is $C_{1-6}$ alkyl or phenyl optionally substituted with hydroxyl or phenyl, preferably methyl, $C_{1-6}$ alkyl substituted with hydroxyl, e.g. —$CH_2CH_2OH$ or —$CH_2CH_2CH_2OH$, or phenyl. In particular the phenylen moiety is ortho-substituted, however it may also be meta- or para-substituted and the invention is by no means limited hereto. In one embodiment, when $R^{10}$ or $R^{14}$ is —$(CH_2)_v$—$NR^{15}SO_2R^{17}$, v is 0, $R^{15}$ is hydrogen, and $R^{17}$ is $C_{1-6}$ alkyl or phenyl, preferably methyl or phenyl. In a second embodiment, when $R^{10}$ or $R^{14}$ is —$(CH_2)_v$—$NR^{15}COR^{16}$, v is 0, $R^{15}$ is hydrogen and $R^{16}$ is hydrogen or $C_{1-6}$ alkyl substituted with —$NH_2$, preferably aminomethyl. In a third embodiment, when $R^{10}$ or $R^{14}$ is —$(CH_2)_v$—$OR^{17}$, v is 0, and $R^{17}$ is $C_{1-6}$ alkyl substituted with hydroxyl, preferably —$CH_2CH_2OH$ or —$CH_2CH_2CH_2OH$.

In the above compound of formula IV E is preferably phenyl, 2-thienyl, 2-(2-hydroxyethoxy)phenyl, 2-(3-hydroxypropoxy)phenyl, biphenyl-4-yl, 2-(aminoacetylamino)phenyl, 2-(phenylsulfonylamino)phenyl or 2-(methylsulfonylamino)phenyl. In one embodiment hereof E is phenyl, 2-thienyl or 2-(methylsulfonylamino)phenyl, preferably phenyl.

In one embodiment of the compound of formula IV $G^1$ is hydrogen or —$CONR^{39}R^{40}$, wherein $R^{39}$ and $R^{40}$ independently of each other are hydrogen or $C_{1-6}$ alkyl, preferably hydrogen or methyl.

In the above compound of formula IV $G^1$ is preferably hydrogen or methylcarbamoyl, preferably methylcarbamoyl.

A further embodiment of the compound of formula I relates to a compound of the general formula V formula V

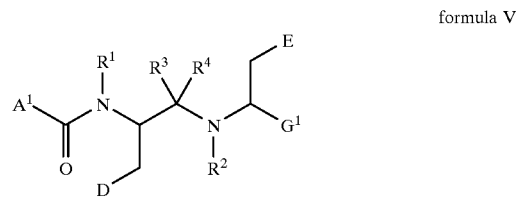

wherein $R^2$ is —$C(=O)$—$R^{54}$ wherein $R^{54}$ is hydrogen or $C_{1-6}$-alkyl; and $A^1$, D, E, $G^1$, $R^1$, $R^3$, and $R^4$ are defined above;

or a pharmaceutically acceptable salt thereof.

In one embodiment of the compound of formula II $A^1$ is

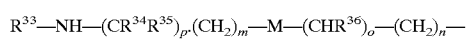

wherein $R^{33}$ is hydrogen or $C_{1-6}$ alkyl optionally substituted with hydroxyl, preferably hydrogen, methyl or hydroxypropyl, e.g. (2R)-2-hydroxypropyl, $R^{34}$ and $R^{35}$ are independently of each other $C_{1-6}$ alkyl, preferably methyl, $R^{36}$ is hydrogen, M is —$CR^{37}=CR^{38}$— or —O—, wherein $R^{37}$ and $R^{38}$ are hydrogen or $C_{1-6}$ alkyl, preferably —$CH=CH$— or O, p is 1, m is 1, o is 0 or 1 and n is 0 or 1.

In another embodiment of the compound of formula II $A^1$ is

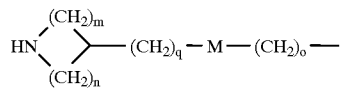

wherein M is —O— or —S—, preferably —O—, o is 0 or 1, preferably 1, q is 0, 1 or 2, preferably 1, and m+n is 3 or 4, preferably 3.

In a further embodiment of the compound of formula V $A^1$ is

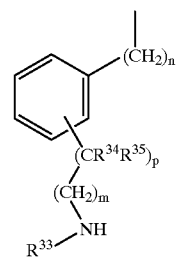

wherein $R^{33}$ is hydrogen or $C_{1-6}$ alkyl, preferably, hydrogen, $R^{34}$ and $R^{35}$ independently of each other are hydrogen or $C_{1-6}$ alkyl, preferably hydrogen or methyl, m is 0 or 1, n is 0 or 1, preferably 0 and p is 0 or 1. In particular the phenylen moiety is meta-substituted, however it might be ortho- or para-substituted as well and the invention is by no means limited hereto.

In the above compound of formula V $A^1$ is preferably (1E)-4-amino-4-methylbut-1-enyl, (1E)-4-amino4-methylpent-1-enyl (2-amino-2-methylpropyxy)methyl, ((2S)-pyrrolidin-2-yl)methoxymethyl, 4-piperidinyl, (1E)-4-((2R)-2-hydroxypropylamino)-4-methylbut-1-enyl, (1E)-4-((2R)-2-hydroxypropylamino)-4-methylpent-1-enyl, (1E)-4-methyl-4-methylaminopent-1-enyl 3-(1-aminoethyl)phenyl or 3-(aminomethyl)phenyl. In one embodiment hereof $A^1$ is preferably (1E)-4-amino-4-methylbut-l-enyl, (2-amino-2-methylpropyxy)methyl, ((2S)-pyrrolidin-2-yl)methoxymethyl, 4-piperidinyl, or (1E)-4-((2R)-2-hydroxypropylamino)-4-methylbut-1-enyl.

In one embodiment of the compound of formula V D is

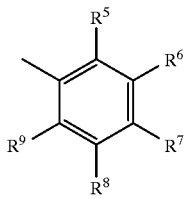

wherein $R^5$, $R^6$, $R^7$, $R^8$ and $R^9$ independently of each other are hydrogen or aryl, prefarably hydrogen or phenyl. More preferred $R^5$, $R^6$, $R^8$ and $R^9$ are hydrogen and $R^7$ is phenyl.

In a further embodiment of the compound of formula V D is

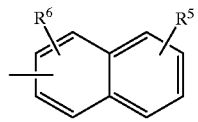

wherein $R^5$ and $R^6$ independently of each other are hydrogen or $C_{1-6}$ alkyl, preferably hydrogen.

In the above compound of formula V D is preferably (2-naphthyl), benzyloxy, or biphenyl-4-yl. More preferred (2-naphthyl) or biphenyl-4-yl.

In one embodiment of the compound of formula V E is

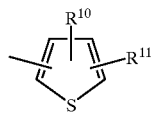

wherein $R^{10}$ and $R^{11}$ independently of each other are hydrogen or $C_{1-6}$ alkyl, preferably hydrogen.

In a further embodiment of the compound of formula V E is

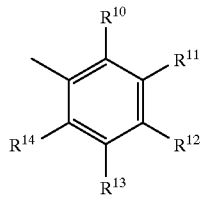

wherein $R^{10}$, $R^{11}$, $R^{12}$, $R^{13}$ and $R^{14}$ independently of each other are hydrogen, —$(CH_2)_v$—$NR^{15}SO_2R^{17}$, —$(CH_2)_v$—$NR^{15}COR^{16}$ or —$(CH_2)_v$—$OR^{17}$, wherein v is 0 or 1, preferably 0, $R^{15}$ is hydrogen or $C_{1-6}$ alkyl, preferably hydrogen, $R^{16}$ is hydrogen or $C_{1-6}$ alkyl optionally substituted with —$N(R^{26})R^{27}$, wherein $R^{26}$ and $R^{27}$ independently of each other are hydrogen or $C_{1-6}$ alkyl, preferably $R^{16}$ is hydrogen or $C_{1-6}$ alkyl substituted with amino, $R^{17}$ is $C_{1-6}$ alkyl or phenyl optionally substituted with hydroxyl or phenyl, preferably methyl, $C_{1-6}$ alkyl substituted with hydroxyl, e.g. —$CH_2CH_2OH$ or —$CH_2CH_2CH_2OH$, or phenyl. In particular the phenylen moiety is ortho-substituted, however it may also be meta- or para-substituted and the invention is by no means limited hereto. In one embodiment, when $R^{10}$ or $R^{14}$ is —$(CH_2)_v$—$NR^{15}SO_2R^{17}$, v is 0, $R^{15}$ is hydrogen, and $R^{17}$ is $C_{1-6}$ alkyl or phenyl, preferably methyl or phenyl. In a second embodiment, when $R^{10}$ or $R^{14}$ is —$(CH_2)_v$—$NR^{15}COR^6$, v is 0, $R^{15}$ is hydrogen and $R^{16}$ is hydrogen or $C_{1-6}$ alkyl substituted with —$NH_2$, preferably aminomethyl. In a third embodiment, when $R^{10}$ or $R^{14}$ is —$(CH_2)_v$—$OR^{17}$, v is 0, and $R^{17}$ is $C_{1-6}$ alkyl substituted with hydroxyl, preferably —$CH_2CH_2OH$ or —$CH_2CH_2CH_2OH$.

In the above compound of formula II E is preferably phenyl, 2-thienyl, 2-(2-hydroxyethoxy)phenyl, 2-(3-hydroxypropoxy)phenyl, biphenyl-4-yl, 2-(aminoacetylamino)phenyl, 2-(phenylsulfonylamino) phenyl or 2-(methylsulfonylamino)phenyl. In one embodiment hereof E is phenyl, 2-thienyl or 2-(methylsulfonylamino)phenyl, preferably phenyl, or 2-thienyl.

In one embodiment of the compound of formula V $G^1$ is hydrogen or —$CONR^{39}R^{40}$, wherein $R^{39}$ and $R^{40}$ independently of each other are hydrogen or $C_{1-6}$ alkyl, preferably hydrogen, methyl or ethyl.

In the above compound of formula V $G^1$ is preferably hydrogen, methyl, methylcarbamoyl, or ethylcarbamoyl.

In one embodiment of the compound of formula V $R^1$ is $C_{1-6}$ alkyl, preferably hydrogen or $C_{1-4}$ alkyl.

In the above compound of formula V $R^1$ is preferably hydrogen or methyl, most preferred hydrogen.

In one embodiment of the compound of formula V $R^2$ is —C(=O)—$R^{54}$, wherein $R^{54}$ is $C_{1-4}$ alkyl, preferably —C(=O)—$CH_3$.

In one embodiment of the compound of formula V $R^3$ is hydrogen or $C_{1-6}$ alkyl, preferably hydrogen.

In one embodiment of the compound of formula V $R^4$ is hydrogen or $C_{1-6}$ alkyl, preferably hydrogen.

A still further embodiment of the compound of formula I relates to a compound of the general formula VI

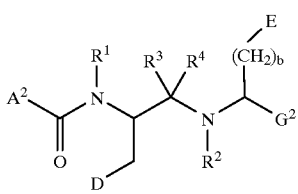

formula VI wherein $A^2$, D, E, $G^2$, $R^1$, $R^2$, $R^3$, $R^4$, and b are defined above;
or a pharmaceutically acceptable salt thereof.
In one embodiment of the compound of formula VI $A^2$ is

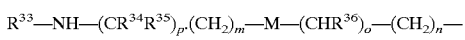

wherein $R^{33}$ is hydrogen or $C_{1-6}$ alkyl optionally substituted with hydroxyl, preferably hydrogen, methyl or hydroxypropyl, e.g. (2R)-2-hydroxypropyl, $R^{34}$ and $R^{35}$ are independently of each other $C_{1-6}$ alkyl, preferably methyl, M is —$CR^{37}$=$CR^{38}$— or —O—, wherein $R^{37}$ and $R^{38}$ are hydrogen or $C_{1-6}$ alkyl, preferably —CH=CH—, p is 1, m is 1, O is 0 and n is 0 or 1, preferably 0.

In another embodiment of the compound of formula VI $A^2$ is

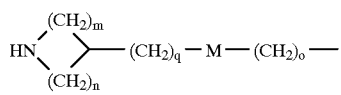

wherein M is —O— or —S—, preferably —O—,
o is 0 or 1, preferably 1,
q is 0, 1 or 2, preferably 1, and
m+n is 3 or 4, preferably 3.

In a further embodiment of the compound of formula VI $A^2$ is

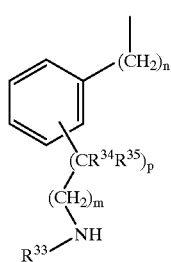

wherein $R^{33}$ is hydrogen or $C_{1-6}$ alkyl, preferably, hydrogen,
$R^{34}$ and $R^{35}$ independently of each other are hydrogen or $C_{1-6}$ alkyl, preferably hydrogen or methyl,
m is 0 or 1, n is 0 or 1, preferably 0 and p is 0 or 1. In particular the phenylen moiety is meta-substituted, however it might be ortho- or para-substituted as well and the invention is by no means limited hereto.

In the above compound of formula VI $A^2$ is preferably (1E)-4-amino-4-methylbut-1-enyl, (1E)-4-amino-4-methylpent-1-enyl (2-amino-2-methylpropyxy)methyl, ((2S)-pyrrolidin-2-yl)methoxymethyl, 4-piperidinyl, (1E)-4-((2R)-2-hydroxypropylamino)-4-methylbut-1-enyl, (1E)-4-((2R)-2-hydroxypropylamino)-4-methylpent-1-enyl, (1E)-4-methyl-4-methylaminopent-1-enyl, 3-(1-aminoethyl)phenyl or 3-(aminomethyl)phenyl. In one embodiment hereof $A^2$ is (1E)-4-amino-4-methylbut-1-enyl, (2-amino-2-methylpropoxy)methyl, ((2S)-pyrrolidin-2-yl)methoxymethyl, 4-piperidinyl or (1E)-4-((2R)-2-hydroxypropylamino)-4-methylbut-1-enyl. In another embodiment hereof $A^2$ is (1E)-4-amino-4-methylpent-1-enyl, 4-piperidinyl or (1E)-4-((2R)-2-hydroxypropylamino)-4-methylbut-1-enyl.

In one embodiment of the compound of formula VI D is

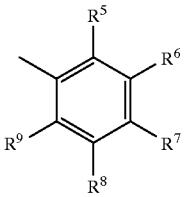

wherein $R^5$, $R^6$, $R^7$, $R^8$ and $R^9$ independently of each other are hydrogen or aryl, prefarably hydrogen or phenyl. More preferred $R^5$, $R^6$, $R^8$ and $R^9$ are hydrogen and $R^7$ is phenyl.

In a further embodiment of the compound of formula VI D is

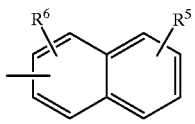

wherein $R^5$ and $R^6$ independently of each other are hydrogen or $C_{1-6}$ alkyl, preferably $R^5$ and $R^6$ are both hydrogen.

In the above compound of formula VI D is preferably (2-naphthyl), benzyloxy, or biphenyl-4-yl. More preferred (2-naphthyl) or biphenyl-4-yl, most preferred 2-naphthyl.

In one embodiment of the compound of formula VI E is

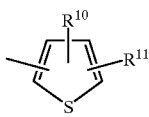

wherein $R^{10}$ and $R^{11}$ independently of each other are hydrogen or $C_{1-6}$ alkyl, preferably hydrogen.

In a further embodiment of the compound of formula VI E is

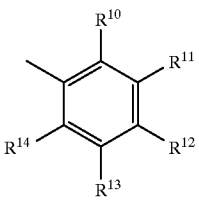

wherein $R^{10}$, $R^{11}$, $R^{12}$, $R^{13}$ and $R^{14}$ independently of each other are hydrogen, —$(CH_2)_v$—$NR^{15}SO_2R^{17}$, —$(CH_2)_v$—$NR^{15}COR^{16}$ or —$(CH_2)_v$—$OR^{17}$, wherein v is 0 or 1, preferably hydrogen or $C_{1-6}$ alkyl, preferably hydrogen, $R^{16}$ is hydrogen or $C_{1-6}$ alkyl optionally substituted with —$N(R^2)R^{27}$, wherein $R^{26}$ and $R^{27}$ independently of each other are hydrogen or $C_{1-6}$ alkyl, preferably $R^{16}$ is hydrogen or $C_{1-6}$ alkyl substituted with amino, $R^{17}$ is $C_{1-6}$ alkyl or phenyl optionally substituted with hydroxyl or phenyl, preferably methyl, $C_{1-6}$ alkyl substituted with hydroxyl, e.g.

—CH$_2$CH$_2$OH or -CH$_2$CH$_2$CH$_2$OH, or phenyl. In particular the phenylen moiety is ortho-substituted, however it may also be meta- or para-substituted and the invention is by no means limited hereto. In one embodiment, when R$^{10}$ or R$^{14}$ is —(CH$_2$)$_v$—NR$^{15}$SO$_2$R$^{17}$, v is 0, R$^{15}$ is hydrogen, and R$^{17}$ is C$_{1-6}$ alkyl or phenyl, preferably methyl or phenyl. In a second embodiment, when R$^{10}$ or R$^{14}$ is —(CH$_2$)$_v$—NR$^{15}$COR$^{16}$, v is 0, R$^{15}$ is hydrogen and R$^1$ is hydrogen or C$_{1-6}$ alkyl substituted with —NH$_2$, preferably aminomethyl. In a third embodiment, when R$^{10}$ or R$^{14}$ is —(CH$_2$)$_v$—OR$^{17}$, v is 0, and R$^{17}$ is C$_{1-6}$ alkyl substituted with hydroxyl, preferably —CH$_2$CH$_2$OH or —CH$_2$CH$_2$CH$_2$OH.

In the above compound of formula I E is preferably phenyl, 2-thienyl, 2-(2-hydroxyethoxy)phenyl, 2-(3-hydroxypropoxy)phenyl, biphenyl4-yl, 2-(aminoacetylamino)phenyl, 2-(phenylsulfonylamino)phenyl or 2-(methylsulfonylamino)phenyl. In one embodiment hereof E is phenyl, 2-thienyl or 2-(methylsulfonylamino)phenyl.

In one embodiment of the compound of formula VI G$^2$ is hydrogen or C$_{1-4}$ alkyl, preferably hydrogen, methyl or ethyl. In the above compound of formula VI G$^2$ is preferably hydrogen or methyl.

In one embodiment of the compound of formula VI R$^1$ is hydrogen or C$_{1-6}$ alkyl, preferably hydrogen or C$_{1-4}$ alkyl.

In the above compound of formula VI R$^1$ is preferably methyl.

In one embodiment of the compound of formula VI R$^2$ is hydrogen, —C(=O)—R$^{54}$ or C$_{1-6}$ alkyl, wherein R$^{54}$ is C$_{1-6}$ alkyl, preferably hydrogen, C$_{1-6}$ alkyl or —C(=O)—CH$_3$.

In the above compound of formula VI R$^2$ is preferably methyl, hydrogen, or acetyl, most preferred methyl.

In one embodiment of the compound of formula VI R$^3$ is hydrogen or C$_{1-6}$ alkyl, preferably hydrogen.

In one embodiment of the compound of formula VI R$^4$ is hydrogen or C$_{1-6}$ alkyl, preferably hydrogen.

In the above compound of formula VI R$^3$ and R$^4$ may be taken together to form =O.

In the above compound of formula VI b is preferably 0 or 1, most preferred 1.

A further embodiment of the compound of formula I relates to a compound of the general formula VII formula VII

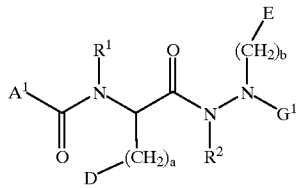

wherein

E is hydrogen, —O—(CH$_2$)$_l$—R$^{10a}$,

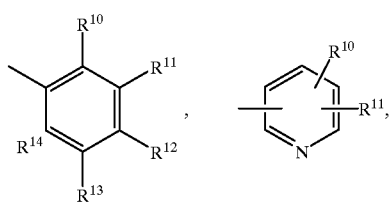

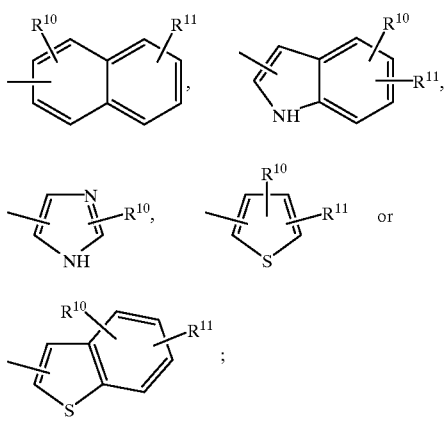

wherein R$^{10}$, R$^{11}$, R$^{12}$, R$^{13}$ and R$^{14}$ independently are hydrogen, halogen, aryl, C$_{1-6}$-alkyl, C$_{1-6}$-alkoxy;

R$^{10a}$ is hydrogen, aryl optionally substituted with halogen or C$_{1-6}$-alkyl, or C$_{1-6}$-alkyl optionally substituted with halogen or C$_{1-6}$-alkyl, and l is 0, 1, 2, or 3;

and A$^1$, D, G$^1$, R$^1$, R$^2$, a, and b are defined above;

or a pharmaceutically acceptable salt thereof.

In one embodiment of the compound of formula VII A$^1$ is

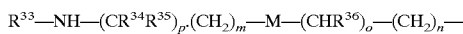

wherein R$^{33}$ is hydrogen or C$_{1-6}$ alkyl optionally substituted with hydroxyl, preferably hydrogen or methyl, most preferred hydrogen, R$^{34}$ and R$^{35}$ are independently of each other C$_{1-6}$ alkyl, preferably methyl, R$^{36}$ is hydrogen, M is —CR$^{37}$=CR$^{38}$— or —O—, wherein R$^{37}$ and R$^{38}$ are hydrogen or C$_{1-6}$ alkyl, preferably —CH=CH— or O, p is 1, m is 1, o is 0 or 1 and n is 0 or 1.

In another embodiment of the compound of formula VII A$^1$ is

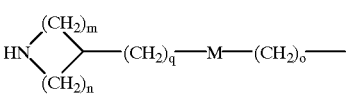

wherein M is —O— or —S—, preferably —O—, o is 0 or 1, preferably 1, q is 0, 1 or 2, preferably 1, and m+n is 3 or 4, preferably 3.

In a further embodiment of the compound of formula VII A$^1$ is

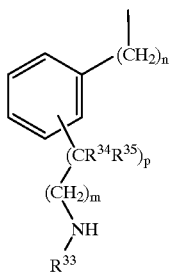

wherein $R^{33}$ is hydrogen or $C_{1-6}$ alkyl, preferably, hydrogen, $R^{34}$ and $R^{35}$ independently of each other are hydrogen or $C_{1-6}$ alkyl, preferably hydrogen or methyl, m is 0 or 1, n is 0 or 1, preferably 0 and p is 0 or 1. In particular the phenylen moiety is meta-substituted, however it might be ortho- or para-substituted as well and the invention is by no means limited hereto.

In the above compound of formula VII $A^1$ is preferably (1E)-4-amino-4-methylbut-1-enyl, (1E)-4-amino-4-methylpent-1-enyl (2-amino-2-methylpropyxy)methyl, ((2S)-pyrrolidin-2-yl)methoxymethyl, 4-piperidinyl, (1E)-4-((2R)-2-hydroxypropylamino)4-methylbut-1-enyl, (1E)-4-((2R)-2-hydroxypropylamino)4-methylpent-1-enyl, (1E)-4-methyl-4-methylaminopent-1-enyl, 3-(1-aminoethyl)phenyl or 3-(aminomethyl)phenyl. In one embodiment hereof $A^1$ is (1E)-4-amino-4-methylbut-1-enyl, (2-amino-2-methylpropyxy)methyl, ((2S)-pyrrolidin-2-yl)methoxymethyl, 4-piperidinyl, or (1E)-4-((2R)-2-hydroxypropylamino)-4-methylbut-1-enyl. In another embodiment hereof $A^1$ is (1E)-4-amino-4-methylpent-1-enyl, (2-amino-2-methylpropoxy)methyl or ((2S)-pyrrolidin-2-yl)methoxymethyl.

In one embodiment of the compound of formula VII D is

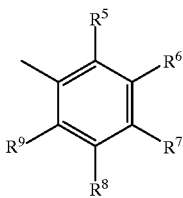

wherein $R^5$, $R^6$, $R^7$, $R^8$ and $R^9$ independently of each other are hydrogen or aryl, prefarably hydrogen or phenyl. More preferred $R^5$, $R^6$, $R^8$ and $R^9$ are hydrogen and $R^7$ is phenyl.

In a further embodiment of the compound of formula VII D is

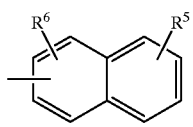

wherein $R^5$ and $R^6$ independently of each other are hydrogen or $C_{1-6}$ alkyl, preferably $R^5$ and $R^6$ are both hydrogen.

In the above compound of formula VII D is preferably (2-naphthyl), benzyloxy, or biphenyl-4-yl. More preferred (2-naphthyl) or biphenyl-4-yl, most preferred 2-naphthyl.

In one embodiment of the compound of formula VII E is

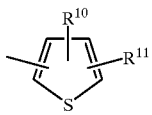

wherein $R^{10}$ and $R^{11}$ independently of each other are hydrogen or $C_{1-6}$ alkyl, preferably hydrogen.

In a further embodiment of the compound of formula VII E is

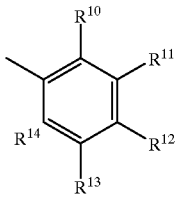

wherein $R^{10}$, $R^{11}$, $R^{12}$, $R^{13}$ and $R^{14}$ independently of each other are hydrogen, $-(CH_2)_v-NR^{15}SO_2R^{17}$, $-(CH_2)_v-NR^{15}COR^{16}$ or $-(CH_2)_v-OR^{17}$, wherein v is 0 or 1, preferably 0, $R^{15}$ is hydrogen or $C_{1-6}$ alkyl, preferably hydrogen, $R^{16}$ is hydrogen or $C_{1-6}$ alkyl optionally substituted with $-N(R^{26})R^{27}$, wherein $R^{26}$ and $R^{27}$ independently of each other are hydrogen or $C_{1-6}$ alkyl, preferably $R^{16}$ is hydrogen or $C_{1-6}$ alkyl substituted with amino, $R^{17}$ is $C_{1-6}$ alkyl or phenyl optionally substituted with hydroxyl or phenyl, preferably methyl, $C_{1-6}$ alkyl substituted with hydroxyl, e.g. $-CH_2CH_2OH$ or $-CH_2CH_2CH_2OH$, or phenyl. In particular the phenylen moiety is ortho-substituted, however it may also be meta- or para-substituted and the invention is by no means limited hereto. In one embodiment, when $R^{10}$ or $R^{14}$ is $-(CH_2)_v-NR^{15}SO_2R^7$, v is 0, $R^{15}$ is hydrogen, and $R^{17}$ is $C_{1-6}$ alkyl or phenyl, preferably methyl or phenyl. In a second embodiment, when $R^{10}$ or $R^{14}$ is $-(CH_2)_v-NR^{15}COR^{16}$, v is 0, $R^{15}$ is hydrogen and $R^{16}$ is hydrogen substituted with $-NH_2$, preferably aminomethyl. In a third embodiment, when $R^{10}$ or $R^{14}$ is $-(CH_2)_v-OR^{17}$, v is 0, and $R^{17}$ is $C_{1-6}$ alkyl substituted with hydroxyl, preferably $-CH_2CH_2OH$ or $-CH_2CH_2CH_2OH$.

In the above compound of formula VII E is preferably phenyl, 2-thienyl, 2-(2-hydroxyethoxy)phenyl, 2-(3-hydroxypropoxy)phenyl, biphenyl-4-yl, 2-(aminoacetylamino)phenyl, 2-(phenylsulfonylamino)phenyl or 2-(methylsulfonylamino)phenyl. In one embodiment hereof E is preferably phenyl, or 2-thienyl, most preferred phenyl.

In one embodiment of the compound of formula VII $G^1$ is hydrogen or $-CONR^{39}R^{40}$, wherein $R^{39}$ and $R^{40}$ independently of each other are hydrogen or $C_{1-6}$ alkyl, preferably hydrogen, methyl or ethyl.

In the above compound of formula VII $G^1$ is preferably methylcarbamoyl or ethylcarbamoyl, most preferred ethylcarbamoyl.

In one embodiment of the compound of formula VII $R^1$ is $C_{1-6}$ alkyl, preferably hydrogen or $C_{1-4}$ alkyl. In the above compound of formula VII $R^1$ is preferably methyl.

In one embodiment of the compound of formula VII $R^2$ is hydrogen, $-C(=O)-R^{54}$ or $C_{1-6}$ alkyl, wherein $R^{54}$ is $C_{1-6}$ alkyl, preferably hydrogen, $C_{1-6}$ alkyl or $-C(=O)-CH_3$.

In the above compound of formula VII $R^2$ is preferably methyl, hydrogen, or acetyl, more preferred methyl or hydrogen, most preferred hydrogen.

In the above compound of formula VII a is preferably 1.

In the above compound of formula VII b is preferably 1.

The compounds of formulas I-VII comprise any optical isomers thereof, in the form of separated, pure or partially purified optical isomers or racemic mixtures thereof.

Preferred compounds of the invention are:

1-((2R)-2-(N-((2E)-5-amino-5-methylhex-2-enoyl)-N-methylamino)-3-(2-naphthyl)propionyl)-2-benzyl-4-ethylsemicarbazide:

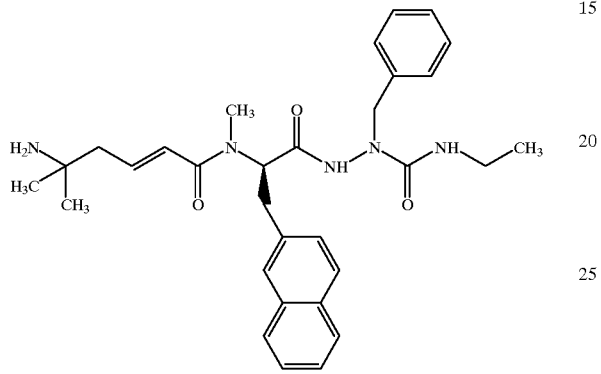

(2R)-2-(N-((2E)-5-Amino-5-methylhex-2-enoyl)-N-methylamino)-3-(2-naphthyl)propionic acid N-methyl-N-phenethylamide:

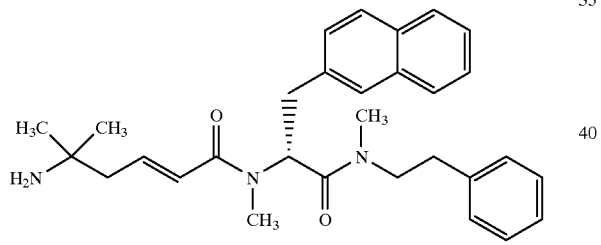

1-((2R)-2-(N-(2-(((2S)-pyrrolidin-2yl)methoxy)acetyl)-N-methylamino)-3-(2-naphthyl)propionyl)-2-benzyl-4-ethylsemicarbazide:

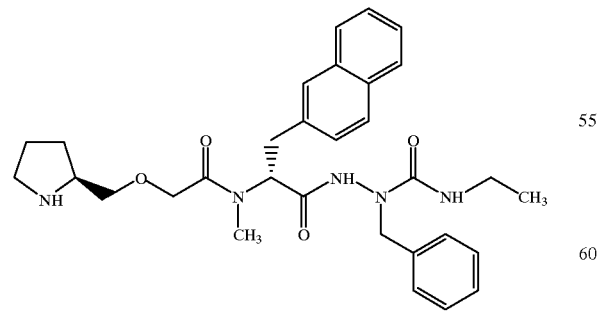

1-((2R)-2-(N-((2-amino-2-methylpropoxy)acetyl)-N-methylamino)-3-(2-naphthyl)propionyl)-2-benzyl-4-ethylsemicarbazide:

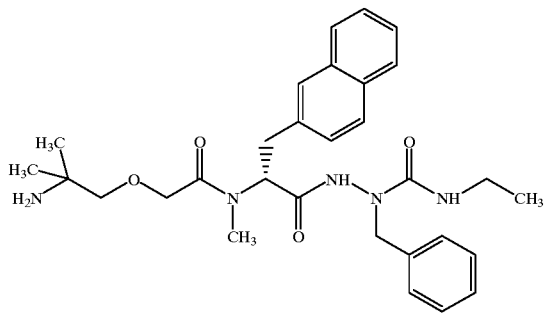

(2R)-2-(N-((2E)-5-Amino-5-methylhex-2-enoyl)-N-methylamino)-3-(2-naphthyl)propionic acid N-methyl-N-(2-(2-(methylsulfonylamino)phenyl)ethyl)amide:

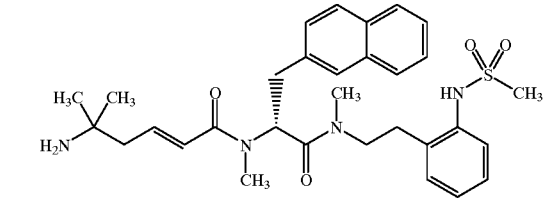

(2R)-2-(N-((2E)-5-Amino-5-methylhex-2-enoyl)-N-methylamino)-3-(2-naphthyl)propionic acid N-methyl-N-(2-(2-thienyl)ethyl)amide:

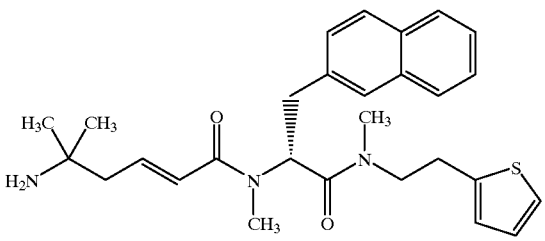

(2R)-2-((5R)-4-((2E)-5-Amino-5-methylhex-2-enoyl)-5-(2-naphthyl)methyl-2-oxopiperazin-1-yl)-N-methyl-3-phenylpropionamide:

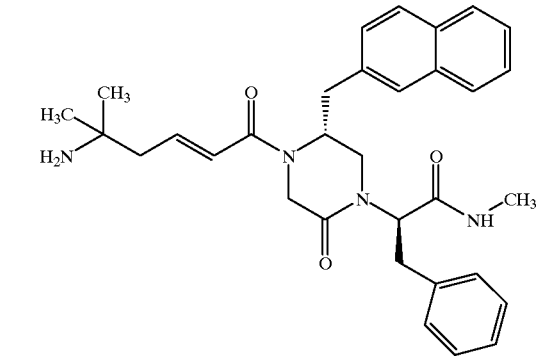

(2R)-2-(N-((2E)-5-((2R)-2-hydroxypropylamino)-5-methylhex-2-enoyl)-N-methylamino)-N-methyl-3-(2-naphthyl)-N-phenethylpropionamide:

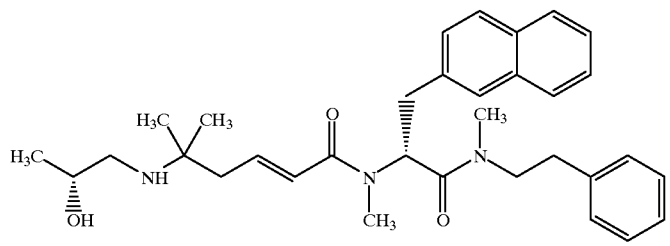

(2E)-5-Amino-5-methylhex-2-enoic acid N-((1R)-2-(N-acetyl-N-((1R)-1-(methylcarbamoyl)-2-phenylethyl)amino)-1-((2-naphthyl)methyl)ethyl)amide:

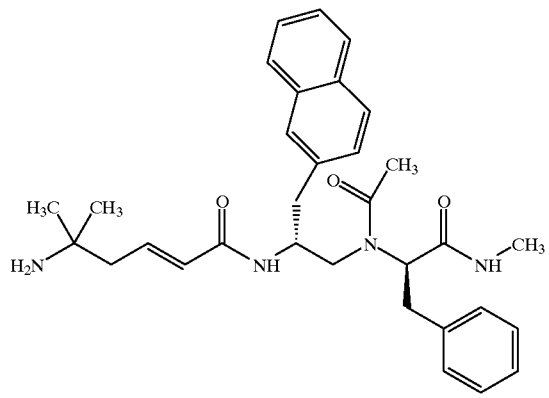

(2E)-5-Amino-5-methyl-N-methyl-N-((1R)-1-(N-methyl-N-(2-(2-thienyl)ethyl)carbamoyl)-2-(2-naphthyl)ethyl)hex-2-enamide

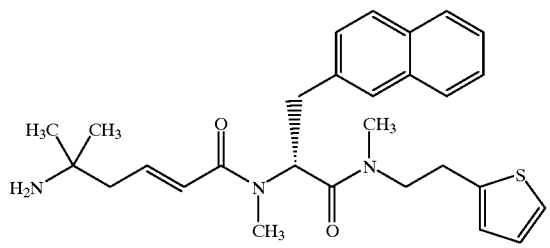

(2E)-5-Methyl-5-(methylamino)-N-methyl-N-((1R)-1-(N-methyl-N-(2-(2-thienyl)ethyl)carbamoyl)-2-(2-naphthyl)ethyl)hex-2-enamide

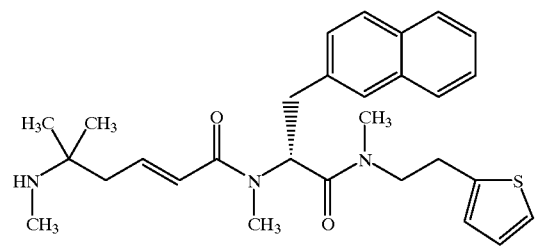

(2E)-5-Amino-5-methylhex-2-enoic acid N-methyl-N-((1R)-1-(N-methyl-N-(3-phenylpropyl)carbamoyl)-2-(2-naphthyl)ethyl)amide

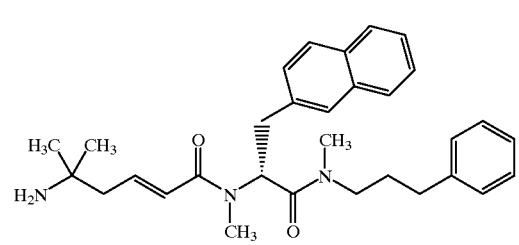

(2R)-2-(N-(3-(1-Aminoethyl)benzoyl)-N-methylamino)-N-methyl-3-(2-naphthyl)-N-(2-(2-thienyl)ethyl)propionamide

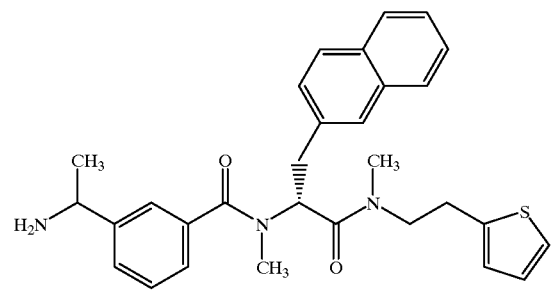

(2E)-5-Amino-5-methylhex-2-enoic acid N-((1R)-2-(1,2,3,4-tetrahydroisoquinolin-2-yl)-1-((2-naphthyl)methyl)-2-oxoethyl)-N-methylamide

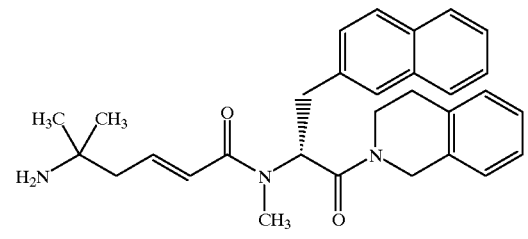

(2E)-5-Methyl-N-methyl-5-(methylamino)-N-((1R)-1-(N-methyl-N-phenethylcarbamoyl)-2-(2-naphthyl)ethyl)hex-2-enamide

31

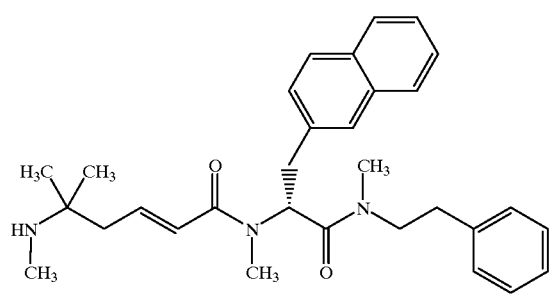

(2R)-2-(N-((2E)-5-Amino-5-methylhex-2-enoyl)-N-methylamino)-N-(2-(2-(2-hydroxyethoxy)phenyl)ethyl)-N-methyl-3-(2-naphthyl)propionamide

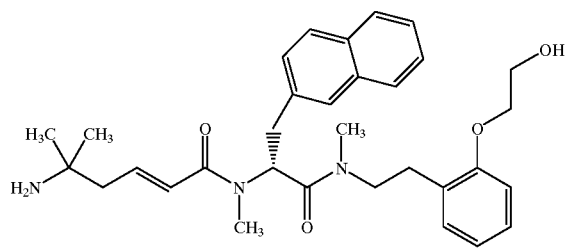

(2R)-2-(N-((2E)-5-Amino-5-methylhex-2-enoyl)-N-methylamino)-N-methyl-3-(2-naphthyl)-N-(2-(2-methylsulfonylaminophenyl)ethyl)propionamide

32

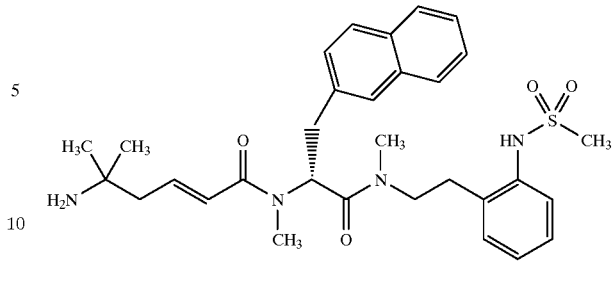

(2E)-5-Amino-N-((1R)-2-(biphenyl-4-yl)-1-(N-(2-(2-thienyl)ethyl)-5-methyl-N-methylhex-2-enamide

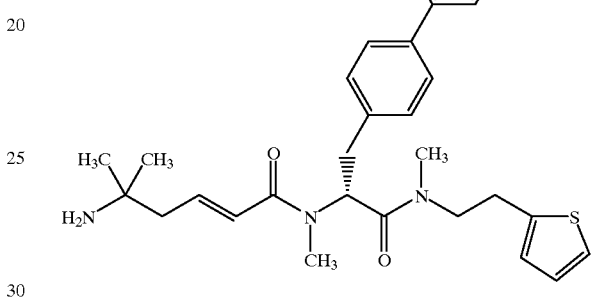

(2E)-N-((1R)-1-(N-(2-(2-(2-Hydroxyethoxy)phenyl)ethyl)-N-methylcarbamoyl)-2-(2-naphthyl)ethyl)-N-methyl-5-methyl-5-(methylamino)hex-2-enamide

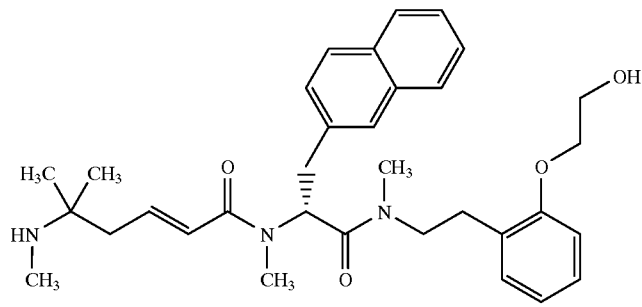

3-Aminomethyl-N-[(1R)-1-(N-{2-[2-(2-hydroxyethoxy)phenyl]ethyl}-N-methylcarbamoyl)-2-(2-naphthyl)ethyl]benzamide

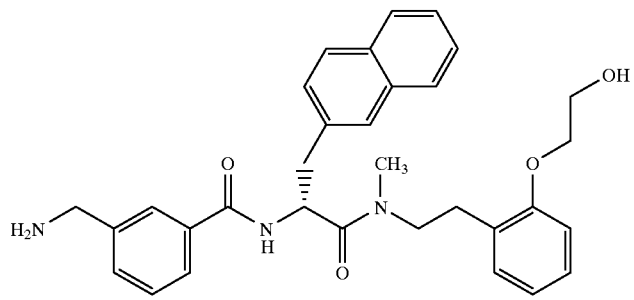
(2E)-5-Amino-5-methylhex-2-enoic acid N-((1R)-1-(N-(2-(2-(2-hydroxyethoxy)phenyl)ethyl-N-methylcarbomoyl)-2-(2-naphthyl)ethyl)amide
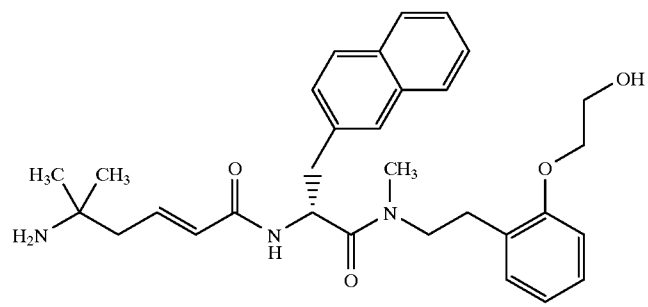
(2E)-5-Amino-5-methylhex-2-enoic acid N-((1R)-1-{N-[2-(2-(benzensulfonylamino)phenyl)ethyl]-N-methylcarbamoyl}-2-(2-naphthyl)ethyl)-N-methylamide
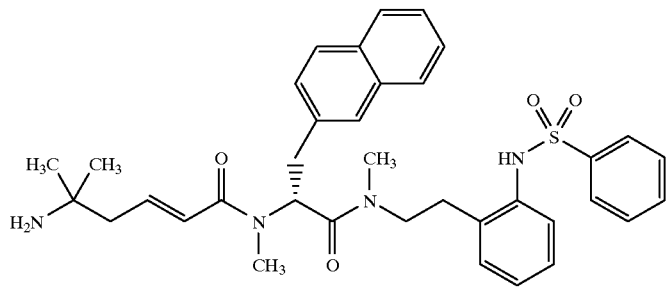
2-Amino-N-(2-(2-(N-((2E)-5-Amino-5-methylhex-2-enoyl)-N-methylamino)-3-(2-naphthyl)propionyl)-N-methylamino)ethyl)phenyl)acetamide

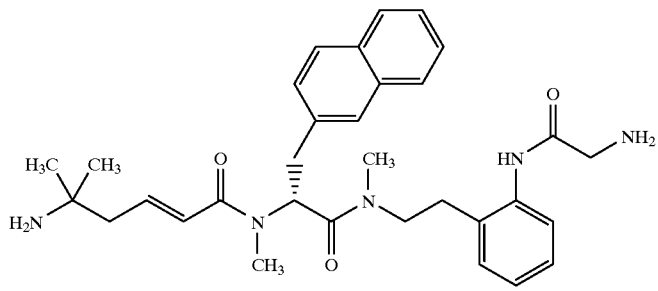
(2R)-2-(N-((2E)-5-Amino-5-methylhex-2-enoyl)-N-methylamino)-N-(2-(2-(3-hydroxypropoxy)phenyl)ethyl)-N-methyl-3-(2-naphthyl)propionamide
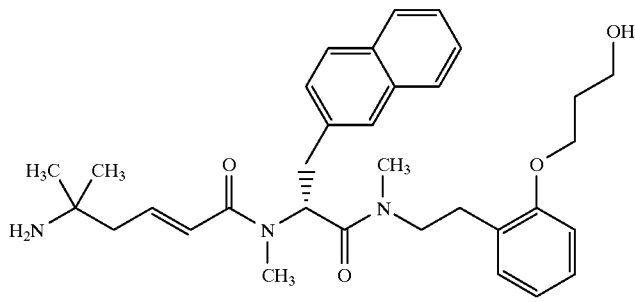
3-Aminomethyl-N-[(1R)-1-(N-{2-[2-(2-hydroxyethoxy)phenyl]ethyl}-N-methylcarbamoyl)-2-(2-naphthyl)ethyl]benzamide
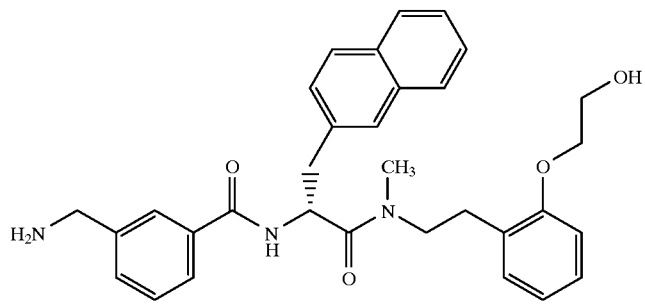
(2E)-5-Amino-5-methylhex-2-enoic acid N-((1R)-1-(N-(2-(2-(2-hydroxyethoxy)phenyl)ethyl)-N-methylcarbomoyl)-2-(2-naphthyl)ethyl)-N-methylamide

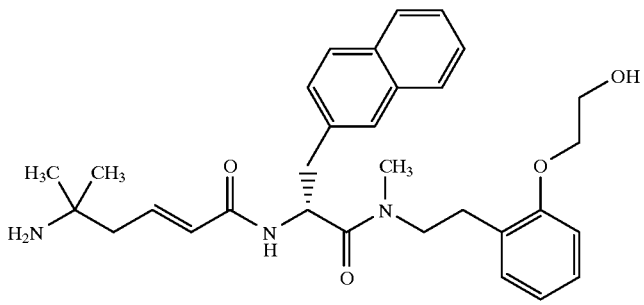

(3R)-4-((2E)-5-Amino-5-methyl hex-2-enoyl)-3-((2-naphthyl)methyl)-1-phenethylpiperanzin-2-one

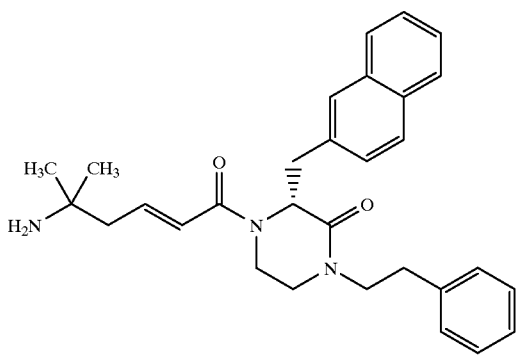

Throughout the present specification compounds of formula I are also intended to comprise compounds of formula II, III, IV, V, VI, and VII, and thus, a reference to formula I is also a reference to any one of formula II, III, IV, V, VI, and VII.

It is believed that compounds of formula I exhibit an improved resistance to proteolytic degradation by enzymes compared to that of the peptides suggested in the prior literature, due to the lack of natural peptide bonds. The increased resistance to proteolytic degradation combined with the reduced size of the compounds of the invention in comparison with known growth hormone releasing peptides is expected to improve their bioavailability compared to that of the peptides suggested in the prior literature.

In the above structural formulas and throughout the present specification, the following terms have the indicated meanings:

The $C_{1-6}$ alkyl groups specified above are intended to include those alkyl groups of the designated length in either a linear or branched or cyclic configuration. Examples of linear alkyl are methyl, ethyl, propyl, butyl, pentyl, and hexyl. Examples of branched alkyl are isopropyl, sec-butyl, tert-butyl, isopentyl, and isohexyl. Examples of cyclic alkyl are $C_{3-6}$-cycloalkyl such as cyclopropyl, cyclobutyl, cyclopentyl and cyclohexyl.

The $C_{1-6}$-alkoxy groups specified above are intended to include those alkoxy groups of the designated length in either a linear or branched or cyclic configuration. Examples of linear alkyloxy are methoxy, ethoxy, propoxy, butoxy, pentoxy, and hexoxy. Examples of branched alkoxy are isopropoxy, sec-butoxy, tert-butoxy, isopentoxy, and isohexoxy. Examples of cyclic alkoxy are cyclopropyloxy, cyclobutyloxy, cyclopentyloxy and cyclohexyloxy.

In the present context, the term "aryl" is intended to include aromatic rings, such as carbocyclic and heterocyclic aromatic rings selected from the group consisting of phenyl, naphthyl, pyridyl, 1-H-tetrazol-5-yl, thiazolyl, imidazolyl, indolyl, pyrimidinyl, thiadiazolyl, pyrazolyl, oxazolyl, isoxazolyl, oxadiazolyl, thiopheneyl, quinolinyl, pyrazinyl, or isothiazolyl, optionally substituted by one or more $C_{1-6}$-alkyl, $C_{1-6}$-alkoxy, halogen, amino or aryl. Aryl is preferably phenyl, thienyl, imidazolyl, oxadiazolyl, pyridyl, indolyl, quinolinyl or naphthyl optionally substituted with halogen, amino, hydroxy, $C_{1-6}$-alkyl or $C_{1-6}$-alkoxy.

The term "halogen" is intended to include Cl, F, Br and I.

The compounds of the present invention may have one or more asymmetric centers and it is intended that stereoisomers, as separated, pure or partially purified stereoisomers or racemic mixtures thereof are included in the scope of the invention. The compounds of the present invention may optionally be on a pharmaceutically acceptable salt form such as the pharmaceutically acceptable acid addition salts of compounds of formula I which include those prepared by reacting the compound of formula I with an inorganic or organic acid such as hydrochloric, hydrobromic, sulfuric, acetic, phosphoric, lactic, maleic, phthalic, citric, glutaric, gluconic, methanesulfonic, salicylic, succinic, tartaric, toluenesulfonic, trifluoracetic, sulfamic or fumaric acid.

The compounds of formula I may be administered in pharmaceutically acceptable acid addition salt form or, where appropriate, as a alkali metal or alkaline earth metal or lower alkylammonium salt. Such salt forms are believed to exhibit approximately the same order of activity as the free base forms.

In another aspect, the present invention relates to a pharmaceutical composition comprising, as an active ingredient, a compound of the general formula I or a pharmaceutically acceptable salt thereof together with a pharmaceutically acceptable carrier or diluent.

Pharmaceutical compositions containing a compound of the present invention may be prepared by conventional techniques, e.g. as described in *Remington's Pharmaceutical Sciences*, 1985. The compositions may appear in conventional forms, for example capsules, tablets, aerosols, solutions, suspensions or topical applications.

The pharmaceutical carrier or diluent employed may be a conventional solid or liquid carrier. Examples of solid carriers are lactose, terra alba, sucrose, cyclodextrin, talc, gelatin, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water.

Similarly, the carrier or diluent may include any sustained release material known in the art, such as glyceryl monostearate or glyceryl distearate, alone or mixed with a wax.

If a solid carrier is used for oral administration, the preparation may be tabletted, placed in a hard gelatin capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatin capsule or sterile injectable liquid such as an aqueous or non-aqueous liquid suspension or solution.

A typical tablet which may be prepared by conventional tabletting techniques may contain:

| Core: | |
| --- | --- |
| Active compound (as free compound or salt thereof) | 100 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | |
| Coating: | |
| HPMC approx. | 9 mg |
| *Mywacett 9-40 T approx. | 0.9 mg |

*Acylated monoglyceride used as plasticizer for film coating.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

Generally, the compounds of the present invention are dispensed in unit dosage form comprising 50–200 mg of active ingredient together with a pharmaceutically acceptable carrier per unit dosage. The dosage of the compounds according to this invention is suitably 0.1–500 mg/day, e.g. from about 5 to about 50 mg, such as about 10 mg per dose, when administered to patients, e.g. humans, as a drug.

It has been demonstrated that compounds of the general formula I possess the ability to release endogenous growth hormone in vivo. The compounds may therefore be used in the treatment of conditions which require increased plasma growth hormone levels such as in growth hormone deficient humans or in elderly patients or livestock.

Thus, in a particular aspect, the present invention relates to a pharmaceutical composition for stimulating the release of growth hormone from the pituitary, the composition comprising, as an active ingredient, a compound of the general formula I or a pharmaceutically acceptable salt thereof together with a pharmaceutically acceptable carrier or diluent.

In a further aspect, the present invention relates to a method of stimulating the release of growth hormone from the pituitary, the method comprising administering to a subject in need thereof an effective amount of a compound of the general formula I or a pharmaceutically acceptable salt thereof.

In a still further aspect, the present invention relates to the use of a compound of the general formula I or a pharmaceutically acceptable salt thereof for the preparation of a medicament for stimulating the release of growth hormone from the pituitary.

To those skilled in the art, it is well known that the current and potential uses of growth hormone in humans are varied and multitudinous. Thus, compounds of formula I can be administered for purposes stimulating release of growth hormone from the pituitary and would then have similar effects or uses as growth hormone itself. The uses of growth hormone may be summarized as follows: stimulation of growth hormone release in the elderly; prevention of catabolic side effects of glucocorticoids, prevention and treatment of osteoporosis, treatment of NIDDM, stimulation of the immune system, acceleration of wound healing, accelerating bone fracture repair, treatment of growth retardation, treating renal failure or insufficiency resulting from growth retardation, treatment of physiological short stature including growth hormone deficient children and short stature associated with chronic illness, treatment of obesity and growth retardation associated with obesity, treatment of anorexia, treating growth retardation associated with the Prader-Willi syndrome and Turner's syndrome; accelerating the recovery and reducing hospitalization of burn patients; treatment of intrauterine growth retardation, skeletal dysplasia, hypercortisolism and Cushing's syndrome; induction of pulsatile growth hormone release; replacement of growth hormone in stressed patients, treatment of osteochondrodysplasias, Noonan's syndrome, schizophrenia, depressions, Alzheimer's disease, delayed wound healing and psychosocial deprivation, treatment of pulmonary dysfunction and ventilator dependency, attenuation of protein catabolic responses after major surgery, reducing cachexia and protein loss due to chronic illness such as cancer or AIDS; treatment of hyperinsulinemia including nesidioblastosis, adjuvant treatment for ovulation induction; to stimulate thymic development and prevent the age-related decline of thymic function, treatment of immunosuppressed patients, improvement in muscle strength, mobility, maintenance of skin thickness, metabolic homeostasis, renal homeostasis in the frail elderly, stimulation of osteoblasts, bone remodelling and cartilage growth, stimulation of the immune system in companion animals and treatment of disorder of aging in companion animals, growth promoter in livestock and stimulation of wool growth in sheep.

For the above indications the dosage will vary depending on the compound of formula I employed, on the mode of administration and on the therapy desired. However, generally dosage levels between 0.0001 and 100 mg/kg body weight daily are administered to patients and animals to obtain effective release of endogenous growth hormone. Usually, dosage forms suitable for oral, nasal, pulmonal or transdermal administration comprise from about 0.0001 mg to about 100 mg, preferably from about 0.001 mg to about 50 mg of the compounds of formula I admixed with a pharmaceutically acceptable carrier or diluent.

Optionally, the pharmaceutical composition of the invention may comprise a compound of formula I combined with one or more compounds exhibiting a different activity, e.g., an antibiotic or other pharmacologically active material.

The route of administration may be any route which effectively transports the active compound to the appropriate or desired site of action, such as oral, nasal, pulmonary, transdermal or parenteral, the oral route being preferred.

Apart from the pharmaceutical use of the compounds of formula 1, they may be useful in vitro tools for investigating the regulation of growth hormone release.

Compounds of formula I may also be useful in vivo tools for evaluating the growth hormone releasing capability of the pituitary. For example, serum samples taken before and after administration of these compounds to humans can be assayed for growth hormone. Comparison of the growth hormone in each serum sample would directly determine the ability of the patients pituitary to release growth hormone.

Compounds of formula I may be administered to commercially important animals, such as cows, sheeps, pigs, goats, etc. to increase their rate and extent of growth, and to increase milk production.

A further use of growth hormone secretagogue compounds of formula I is in combination with other secretagogues such as GHRP (2 or 6), GHRH and its analogues, growth hormone and its analogues or somatomedins including IGF-1 and IGF-2.

Pharmacological Methods

Compounds of formula I may be evaluated in vitro for their efficacy and potency to release growth hormone in rat pituitary primary cultures.

The isolation of rat pituitary cells is a modification of O. Sartor et al., *Endocrinology* 116, 1985, pp. 952–957. Male albino Sprague-Dawley rats (250+/−25 grams) were purchased from Møllegaard, Lille Skensved, Denmark. The rats were housed in group cages (four animals/cage) and placed in rooms with 12 hour light cycle. The room temperature varied from 19–24° C. and the humidity from 30–60%.

The rats were decapitated and the pituitaries dissected. The neurointermediate lobes were removed and the remaining tissue was immediately placed in icecold isolation buffer (Gey's medium (Gibco 041-04030) supplemented with 0.25% D-glucose, 2% non-essential amino acids (Gibco 043-01140) and 1% bovine serum albumine (BSA) (Sigma A-4503)). The tissue was cut into small pieces and transferred to isolation buffer supplemented with 3.8 mg/ml of trypsin (Worthington #3707 TRL-3) and 330 mg/ml of DNase (Sigma D-4527). This mixture was incubated at 70 rotations/min for 35 min at 37° C. in a 95/5% atmosphere of $O_2/CO_2$. The tissue was then washed three times in the above buffer. Using a standard pasteur pipette, the tissue was then aspirated into single cells. After dispersion, cells were filtered through a nylon filter (160 mm) to remove undigested tissue. The cell suspension was washed 3 times with isolation buffer supplemented with trypsin inhibitor (0.75 mg/ml, Worthington #2829) and finally resuspended in culture medium; DMEM (Gibco 041-01965) supplemented with 25 mM HEPES (Sigma H-3375), 4 mM glutamine (Gibco 043-05030H), 0.075% sodium bicarbonate (Sigma S-8875), 0.1% non-essential amino acid, 2.5% fetal calf serum (FCS, Gibco 011-06290), 3% horse serum (Gibco 034-06050), 10% fresh rat serum, 1 nM $T_3$ (Sigma T-2752) and 40 mg/L dexamethasone (Sigma D4902) pH 7.3, to a density of $2 \times 10^5$ cells/ml. The cells were seeded into microtiter plates (Nunc, Denmark), 200 ml/well, and cultured for 3 days at 37° C. and 8% $CO_2$.

Compound testing

After culturing, the cells were washed twice with stimulation buffer (Hanks Balanced Salt Solution (Gibco 041-04020) supplemented with 1% BSA (Sigma A-4503), 0.25% D-glucose (Sigma G-5250) and 25 mM HEPES (Sigma H-3375) pH 7.3) and preincubated for 1 hour at 37° C. The buffer was exchanged with 90 ml stimulation buffer (37° C.). Ten ml test compound solution was added and the plates were incubated for 15 min at 37° C. and 5% $CO_2$. The medium was decanted and analyzed for GH content in an rGH SPA test system.

All compounds were tested in doses ranging from 10 pM to 100 mM. A dose-response relation was constructed using the Hill equation (Fig P, Biosoft). The efficacy (maximal GH released, $E_{max}$) was expressed in % of the $E_{max}$ of GHRP-6. The potency ($EC_{50}$) was determined as the concentration inducing half maximal stimulation of the GH release.

Compounds of formula I may be evaluated for their metabolic stability.

Compounds were dissolved at a concentration of 1 mg/ml in water. 25 ml of this solution is added to 175 ml of the respective enzyme-solution (resulting in an enzyme:substrate ratio (w/w) of approximately 1:5). The solution is left at 37° C. overnight. 10 ml of the various degradation solutions is analyzed against a corresponding zero-sample using flow injection electrospray mass spectrometry (ESMS) with selected ion monitoring of the molecular ion. If the signal has decreased more than 20% compared to the zero-sample, the remainder of the solution is analyzed by HPLC and mass spectrometry in order to identify the extent and site(s) of degradation precisely.

Several standard peptides (ACTH 4-10, Angiotensin 1-14 and Glucagon) have been included in the stability tests in order to verify the ability of the various solutions to degrade peptides.

Standard peptides (angiotensin 1-14, ACTH 4-10 and glucagon) were purchased from Sigma, Mo., USA)

Enzymes (trypsin, chymotrypsin, elastase aminopeptidase M and carboxypeptidase Y and B) were all purchased from Boehringer Mannheim GmbH (Mannheim, Germany)

Pancreatic enzyme mix: trypsin, chymotrypsin and elastase in 100 mM ammoniumbicarbonate pH 8.0 (all concentrations 0.025 mg/ml).

Carboxypeptidase mix: carboxypeptidase Y and B in 50 mM ammoniumacetate pH 4.5 (all concentrations 0.025 mg/ml).

Aminopeptidase M solution: aminopeptidase M (0.025 mg/ml) in 100 mM ammoniumbicarbonate pH 8.0

Mass spectrometric analysis was performed using two different mass spectrometers. A Sciex API III triple quadrupole LC-MS instrument (Sciex instruments, Thornhill, Ontario) equipped with an electrospray ion-source and a Bio-Ion 20 time-of-flight Plasma Desorption instrument (Bio-Ion Nordic AB, Uppsala, Sweden).

Quantification of the compounds (before and after degradation) was done on the API III instrument using single ion monitoring of the molecular ion in question with flow injection of the analyte. The liquid flow (MeOH:water 1:1) of 100 ml/min was controlled by an ABI 140B HPLC unit (Perkin-Elmer Applied Biosystems Divisions, Foster City, Calif.). The instrument parameters were set to standard operation conditions, and SIM monitoring was performed using the most intense molecular ion (in most cases this corresponded to the doubly charged molecular ion).

Identification of degradation products furthermore involved the use of plasma desorption mass pectrometry (POMS) with sample application on nitrocellulose coated targets and standard instrumental settings. The accuracy of the hereby determined masses is generally better than 0.1%.

Separation and isolation of degradation products was done using a HY-TACH C-18 reverse phase 4.6×105 mm HPLC column (Hewlett-Packard Company, Palo Alto, Calif.) with a standard acetonitril: TFA separation gradient. The HPLC system used was HP1090M (Hewlett-Packard Company, Palo Alto, Calif.).

| Peptide derivative Standards | MW/SIM ion (amu) | Carboxy-peptidase mix | Pan. enzyme mix |
|---|---|---|---|
| ACTH 4-10 | 1124.5/562.8 | + | − |
| Glucagon | 3483/871.8 | − | − |
| Insulin (B23-29) | 859.1/430.6 | | |
| Angiotensin 1-14 | 1760.1/881.0 | − | − |
| GHRP-2 | 817.4/409.6 | − | − |

43

-continued

| Peptide derivative Standards | MW/SIM ion (amu) | Carboxy- peptidase mix | Pan. enzyme mix |
|---|---|---|---|
| GHRP-6 | 872.6/437.4 | – | – |

+: Stable (less than 20% decrease in SIM signal after 24 h in degradation solution)
–: Unstable (more than 20% decrease in SIM signal after 24 h in degradation solution)

Any novel feature or combination of features described herein is considered essential to this invention.

EXAMPLES

The process for preparing compounds of formula I and preparations containing them is further illustrated in the following examples, which however, are not to be construed as limiting.

The structures of the compounds are confirmed by either elemental analysis (MA) nuclear magnetic resonance- (NMR) or mass spectrometry (MS). NMR shifts (d) are given in parts per million (ppm) and only selected peaks are given mp is melting point and is given in ° C. Column chromatography was carried out using the technique described by W. C. Still et al, J. Org. Chem. 1978, 43, 2923–2925 on Merck silica gel 60 (Art 9385). Compounds used as starting materials are either known compounds or compounds which can readily be prepared by methods known per se.

Abbrevations:
 TLC: thin layer chromatography
 DMSO: dimethylsulfoxide
 min: minutes
 h: hours HPLC-Analysis:
Method A1.

The RP-analysis was performed using UV detections at 214, 254, 276, and 301 nm on a 218TP54 4.6 mm×250 mm 5 mm C-18 silica column (The Seperations Group, Hesperia), which was eluted at 1 mL/min at 42° C. The column was equilibrated with 5% acetonitrile in a buffer consisting of 0.1M ammonium sulfate, which was adjusted to pH 2.5 with 4M sulfuric acid. after injection the sample was eluted by a gradient of 5% to 60% acetonitrile in the same buffer during 50 min.

Example 1

(2R)-2-(N-((2E)-5-Amino-5-methylhex-2-enoyl)-N-methylamino)-3-(2-naphthyl)propionic acid N-methyl-N-phenethylamide

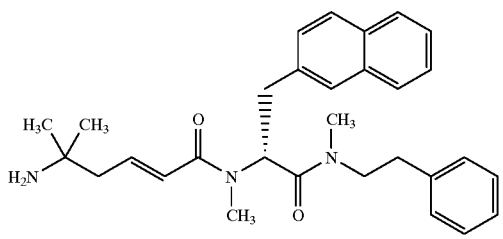

N-Methyl-N-((1R)-1-(N-methyl-N-phenethylcarbamoyl)-2-(2-naphthyl)ethyl)carbamic acid tert-butylester

44

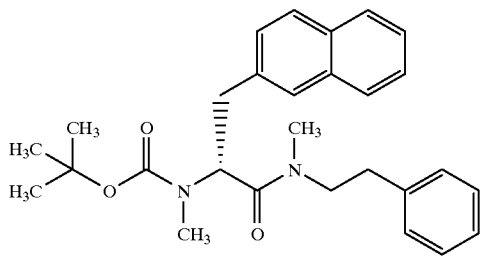

(2R)-2-(N-tert-Butoxycarbonyl-N-methylamino)-3-(2-naphthyl)propionic acid (1.40 g, 4.3 mmol) was dissolved in N,N-dimethylformamide (5 ml) and dichloromethane (5 mL). Hydroxy-7-azabenzotriazole (0.59 g, 4.3 mmol) was added as a solid. The solution was cooled to 0° C. N-(3-dimethylaminopropyl)-N'-ethylcarbodiimide hydrochloride (0.99 g, 5.2 mmol) was added. The solution was stirred for 20 min at 0° C. N-Methyl-N-phenethylamine (0.86 ml, 6.0 mmol) was added. The solution was stirred for 16 h, while it was warming up to room temperature. It was diluted with water (300 ml) and ethyl acetate (150 ml). 10% sodium hydrogen sulfate solution (80 ml) was added. The phases were seperated. The aqueous phase was extracted with ethyl acetate (4×50 ml). The combined organic layers were washed with saturated sodium hydrogen carbonate solution (200 ml) and dried over magensium sulfate. The solvent was removed in vacuo. The crude product was purified by flash chromatography on silica (90 g), using ethyl acetate/heptane 1:1 as eluent to give 1.89 g of N-methyl-N-((1R)-1-(N-methyl-N-phenethylcarbamoyl)-2-(2-naphthyl)ethyl) carbamic acid tert-butylester.

$^1$H-NMR (CDCl$_3$): d 1.01, 1.09, 1.25, and 1.30 (all s, together 9 H); 2.60–3.85 (m, 12 H); 4.75, 5.03, 5.31, and 5.37 (all dd, together 1 H); 7.00–7.85 (m, 12 H).

(2R)-2-(Methylamino)-3-(2-naphthyl)propionic acid N-methyl-N-phenethylamide

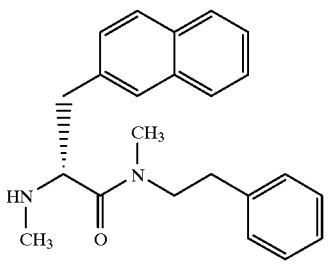

N-Methyl-N-((1R)-1-(N-methyl-N-phenethylcarbamoyl)-2-(2-naphthyl)ethyl)carbamic acid tert-butylester (1.84 g, 4.12 mmol) was dissolved in dichloromethane (6 ml). The solution was cooled to 0° C. Trifluoroacetic acid (6 ml) was added. The solution was stirred for 10 min at 0° C. The solvent was removed in vacuo at 20° C. The residue was dissolved in dichloromethane (100 ml) and the solvent was removed in vacuo. This latter procedure was repeated two times. The crude product was purified by flash chromatography on silica (70 g), using dichloromethane/methanol/25% aqueous ammonia (100:10:1) as eluent, to give 350 mg of (2R)-2-(methylamino)-3-(2-naphthyl)propionic acid N-methyl-N-phenethylamide.

$^1$H-NMR (CDCl$_3$): d 1.72 (br, 1 H); 2.12, 2.30, 2.44, and 2.87 (all s, together 6 H); 2.58, 2.76, 2.91, 2.98, 3.09, 3.25, 3.50, 3.61, and 3.73 (all m, together 7 H); 6.90–7.85 (m, 12 H).

(3E)-1,1-Dimethyl-4-(N-methyl-N-((1R)-1-(N-methyl-N-phenethylcarbamoyl)-2-(2-naphthyl)ethyl)carbamoyl)but-3-enylcarbamic acid tert-butylester

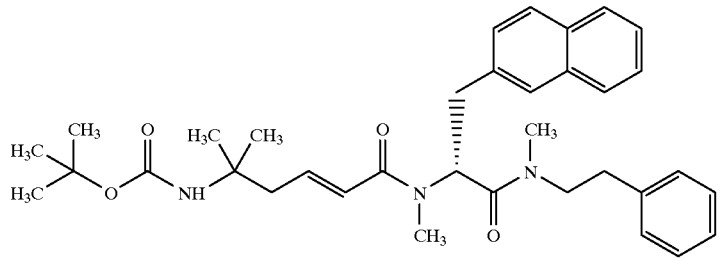

(2E)-5-(tert-Butoxycarbonylamino)-5-methylhex-3-enoic acid (303 mg, 1.04 mmol) was dissolved in N,N-dimethylformamide (2 ml) and dichloromethane (2 ml). Hydroxy-7-azabenzotriazole (170 mg, 1.25 mmol) was added as a solid. The solution was cooled to 0° C. N-(3-dimethylaminopropyl)-N'-ethylcarbodiimide hydrochloride (299 mg, 1.56 mmol) was added. The solution was stirred for 10 min at 0° C. (2R)-2-(Methylamino)-3-(2-naphthyl)propionic acid N-methyl-N-phenethylamide (360 mg, 1.04 mmol) was dissolved in dichloromethane (2 ml) and added to the reaction mixture. Ethyldiisopropylamine (0.18 ml, 1.04 mmol) was added. The reaction mixture was stirred for 16 h, while it was warming to room temperature. The solution was diluted with water (200 ml) and ethyl acetate (150 ml). 10% aqueous sodium hydrogen sulfate solution (50 ml) was added. The phases were seperated, and the aqueous phase was extracted with ethyl acetate (4×50 ml). The combined organic layers were washed with saturated sodium hydrogen carbonate solution (200 ml) and dried over magensium sulfate. The solvent was removed in vacuo. The crude product was purified by flash chromatography on silica (110 g), using ethyl acetate/heptane 1:1 as eluent, to give 546 mg of (3E)-1,1-dimethyl-4-(N-methyl-N-((1R)-1-(N-methyl-N-phenethylcarbamoyl)-2-(2-naphthyl)ethyl)carbamoyl)but-3-enylcarbamic acid tert-butylester.

$^1$H-NMR (CDCl$_3$): d 1.14, 1.17, 1.23, and 1.26 (all s, together 6 H); 1.38 and 1.41 (both s, together 9H); 2.40–3.10, 3.30–3.60, and 3.92 (all m, together 8 H); 2.78, 2.89, and 3.03 (all s, together 6 H); 4.28 and 4.40 (both br, together 1 H); 5.78 and 5.85 (both dd, together 1 H); 6.15 and 6.23 (both d, together 1 H); 6.70 and 6.80 (both m, together 1 H); 7.00–7.85 (m, 12 H).

(3E)-1,1-dimethyl-4-(N-methyl-N-((1R)-1-(N-methyl-N-phenethylcarbamoyl)-2-(2-naphthyl)ethyl)carbamoyl)but-3-enylcarbamic acid tert-butylester (528 mg, 0.85 mmol) was dissolved in dichloromethane (2 ml). Trifluoroacetic acid (2 ml) was added. The solution was stirred at room temperature for 10 min. The solvent was removed in vacuo at 20° C. The residue was dissolved in dichloroemethane (50 ml), and the solvent was removed in vacuo. This latter procedure was repeated two times. The crude product was purified by flash chromatography on silcia, using dichloromethane/methanol/25% aqueous ammonia (100:10:1) as eluent to give 320 mg of the title compound as free base. 100 mg of this was dissolved in ethyl acetate (3 ml). 3M hydrogen chloride in ethyl acetate (0.7 ml) was added. The solvent was removed in vacuo. The residue was purified by two HPLC-chromatographies on a 25 mm×250 mm 10 m C18 silica column at 40° C. with a gradient of 30 to 43% acetonitrile in a 0.1M ammonium sulfate buffer, which was adjusted to pH 2.5 with 4M sulfuric acid. The peptide containing fractions were collected, diluted with 3 volumes of water and applied to a Sep-Pak® C18 cartridge (Waters part. #: 51910) which was equilibrated with 0.1% trifluoroacetic acid. The peptide was eluted from the Sep-Pak® cartridge with 70% acetonitrile in a 0.1% trifluoroacetic acid solution in water. The product was liophilized to give 10 mg of the title compound as trifluoroacetate.

HPLC (A1): R$_t$ 34.27 min.

NMR (CDCl$_3$, selected values, free base): d 1.04, 1.05, 1.1 1, and 1.12 (all s, together 6 H); 5.78 and 5.87 (both dd, together 1 H); 6.14 and 6.23 (both d, together 1 H); 6.78 and 6.87 (both dt, together 1 H).

MS: 472.1 [M+H]$^+$.

Example 2

(2R)-2-(N-((2E)-5-((2R)-2-hydroxypropylamino)-5-methylhex-2-enoyl)-N-methylamino)-N-methyl-3-(2-naphthyl)-N-phenethylpropionamide

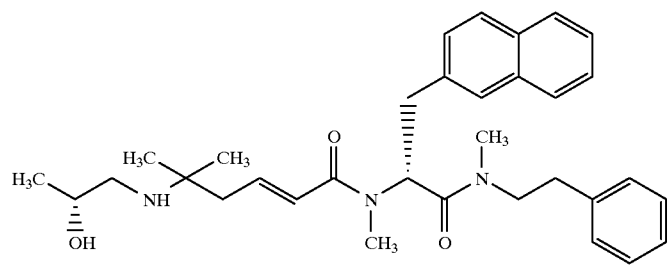

(2R)-2-(N-((2E)-5-((2R)-2-(tert-Butoxydimethylsilyloxy)propylamino)-5-methylhex-2-enoyl)-N-methylamino)-N-methyl-3-(2-naphthyl)-N-phenethylpropionamide

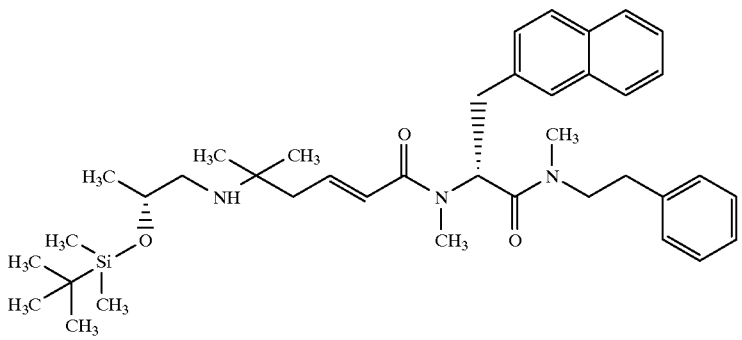

(2R)-2-(N-((2E)-5-Amino-5-methylhex-2-enoyl)-N-methylamino)-3-(2-naphthyl)propionic acid N-methyl-N-phenethylamide (179 mg, 0.38 mmol) was dissolved in methanol (10 ml). Glacial acetic acid (0.30 ml, 5.30 mmol) and mol sieves (3 Å, 5.0 g) were added successively. (2R)-2-(tert-Butyldimethylsilyloxy)propanal (500 mg, 2.66 mmol) was dissolved in methanol (3 ml) and added to the reaction mixture. Sodium cyanoborohydride (95 mg, 1.51 mmol) was added as a solid. The reaction mixture was stirred for 3 h at room temperature. Another portion of sodium cyanoborohydride (95 mg, 1.51 mmol) was added. The reaction mixture was stirred 16 h at room temperature. The mol sieves was filtered off through a plug of celite, which was washed with methanol (30 ml). The solvent was removed in vacuo. The residue was dissolved in water/1N sodium hydroxide solution (50 ml/50 ml). The solution was extracted with diethyl ether (3×50 ml). The combined organic layers were dried over magnesium sulfate. The solvent was removed in vacuo. The crude product was purified by flash chromatography on silica (60 g) using ethyl acetate/heptane/triethylamine (10:10:1) as eluent to give 160 mg of (2R)-2-(N-((2E)-5-((2R)-2-(tert-butoxydimethylsilyloxy)-propylamino)-5-methylhex-2-enoyl)-N-methylamino)-N-methyl-3-(2-naphthyl)-N-phenethylpropionamide.

$^1$H-NMR (CDCl$_3$, selected values): d=5.80 and 5.86 (t and dd, together 1 H); 6.14 and 6.23 (both d, together 1 H); 6.85 (m, 1 H).

(2R)-2-(N-((2E)-5-((2R)-2-(tert-Butoxydimethylsilyloxy)-propylamino)-5-methylhex-2-enoyl)-N-methylamino)-N-methyl-3-(2-naphthyl)-N-phenethylpropionamide (135 mg, 0.21 mmol) was dissolved in THF (2 ml). An 1.1M solution of tertabutylammonium fluoride (0.42 ml, 0.46 mmol) was added. The reaction mixture was stirred for 1 h at room temperature. The solution was diluted with ethyl acetate (50 ml). It was extracted with saturated sodium hydrogen carbonate solution (3×20 ml). The combined organic layers were dried over magnesium sulfate. The solvents were removed in vacuo. The residue was purified on silica (20 g), using dichloromethane/methanol/25% aqueous ammonia (100:10:1) as eluent to give 24 mg of the crude product. The residue was purified by HPLC-chromatography on a 25 mm×250 mm 10 m C18 silica column at 40° C. with a gradient of 30.0 to 43.5% acetonitrile in a 0.1M ammonium sulfate buffer, which was adjusted to pH 2.5 with 4M sulfuric acid. The peptide containing fractions were collected, diluted with 3 volumes of water and applied to a Sep-Pak® C18 cartridge (Waters part. #: 51910) which was equilibrated with 0.1% trifluoroacetic acid. The peptide was eluted from the Sep-Pak® cartridge with 70% acetonitrile in a 0.1% trifluoroacetic acid solution in water. The product was liophilized to give 10.7 mg of the title compound as trifluoroacetate.

HPLC:

R$_t$ 35.13 (A1)
R$_t$ 37.08 (B1)
MS:
530.8±0.5 (M+1)

Example 3

(2R)-2-((5R)-4-((2E)-5-Amino-5-methylhex-2-enoyl)-5-(2-naph-thyl)methyl-2-oxopiperazin-1-yl)-N-methyl-3-phenyl propionamide.

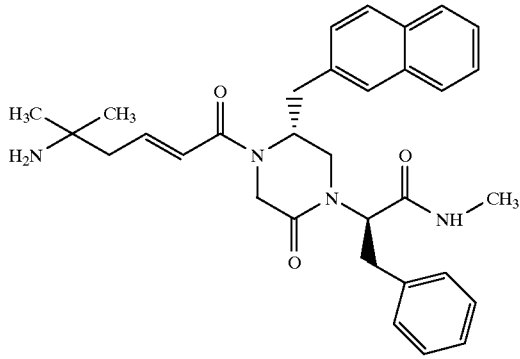

((1R)-1-(((1R)-1-Methylcarbamoyl-2-phenylethylamino)methyl)-2-(2-naphthyl)ethyl)carbamic acid tert butyl ester.

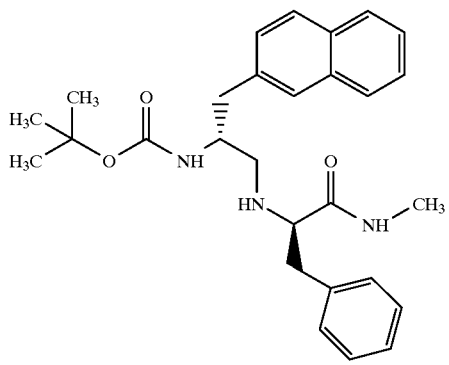

D-Phenylalanine-N-methyl amide (1.50 g, 8.35 mmol) and (1R)-1-formyl-2-(2-naphthyl)ethylcarbamic acid tert-butyl ester (2.50 g, 8.35 mmol) were dissolved in methanol (40 ml). Molsieves (3 Å, 30 g) and acetic acid (3 ml) were added and the mixture was cooled with ice and sodium cyanoborohydride (0.80 g, 12.5 mmol) was added. The mixture was stirred overnight at room temperature. Water (30 ml) and saturated aqueous sodium hydrogen carbonate (30 ml) were added and the mixture was extracted with methylene chloride (3×40 ml). The combined organic phases were dried (magnesium sulfate) and the solvent was removed in vacuo. The residue was chromatographed on silica (3×30 cm) using ethyl acetate/heptane (1:1) as eluent to afford 1.19 g of ((1R)-1-(((1R)-1-methylcarbamoyl-2-phenylethylamino)methyl)-2-(2-naphthyl)ethyl)carbamic acid tert butyl ester $^1$H-NMR: (CDCl$_3$) d 1.37 (s, 9H); 2.32 (dd, 1H); 2.49–2.71 (m, 4H); 2.75 (d, 3H); 3.21 (m, 2H); 3.94 (m, 1H); 4.32 (d, 1H); 7.12–7.81 (12 arom. H)

((1R)-1-((N-Chloroacetyl-N-((1R)-1-(methylcarbamoyl)-2-phenylethyl)amino)methyl)-2-(2-naphthyl)ethyl)carbamic acid tert butyl ester.

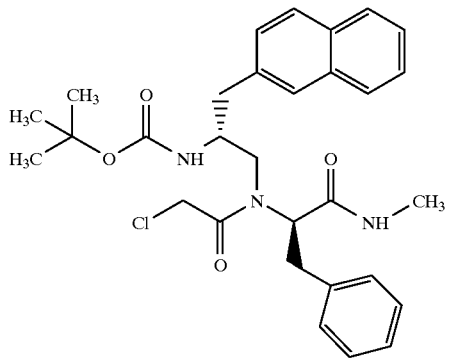

((1R)-1-(((1R)-1-Methylcarbamoyl-2-phenylethylamino)methyl)-2-(2-naphthyl)ethyl)carbamic acid tert-butyl ester (1.00 g, 2.18 mmol) was dissolved in methylene chloride (20 ml).

Diisopropylethylamine (0.37 ml, 2.13 mmol) was added and the mixture was cooled with ice. Chloroacetic anhydride (0.37 g, 2.18 mmol) was dissolved in methylene chloride (20 ml) and added dropwise. The mixture was stirred overnight. Chloroacetic anhydride (0.18 g, 1.09 mmole was added) and the mixture was stirred 1 h. Water (20 ml) and methylene chloride (20 ml) were added and the organic phase was washed with an aqueous solution of sodium hydrogen sulphate (10%, 25 ml), a saturated aqueous solution of sodium hydrogen carbonate (25 ml), and dried (magnesium sulfate) and the solvent was removed in vacuo. The residue was chromatographed on silica (3×30 cm) using ethyl acetate/heptane (1:1) as eluent to afford 0.57 g of ((1R)-1-((N-chloroacetyl-N-((1R)-1-(methylcarbamoyl)-2-phenylethyl)amino)methyl)-2-(2-naphthyl)ethyl)carbamic acid tert butyl ester $^1$H-NMR,: (CDCl$_3$) (selected peaks for major rotamer) d 1.38 (s, 9H); 2.80 (d, 3H); 3.95 (m, 2H); 6.90–7.78 (12 arom. H)

ESMS: m/z 538

(R-2-(N-((2R)-2-Amino-3-(2-naphthyl)propyl)-N-chloroacetylamino)-N-methyl-3-phenylpropionamide.

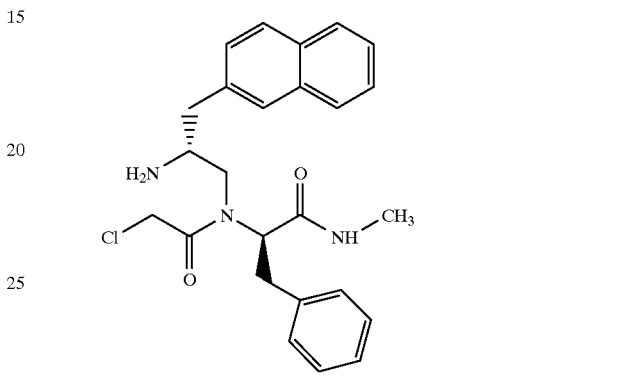

((1R)-1-((N-Chloroacetyl-N-((1R)-1-(methylcarbamoyl)-2-phenylethyl)amino)methyl)-2-(2-naphthyl)ethyl)carbamic acid tert-butyl ester (0.56 g, 1.04 mmol) was dissolved in a mixture of trifluoroacetic acid (4 ml) and methylene chloride (4 ml) and stirred for 40 min. The solvent was removed in vacuo and methylene chloride was added and removed in vacuo (3×10 ml) to afford 0.69 g of (2R)-2-(N-((2R)-2-amino-3-(2-naphthyl)propyl)-N-chloroacetylamino)-N-methyl-3-phenylpropionamide as a trifluoroacetate.

$^1$H-NMR: (CDCl$_3$)(selected peaks for major rotamer) d 2.67 (d, 3H); 3.85, 3.95 (two d (AB-syst.), 2H); 4.55 (t, 1H).

ESMS: m/z: 438 (M+H)$^+$ (2R)-N-Methyl-2-((5R)-5-((2-naphthyl)methyl)-2-oxopiperazin-1-yl)-3-phenylpropionamide.

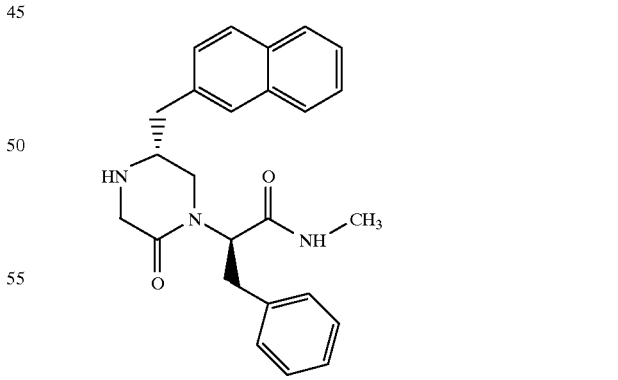

(2R)-2-(N-((2R)-2-Amino-3-(2-naphthyl)propyl)-N-chloroacetyl-amino)-N-methyl-3-phenylpropionamide (0.69 g, 1.58 mmol) was dissolved in methanol (14 ml) and sodium hydrogen carbonate (0.40 g, 4.73 mmol) and water (7 ml) were added. The mixture was stirred overnight at room temperature. The solvent was removed in vacuo and the residue was dissolved in a mixture of ethyl acetate (30 ml) and saturated aqueous sodium hydrogen carbonate (20 ml). The mixture was extracted with ethyl acetate (4×20 ml). The combined organic phases were dried (magnesium sulfate) and the solvent was removed in vacuo. The residue was chromatographed on silica (2×20 cm) using methylene chloride/methanol/25% aqueous ammonia (100:10:1) to afford 0.19 g of (2R)-N-methyl-2-((5R)-5-((2-naphthyl)methyl)-2-oxopiperazin-1-yl)-3-phenylpropionamide $^1$H-NMR: (CDCl$_3$) d 2.74 (d, 3H); 2.78–3.05 (m, 5H); 3.22 (dd, 1H); 3.30 (m, 1 H); 3.32, 3.55 (two d (AB-syst), 2H); 5.27 (dd, 1H); 6.34 (s(br), 1H); 7.05–7.78 (12 arom. H).

ESMS: m/z 403 (M+H)$^+$ ((3E)-1,1-Dimethyl-5-((2R)-4-((1R)-1-(methylcarbamoyl)-2-phenylethyl)-2-((2-naphthyl)methyl)-5-oxopiperazin-1-yl)-5-oxopent-3-enyl)carbamic acid tert-butyl ester.

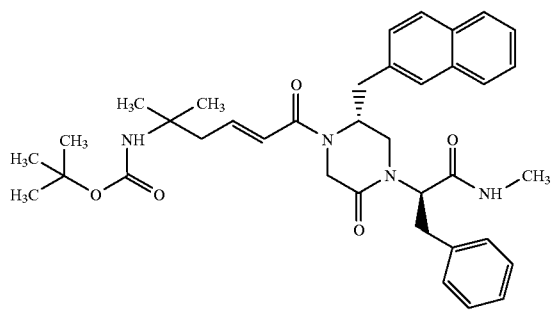

(2E)-5-Methyl-5-(tert-butyloxycarbonylamino)hex-2-enoic acid was dissolved in methylene chloride (10 ml). 1-Hydroxy-7-azabenzotriazol (60 mg, 0.46 mmol) and N-(3-dimethylaminopropyl)-N'-ethylcarbodiimide hydrochloride (100 mg, 0.51 mmol) were added and the mixture was stirred for 15 min. (2R)-N-Methyl-2-((5R)-5-((2-naphthyl)methyl)-2-oxopiperazin-1-yl)-3-phenylpropionamide (185 mg, 0.46 mmol) and diisopropylethylamine (0.08 ml) were added and the mixture was stirred overnight. Water (10 ml) and methylene chloride (10 ml) were added and the mixture was washed with an aqueous solution of sodium hydrogen sulphate (10%, 20 ml), a saturated aqueous solution of sodium hydrogen carbonate (20 ml), dried (magnesium sulfate) and the solvent was removed in vacuo. The residue was chromatographed on silica (3×30 cm) using ethyl acetate/heptane (1:1) as eluent to afford 0.20 g of ((3E)-1,1-dimethyl-5-((2R)-4-((1R)-1-(methylcarbamoyl)-2-phenylethyl)-2-((2-naphthyl)methyl)-5-oxopiperazin-1-yl)-5-oxopent-3-enyl) carbamic acid tert-butyl ester.

$^1$H-NMR: (CDCl$_3$)(selected peaks for major rotamer) d 1.21 (s, 6H); 1.38 (s, 9H); 2.91 (d, 3H); 5.35 (dd, 1H); 5.42 (t, 1H);

((3E)-1,1-Dimethyl-5-((2R)-4-((1R)-1-(methylcarbamoyl)-2-phenylethyl)-2-((2-naphthyl)methyl)-5-oxopiperazin-1-yl)-5-oxopent-3-enyl)carbamic acid tert-butyl ester (0.20 g, 0.32 mmol) was dissolved in methylene chloride (2 ml) and trifluoracetic acid (2 ml) and stirred for 7 min. Water (1 ml) and methylene chloride (10 ml) was added and pH was adjusted to neutral with solid sodium hydrogen carbonate. The aqueous phase was extracted with methylene chloride (3×8 ml). The combined organic phases were dried (magnesium sulfate) and the solvent was removed in vacuo to afford 0.160 g of the title compound.

$^1$H-NMR: (CDCl$_3$)(selected peaks for major rotamer) d 1.28 (s, 3H); 1.35 (s, 3H); 2.75 (d, 3H); 4.05, 4.30 (AB, 2H); 5.05 (dd, 1H); 5.27 (dd, 1H); 6.15 (d, 1H).

HPLC: r$_t$=28.8 min (A1)

Example 4

(2E)-5-Amino-5-methyl-N-methyl-N-((1R)-1-(N-methyl-N-(2-(2-thienyl)ethyl)carbamoyl)-2-(2-naphthyl)ethyl)hex-2-enamide

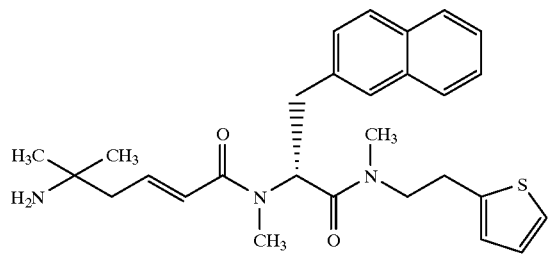

3-Hydroxy-1,1-dimethylpropylcarbamic acid tert-butyl ester:

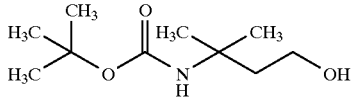

At 0° C., ethyl chloroformate (1.10½, 11.5 mmol) was given dropwise to a solution of 3-tert-butoxycarbonylamino-3-methylbutanoic acid (2.50 g, 11.5 mmol) and triethylamine (1.92 mL, 13.8 mmol) in tetrahydrofuran (10 mL). The solution was stirred for 40 min at 0° C. The formed precipitate was filtered off and washed with tetrahydrofuran (20 mL). The liquid was immediately cooled to 0° C. A 2M solution of lithium boronhydride in tetrahydrofuran (14.4 mL, 28.8 mmol) was added dropwise. The solution was stirred at 0° C. for 2 h, and then warmed to room temperature over a period of 4 h. It was cooled to 0° C. Methanol (5 mL) was added carefully. 1N Hydrochloric acid (100 mL) was added. The solution was extracted with ethyl acetate (2×100 mL, 3×50 ml). The combined organic layers were washed with saturated sodium hydrogen carbonate solution (100 ml) and dried over magnesium sulfate. The solvent was removed in vacuo. The crude product was chromatographed on silica (110 g) with ethyl acetate/heptane 1:2 to give 1.84 g of 3-hydroxy-1,1-dimethylpropylcarbamic acid tert-butyl ester.

$^1$H-NMR (CDCl$_3$):__d 1.33 (s, 6 H); 1.44 (s, 9 H); 1.88 (t, 2 H); 1.94 (br, 1 H); 3.75 (q, 2 H); 4.98 (br, 1 H).

3-(tert-Butoxycarbonylamino)-3-methylbutanal:

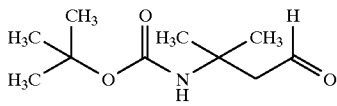

Dimethylsufoxide (1.22 ml, 17.2 mmol) was added to a solution of oxalyl chloride (1.1 ml, 12.9 mmol) at −78° C. in dichloromethane (15 ml). The mixture was stirred for 15 min at −78° C. A solution of 3-hydroxy-1,1-dimethylpropylcarbamic acid tert-butyl ester (1.75 g, 8.6 mmol) in dichloromethane (10 ml) was added dropwise over a period of 15 min. The solution was stirred at −78° C. for another 15 min. Triethylamine (6.0 ml, 43 mmol) was added. The solution was stirred at −78° C. for 5 min and then warmed to room temperature. The solution was diluted with dichloromethane (100 ml) and extracted with 1N hydrochloric acid (100 ml). The aqueous phase was extracted with dichloromethane (50 ml). The combined organic layers were washed with saturated sodium hydrogen carbonate solution (100 ml) and dried over magnesium sulfate. The solvent was removed in vacuo. The crude product was purified by column chromatography on silica (140 g) with ethyl acetate/heptane (1:3) to give 1.10 g of 3-(tert-butoxycarbonylamino)-3-methylbutanal.

$^1$H-NMR (CDCl$_3$):__d 1.39 (s, 6 H); 1.45 (s, 9 H); 2.85 (d, 2 H); 4.73 (br. 1 H); 9.80 (t, 1 H).

Ethyl (2E)-5-(tert-Butoxycarbonylamino)-5-methylhex-2-enoate:

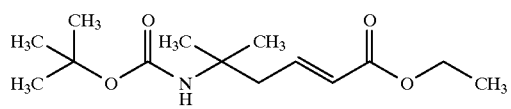

Triethylphoshonoacetate (1.96 ml, 9.8 mmol) was dissolved in tetrahydrofuran (30 ml). Potassium tert-butoxide (1.10 g, 9.8 mmol) was added. The solution was stirred for 40 min at room temperature. A solution of 3-(tert-butoxycarbonylamino)-3-methylbutanal (1.10 g, 5.5 mmol) in Tetrahydrofuran (6 ml) was added. The solution was stirred at room temperature for 75 min. It was diluted with ethyl acetate (100 ml) and 1N hydrochloric acid (100 ml). The phases were separated. The aqueous phase was extracted with ethyl acetate (2×50 ml). The combined organic phases were washed with saturated sodium hydrogen carbonate solution (60 ml) and dried over magnesium sulfate. The solvent was removed in vacuo. The crude product was purified by column chromatography on silica (90 g) with ethyl acetate/hepatane (1:4) to give 1.27 g of ethyl (2E)-5-(tert-butoxycarbonylamino)-5-methylhex-2-enoate.

$^1$H-NMR (CDCl$_3$):__d 1.30 (s, 6 H); 1.30 (t, 3 H); 1.46 (s, 9 H); 2.62 (d, 2 H); 4.27 (q, 2 H); 4.42 (br, 1 H); 5.88 (d, 1 H); 6.94 (td, 1 H).

(2E)-5-(tert-Butoxycarbonylamino)-5-methylhex-2-enoic acid:

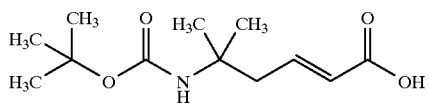

Ethyl (2E)-5-(tert-butoxycarbonylamino)-5-methylhex-2-enoate (1.233 g, 4.54 mmol) was dissolved in dioxane (20 ml). Lithium hydroxide (0.120 g, 5.00 mmol) was added as a solid. Water (10 ml) was added, until a clear solution was reached. The solution was stirred 16 h at room temperature. The solution was diluted with water (70 ml) and was extracted with tert-butyl methyl ether (2×100 ml). The aqueous phase was acidified with 1N sodium hydrogensulfate solution (pH=1) and was extracted with tert-butylmethylether (3×70 ml). The organic phases were combined and dried over magnesium sulfate. The solvent was removed in vacuo to give 1.05 g of (2E)-5-(tert-butoxycarbonylamino)-5-methylhex-2-enoic acid. The crude product was used for further syntheses.

$^1$H-NMR (DMSO d$_6$):__d 1.15 (s, 6 H); 1.35 (s, 9 H); 2.53 (d, 2 H); 5.75 (d, 1 H); 6.57 (br, 1 H); 6.75 (td, 1 H); 12.15 (s, 1 H).

N-(2-(2-Thienyl)ethyl)formamide:

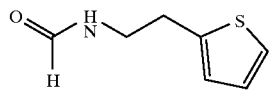

2-(2-thienyl)ethylamine (15.0 g, 118 mmol) was dissolved in formic acid (120 ml) while cooling with an water bath. The solution was cooled to 0° C. Acetic acid anhydride (45 ml) was added dropwise. The reaction mixture was stirred at room temperature for 3 h. It was cooled to 0° C., and water (45 ml) was added dropwise. The mixture was stirred for 16 h, while it was warming up to room temperature. The solvent was removed in vacuo. The residue was dissolved in ethyl acetate (300 ml). The solution was washed with water (2×150 ml) and saturated sodium hydrogen carbonate solution (200 ml). It was dried over magnesium sulfate. The solvent was removed in vacuo. The crude product was purified by flash chromatography on silica (180 g), using ethyl acetate/heptane (2:1) as eluent to give 14.30 g of N-(2-(2-thienyl)ethyl)formamide.

$^1$H-NMR (CDCl$_3$):__d 3.07 (t, 2 H); 3.59 (q, 2 H); 5.90 (br, 1 H); 6.85 (d, 1 H); 6.95 (dd, 1 H); 7.17 (d, 1 H); 8.12 (s, 1 H).

N-Methyl-N-(2-(2-thienyl)ethyl)amine:

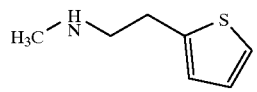

At 7° C., a solution of N-(2-(2-thienyl)ethyl)formamide (9,98 g, 63.8 mmol) in tetrahydrofuran (200 ml) was added to a suspension of sodium borohydride (2.89 g, 76.5 mmol) in tetrahydrofuran (200 ml). The mixture was stirred for 10 min. A solution of iodine (8.09 g, 31.9 mmol) in tetrahydrofuran (200 ml) was added dropwise. The reaction mixture was stirred for 30 min at 7° C. and 30 min at room temperature. It was heated to reflux for 16 h. The reaction mixture was cooled to 7° C. Methanol (500 ml) was added dropwise. The solvent was removed in vacuo. The residue was dissolved in 20% aqueous sodium hydroxide solution (500 ml) and tert-butyl methyl ether (200 ml). The phases were separated. The aqueous phase was extracted with tert-butyl methyl ether (2×200 ml). The combined organic layers were dried over magensium sulfate. The solvent was removed in vacuo. The crude product was purified by flash chromatography on silica (220 g), using dichloromethane/methanol/25% aqueous ammonia (100:10:1) as eluent to give 2.82 g of N-methyl-N-(2-(2-thienyl)ethyl)amine.

$^1$H-NMR (CDCl$_3$):__d 2.05 (s, 1 H); 2.46 (s, 3 H); 2.90 (t, 2 H); 3.04 (t, 2 H); 6.84 (d, 1 H); 6.94 (dd, 1 H); 7.15 (d, 1 H).

N-Methyl-N-((1R)-1-(N-methyl-N-(2-(2-thienyl)ethyl)carbamoyl)-2-(2-naphthyl)ethyl)carbamic acid tert-butyl ester:

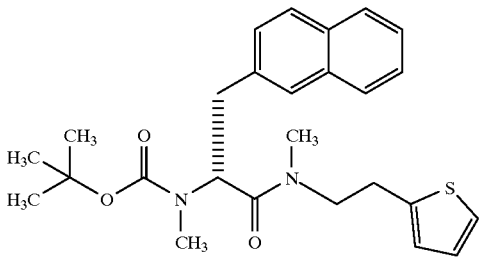

(2R)-2-(N-(tert-Butoxycarbonyl)-N-methylamino)-3-(2-naphthyl)propionic acid (4.52 g, 13.7 mmol) was dissolved in N,N-dimethylformamide (6 ml) and dichloromethane (6 ml). 1-Hydroxy-7-azabenzotriazole (1.86 g, 13.7 mmol) was added as a solid. The solution was cooled to 0° C. N-(3-dimethylaminopropyl)-N'-ethylcarbodiimide hydrochloride (2.63 g, 13.7 mmol) was added. The solution was stirred for 15 min at 0° C. A solution of N-methyl-N-(2-(2-thienyl)ethyl)amine in dichloromethane (6 ml) was added. Ethyldiisopropylamine (2.37 ml, 13.7 mmol) was added. The reaction mixture was stirred for 16 h, while it was warming up to room temperature. It was diluted with ethyl acetate (200 ml). The mixture was washed with 1N hydrochloric acid (150 ml) and saturated sodium hydrogen carbonate solution (150 ml). It was dried over magnesium sulfate. The solvent was removed in vacuo. The crude product was purified by flash chromatography on silcia (100 g), using ethyl acetate/heptane (1:2) as eluent to give 5.57 g of N-methyl-N-((1R)-1-(N-methyl-N-(2-(2-thienyl)ethyl)carbamoyl)-2-(2-naphthyl)ethyl)carbamic acid tert-butyl ester.

$^1$H-NMR (CDCl$_3$, selected values): _d 4.84, 5.05, and 5.86 (dd, dd, and m, together 1 H); 6.60–7,90 (m, 10 H).

(2R)-N-Methyl-2-(methylamino)-3-(2-naphthyl)-N-(2-(2-thienyl)ethyl)propionamide:

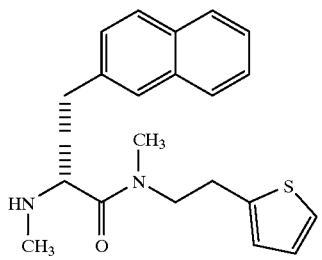

N-Methyl-N-((1R)-1-(N-methyl-N-(2-(2-thienyl)ethyl)carbamoyl)-2-(2-naphthyl)ethyl)carbamic acid tert-butyl ester (5.17 g, 11.4 mmol) was dissolved in dichloromethane (12 ml). The solution was cooled to 0° C. Trifluoroacetic acid (12 ml) was added. The reaction mixture was stirred for 15 min at 0° C. The solvent was removed in vacuo at 20° C. The residue was codistilled with dichloromethane (3×60 ml). The crude product was purified by flash chromatography on silica (80 g), using dichloromethane/methanol/25% aqueous (100:10:1) ammonia as eluent, to give 1.91 g of (2R)-N-methyl-2-(methylamino)-3-(2-naphthyl)-N-(2-(2-thienyl)ethyl)propionamide.

$^1$H-NMR (CDCl$_3$): _d 2.18, 2.32, 2.46, and 2.89 (all s, together 6 H); 2.50–3.60 (m, together 6 H); 3.65 and 3.75 (both dd, together 1 H); 6.58 and 6.69 (both d, together 1 H); 6.87, 7.10, 7.35, 7.45, 7.76 (all m, together 8 H); 7.62 and 7.65 (both s, together 1 H).

(3E)-1,1-Dimethyl-4-(N-methyl-N-((1R)-1-(N-methyl-N-(2-(2-thienyl)ethyl)carbamoyl)-2-(2-naphthyl)ethyl)carbamoyl)but-3-enylcarbamic acid tert-butyl ester:

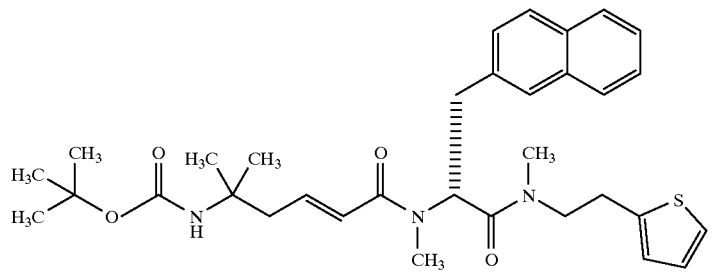

(2E)-5-tert-Butoxycarbonylamino-5-methylhex-2-enoic acid (380 mg, 1.56 mmol) was dissolved in N,N-dimethylformamide (2 ml) and dichloromethane (2 ml). 1-Hydroxy-7-azabenzotriazole (299 mg, 1.56 mmol) was added as a solid. The solution was cooled to 0° C. N-(3-dimethylaminopropyl)-N'-ethylcarbodiimide hydrochloride (380 mg, 1.56 mmol) was added. The solution was stirred for 15 min. at 0° C. A solution of (2R)-N-methyl-2-(methylamino)-3-(2-naphthyl)-N-(2-(2-thienyl)ethyl) propionamide (500 mg, 1.42 mmol) in dichloromethane (2 ml) was added. Ethyldiisopropylamine (0.25 ml, 1.42 mmol) was added. The solution was stirred for 16 h, while it was warming up to room temperature. It was diluted with ethyl acetate (70 ml) and washed with 1N hydrochloric acid (100 ml). The organic layer was washed with saturated sodium hydrogen carbonate solution (100 ml) and dried over magnesium sulfate. The solvent was removed in vacuo. The crude product was purified by flash chromatography on silica (150 g), using ethyl acetate/heptane (1:1) as eluent, to give 679 mg of (3E)-1,1-dimethyl4-(N-methyl-N-((1R)-1-(N-methyl-N-(2-(2-thienyl)ethyl)carbamoyl)-2-(2-naphthyl)ethyl)carbamoyl)but-3-enylcarbamic acid tert-butyl ester.

$^1$H-NMR (CDCl$_3$, selected values): _d 1.14, 1.17, 1.21, and 1.24 (all s, together 6 H); 1.39 and 1.41 (both s, together 9 H); 2.82, 2.91, 3.03, and 3.06 (all s, together 6 H); 5.84 and 5.88 (both dd, together 1 H); 6.15 and 6.26 (both d, together 1 H).

(3E)-1,1-Dimethyl4-(N-methyl-N-((1R)-1-(N-methyl-N-(2-(2-thienyl)ethyl)carbamoyl)-2-(2-naphthyl)ethyl)carbamoyl)but-3-enylcarbamic acid tert-butyl ester (640 mg, 1.11 mmol) was dissolved in dichloromethane (3 ml). The solution was cooled to 0° C. Trifluoroacetic acid (3 ml) was added. The solution was stirred for 15 min at 0° C. The solvent was removed in vacuo without warming. The residue was codistilled with dichloromethane (3×50 ml). The crude product was purified by flash chromatography on silica (60 g), using dichloromethane/methanol/25% aqueous ammonia (100:10:1) as eluent, to give 416 mg of the title compound.
HPLC: $R_t$=33.48 min (A1).
$B_t$=35.13 min (B1).
MS: 478.2, $[M+H]^+$.
$^1$H-NMR (CDCl$_3$, selected values): d 1.04, 1.05, 1.11, and 1.11 (all s, together 6 H); 2.80, 2.90, 3.04 and 3.07 (all s, together 6 H); 5.83 and 5.88 (both dd, together 1 H); 6.14 and 6.25 (both d, together 1 H).

For biological testing, the title compound was dissolved in 0.5M acetic acid and lyophilized.

Example 5

(2E)-5-Methyl-5-(methylamino)-N-methyl-N-((1R)-1-(N-methyl-N-(2-(2-thienyl)ethyl)carbamoyl)-2-(2-naphthyl)ethyl)hex-2-enamide

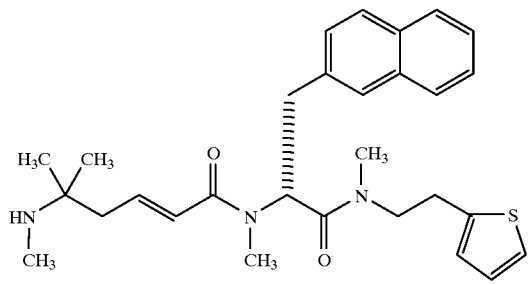

(2E)-5-(N-(tert Butoxycarbonyl)-N-methylamino)-5-methylhex-2-enoic acid.

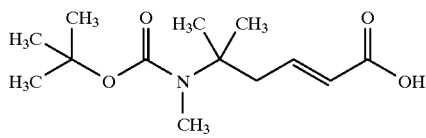

(2E)-5-(tert-Butyloxycarbonylamino)-5-methylhex-2-enoic acid (5.00 g; 20.6 mmol) was dissolved in tetrahydrofuran (70 ml). Methyl iodide (10.3 ml; 164 mmol) was added and the solution was cooled to 0° C. Sodium hydride (60% in oil)(2.07 g; 61.6 mmol) was added in portions and the solution was stirred at room temperature for four days. Ethyl acetate (70 ml) and water (60 ml) was added dropwise and the solvent was removed in vacuo. The crude product was dissolved in water (40 ml) and ether (40 ml). The organic phase was washed with a saturated aqueous solution of sodium hydrogencarbonate (30 ml). The aqueous phases were mixed and 5% aqueous citric acid was added to pH 3. The aqueous phase was extracted with ethyl acetate (4×50 ml). The organic phase was washed with water (2×40 ml), an aqueous solution of sodium thiosulfate (5%; 40 ml), water (40 ml), dried over MgSO$_4$ and the solvent was removed in vacuo. The residue was dissolved in ethyl acetate (45 ml) and washed with an aqueous solution of sodium hydrogensulfate (10%; 3×30 ml), dried over MgSO$_4$ and concentrated in vacuo to give 4.00 g of (2E)-5-(N-(tert-butoxycarbonyl)-N-methylamino)-5-methylhex-2-enoic acid.
$^1$H-NMR (CDCl$_3$): d 1.38 (s, 6H), 1.45 (s, 9H); 2.80 (d, 2H); 2.85 (s, 3H); 5.88 (d, 1H); 7.01 (q, 1H).

N-Methyl-N-((3E)-1,1-dimethyl-4-(N-methyl-N-((1R)-1-(N-methyl-N-(2-(2-thienyl)ethyl)carbamoyl)-2-(2-naphthyl)ethyl)carbamoyl)but-3-enyl)carbamic acid tert-butyl ester:

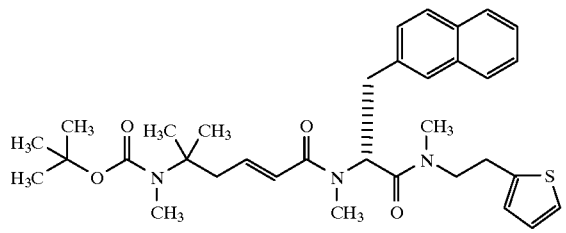

(2E)-5-(N-(tert-Butoxycarbonyl)-N-methylamino)-5-methylhex-2-enoic acid (146 mg, 0.57 mmol) was dissolved in dichloromethane (2 ml) and N,N-dimethylformamide (2 ml). 1-Hydroxy-7-azabenzotriazole (72 mg, 0.57 mmol) was added as a solid. The solution was cooled to 0° C. N-(3-Dimethylaminopropyl)-N'-ethylcarbodiimide hydrochloride (109 mg, 0.57 mmol) was added. The solution was stirred for 15 min at 0° C. A solution of (2R)-N-Methyl-2-(methylamino)-3-(2-naphthyl)-N-(2-(2-thienyl)ethyl) propionamide (200 mg, 0.57 mmol) in dichloromethane (2 ml) was added. Ethyldiisopropylamine (0.1 ml, 0.57 mmol) was added. The reaction mixture was stirred for 16 h, while it was warming up to room temperature. It was diluted with ethyl acetate (50 ml) and washed with 1N hydrochoric acid. The aqueous phase was extracted with ethyl acetate (2×20 ml). The combined organic layers were washed with saturated sodium hydrogen carbonate solution (40 ml) and dried over magnesium sulfate. The solvent was removed in vacuo. The crude product was purified by flash chromatography on silica (80 g), using ethyl acetate/heptane as eluent, to give 270 mg of N-methyl-N-((3E)-1,1-dimethyl-4-(N-methyl-N-((1R)-1-(N-methyl-N-(2-(2-thienyl)ethyl)carbamoyl)-2-(2-naphthyl)ethyl)carbamoyl)but-3-enyl)carbamic acid tert-butyl ester.
$^1$H-NMR (CDCl$_3$, selected values): d 2.67, 2.76, 2.82, 2.90, 3.03, and 3.05 (all s, together 9 H); 5.85 (m, 1 H); 6.10 and 6.22 (both d, together 1 H).

N-Methyl-N-((3E)-1,1-dimethyl-4-(N-methyl-N-((1R)-1-(N-methyl-N-(2-(2-thienyl)ethyl)carbamoyl)-2-(2-naphthyl)ethyl)carbamoyl)but-3-enyl)carbamic acid tert-butyl ester (221 mg, 0.37 mmol) was dissolved in dichloromethane (2 ml). The solution was cooled to 0° C. Trifluoroacetic acid (2 ml) was added. The solution was stirred for 20 min at 0° C. Saturated sodium hydrogen carbonate solution (10 ml) was added. The mixture was adjusted to pH=9, with solid potassium carbonate. The mixture was diluted with water 820 ml). It was extracted with tert-butyl methyl ether (3×30 ml). The combined organic layers were dried over magensium sulfate. The solvent was removed in vacuo. The crude product was purified by flash chromatography on silica (30 g), using dichloromethane/methanol/25% aqueous ammonia as eluent, to give 125 mg of the title compound.
$^1$H-NMR (CDCl$_3$, selected values): d 1.00 and 1.08 (both s, together 6 H); 2.23 and 2.30 (both s, together 3 H); 2.80, 2.89, 3.04, and 3.07 (all s, together 6 H); 5.85 (m, 1 H); 6.13 and 6.25 (both d, together 1 H).
HPLC: 33.27 min (A1)
35.28 min (B1).
MS: 492.0 [M+H].
For biological testing, it was transformed into the acetate by liophyillization from 0.5N acetic acid (25 ml).

Example 6

(2E)-5-Amino-5-methylhex-2-enoic acid N-methyl-N-((1R)-1-(N-methyl-N-(3-phenylpropyl)carbamoyl)-2-(2- naphthyl)ethyl)amide

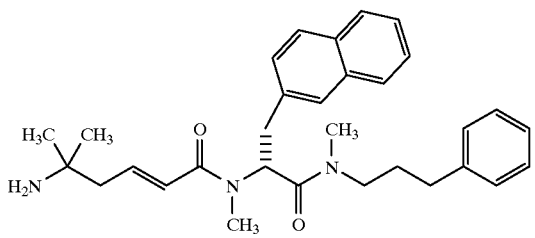

N-(3-Phenylpropyl)formamide

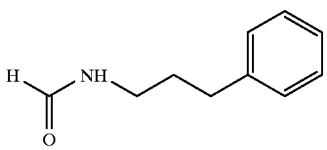

3-Phenylproylamine (10 ml, 70.0 mmol) was added at 0° C. dropwise to formic acid (80 ml). Acetic acid anhydride (30 ml) was added dropwise to the reaction mixture. After the addition the reaction mixture was warmed to room temperature. It was stirred for 2.5 h. It was cooled to 0° C. Water (30 ml) was added dropwise. The reaction mixture was warmed to room temperature. The solvent was removed in vacuo. The residue was dissolved in ethyl acetate (300 ml). The organic phase was washed with saturated sodium chloride solution (2×150 ml) and with saturated sodium hydrogen carbonate solution (200 ml). It was dried over magnesium sulfate. The solvent was removed in vacuo to furnish 5.82 g of N-(3-phenylpropyl)formamide, which was used without further purification.

$^1$H-NMR (CDCl$_3$): d 1.85 (m, 2 H); 2.65 (t, 2 H); 3.21 and 3.30 (both q, together 2 H); 5.85 (broad, 1 H); 7.10–7.50 (m, 5 H); 8.12 (s, 1 H).

N-Methyl-N-(3-phenylpropyl)amine

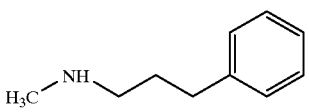

N-(3-Phenylpropyl)formamide (5.70 g, 34.9 mmol) was dissolved in tetrahydrofuran (50 ml) and added dropwise to a suspension of sodium borohydride (1.58 g, 41.91 mmol) in tetrahydrofuran (100 ml), which was cooled to 7° C. A solution of iodine (4.42 g, 17.46 mmol) in tetrahydrofuran was added dropwise, while the temperature was kept at 7° C. After the addition was finished, the reaction mixture was warmed to reflux for 16 h. The reaction mixture was cooled to 7° C., and methanol (250 ml) was added dropwise. The solvent was removed in vacuo. The residue was dissolved in 20% aqueous sodium hydroxide solution (250 ml) and tert-butyl methyl ether (100 ml). The phases were separated. The aqueous phase was extracted with tert-butyl methyl ether (2×100 ml). The combined organic layers were dried over magnesium sulfate. The solvent was removed in vacuo. The crude product was purified by flash chromatography on silica (400 g), using dichloromethane/methanol/25% aqueous ammonia (100:10:1) as eluent to give 2.76 g of N-methyl-N-(3-phenylpropyl)amine.

$^1$H-NMR (CDCl$_3$): d 1.85 (m, 2 H); 2.43 (s, 1 H); 2.50 (s, 3 H); 2.65 (m, 4 H); 7.10–7.40 (m, 5 H).

N-Methyl-N-((1R)-1-(N-methyl-N-(3-phenylpropyl)carbamoyl)-2-(2-naphthyl)ethyl)carbamic acid tert-butyl ester

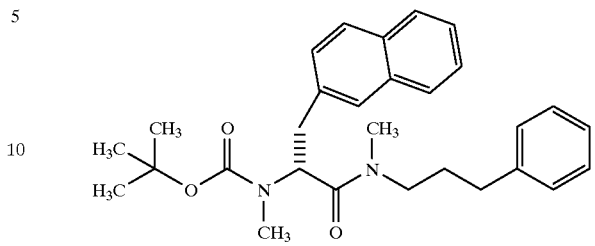

(2R)-$^2$-(N-(tert-Butoxycarbonyl)-N-methylamino)-3-(2-naphthyl)propionic acid (2.21 g, 6.70 mmol) was dissolved in N,N-dimethylformamide (3 ml) and dichloromethane (6 ml). 1-Hydroxy-7-azabenzotriazole (0.91 g, 6.70 mmol) was added. The solution was cooled to 0° C. N-(3-Dimethylaminopropyl)-N'-ethylcarbodiimide hydrochloride (1.28 g, 6.70 mmol) was added. The reaction mixture was stirred for 15 min at 0° C. A solution of N-methyl-N-(3-phenylpropyl)amine (1.0 g, 6.7 mmol) in dichloromethane (3 ml) was added. Ethyldiisopropylamine (1.2 ml, 6.7 mmol) was added. The reaction mixture was stirred for 16 h, while it was slowly warming up to room temperature. The solution was diluted with ethyl acetate (100 ml). It was washed with 1N hydrochloric acid (100 ml). The aqueous phase was extracted with ethyl acetate (100 ml). The combined organic layers were washed with saturated sodium hydrogen carbonate solution (100 ml) and dried over magnesium sulfate. The solvent was removed in vacuo. The crude product was purified by flash chromatography on silica (400 g), using ethyl acetate/heptane (1:3) as eluent to give 1.43 g of N-methyl-N-((1R)-1-(N-methyl-N-(3-phenylpropyl)carbamoyl)-2-(2-naphthyl)ethyl)carbamic acid tert-butyl ester.

$^1$H-NMR (CDCl$_3$, selected values): d 1.25 (broad, 9 H); 1.79 (m, 2 H); 2.88 (broad, 3 H); 5.05 and 5.45 (both m, together 1 H).

(2R)-N-Methyl-2-methylamino-3-(2-naphthyl)-N-(3-phenylpropyl)propionamide

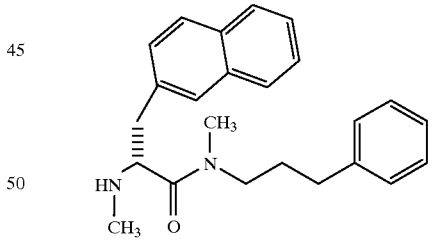

N-Methyl-N-((1R)-1-(N-methyl-N-(3-phenylpropyl)carbamoyl)-2-(2-naphthyl)ethyl)carbamic acid tert-butyl ester (1.43 g, 3.10 mmol) was dissolved in dichloromethane (5 ml). The solution was cooled to 0° C. Trifluoroacetic acid (5 ml) was added. The solution was stirred at 0° C. for 90 min. Dichloromethane (35 ml) and saturated sodium hydrogen carbonate solution were added. Solid sodium hydrogen carbonate was added until pH 7. The phases were separated. The aqueous phase was extracted with dichloromethane (2×100 ml). The combined organic layers were dried over magnesium sulfate. The solvent was removed in vacuo to give 0.91 g of crude (2R)-N-methyl-2-methylamino-3-(2-naphthyl)-N-(3-phenylpropyl)propionamide, which was used without further purification.

¹H-NMR (CDCl₃, selected values): d 0.91–1.35 (m, 2 H); 2.35, 2.42, 2.43, and 2.84 (all s, together 6 H); 3.64 and 3.92 (both dd, together 1 H).

MS: 361.2 [M+1]⁺.

((3E)-1,1-Dimethyl-4-(N-methyl-N-((1R)-1-(N-methyl-N-(3-phenylpropyl)carbamoyl)-2-(2-naphthyl)ethyl)carbamoyl)but-3-enyl)carbamic acid tert-butyl ester

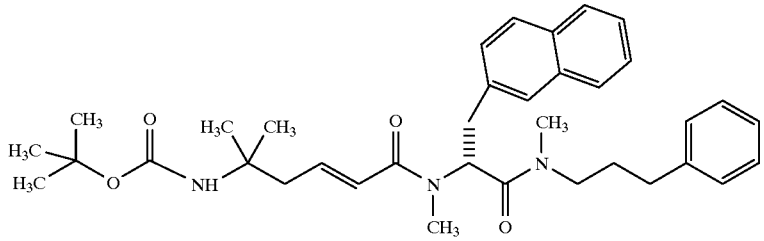

(2E)-5-(tert-Butoxycarbonylamino)-5-methylhex-2-enoic acid (405 mg, 1.66 mmol) was dissolved in N,N-dimethylformamide (4 ml) and dichloromethane (4 ml). 1-Hydroxy-7-azabenzotriazole (227 mg, 1.66 mmol) was added. The solution was cooled to 0° C. N-(3-Dimethylaminopropyl)-N'-ethylcarbodiimide hydrochloride (319 mg, 1.66 mmol) was added. The solution was stirred at 0° C. for 40 min. A solution of (2R)-N-methyl-2-methylamino-3-(2-naphthyl)-N-(3-phenylpropyl)propionamide (600 mg, 1.66 mmol) in dichloromethane (4 ml) was added. Ethyldiisopropylamine (0.29 m., 1.66 mmol) was added. The solution was stirred for 2 days, while it was slowly warming up to room temperature. The reaction mixture was diluted with ethyl acetate (100 ml) and washed with 1N hydrochloric acid (100 ml). The aqueous phase was extracted with ethyl acetate (2×50 ml). The combined organic layers were washed with saturated sodium hydrogen carbonate solution (100 ml) and dried over magnesium sulfate. The solvent was removed in vacuo. The crude product was purified by flash chromatography on silica (180 g), using ethyl acetate/hepaten (1:1) as eluent to give 706 mg of ((3E)-1,1-dimethyl-4-(N-methyl-N-((1R)-1-(N-methyl-N-(3-phenylpropyl)carbamoyl)-2-(2-naphthyl)ethyl)carbamoyl)but-3-enyl)carbamic acid tert-butyl ester.

¹H-NMR (CDCl₃, selected values): d 1.21, 1.24, 1.25, and 1.26 (all s, together 6 H); 1.41 (s, 9 H); 2.83, 2.83, 3.10, and 3.12 (all s, together 6 H); 5.88 and 5.97 (both dd, together 1 H); 6.25 (m, 1 H); 6.80 (m, 1 H).

((3E)-1,1-Dimethyl-4-(N-methyl-N-((1R)-1-(N-methyl-N-(3-phenylpropyl)carbamoyl)-2-(2-naphthyl)ethyl)carbamoyl)but-3-enyl)carbamic acid tert-butyl ester was dissolved in dichloromethane (2 ml). The solution was cooled to 0° C. Trifluoroacetic acid (2 ml) was added. The solution was stirred at 0° C. for 55 min. Dichloromethane (13 ml) was added. A saturated aqueous solution of sodium hydrogen carbonate (16 ml) was added. Solid sodium hydrogen carbonate was added until pH 7. The phases were separated. The aqueous phase was extracted with dichlormethane (2×50 ml). The combined organic layers were dried over magnesium sulfate. The solvent was removed in vacuo. The crude product was purified by flash chromatography on silica (80 g), using dichloromethane/methanol/25% aqueous ammonia (100:10:1) as eluent to give 436 mg of the title compound.

¹H-NMR (CDCl₃, selected values): d 1.10 and 1.11 (both s, together 6 H); 2.85, 3.13, 3.15, and 3.50 (all s, together 6 H); 5.89 and 5.97 (both dd, together 1 H); 6.23 and 6.24 (both d, together 1 H).

MS: 486.4; [M+1]⁺

HPLC: 36.62 min (A1)

38.93 min (B1).

For biological testing, the title compound was transferred into its acetate salt by lyophilization from 0.5M aqueous acetic acid (50 ml).

Example 7

(2R)-2-(N-(3-(1-Aminoethyl)benzoyl)-N-methylamino)-N-methyl-3-(2-naphthyl)-N-(2-(2-thienyl)ethyl)propionamide

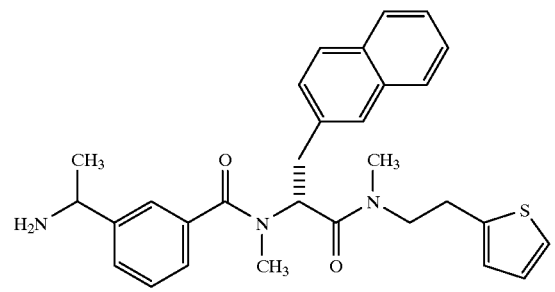

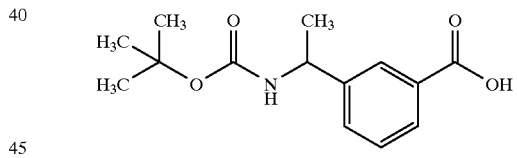

Ammonium acetate (10.6 g, 138 mmol) was evaporated from dry ethanol (100 ml), and re dissolved in dry methanol (100 ml) over molecular sieves (3 Å, 3 g). 3-Acetylbenzonitrile (2.0 g, 13.8 mmol) was added. After 30 min at room temperature sodium cyanoborohydride (0.87 g, 138 mmol) was added and eth reaction mixture was stirred for 18 h. The reaction mixture was concentrated in vacuo and redissolved in water (100 ml). Concentrated hydrochloric acid was added until pH 2, and the aqueous solution was extracted with ethyl acetate (2×100 ml). The aqueous phase was adjusted to pH 11 with solid potassium hydroxide, and extrcted with dichloromethane (2×100 ml). The combined organic phases were dried (magnesium sulfae) and concentrated in vacuo. A concentrated solution of hydrogen chloride in ethyl acetate (100 ml) was added, and the solution was concentrated in vacuo. The residue was dissolved in ethanol (25 ml) and sulfuric acid (9N, 25 ml) was added. After 16 h at room temperature and 2 h at reflux temperature, the ethanol was removed by evaporation in vacuo and the residual aqueous mixture was adjusted to pH >8, using solid potassium hydroxide. Di-tert.-butyldicarbonate (2.0 g), dissolved in tetrahydrofuran (100 ml) was added at 0° C. After 18 h at room temperature, the reaction mixture was concentrated in vacuo and redissolved in water (100 ml). Solid citric acid was added until pH 5. The reaction mixture was extracted with dichloromethane (2×100 ml), and the combined organic phases were dried (magnesium sulfae) and concentrated in vacuo. The residue was purified by column chromatography on silica gel (3×40 cm), using ethanol and dichloromethane (1:9) as eluent to give 1.1 g of 3-(1-(N-tert.-butoxycarbonyl)aminoethyl)benzoic acid.

(1-(3-(N-Methyl-N-((1R)-1-(N-methyl-N-(2-(2-thienyl)ethyl)carbamoyl)-2-(2-naphthyl)ethyl)carbamoyl)phenyl)ethyl)carbamic acid tert-butyl ester

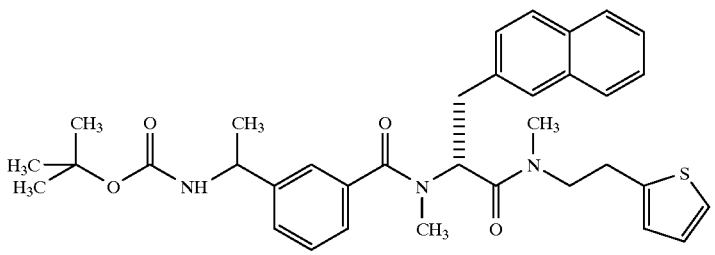

3-(1-(t-Butyloxycarbonylamino)ethyl)benzoic acid (217 mg, 0.82 mmol) was dissolved in dichloromethane (5 ml) and N,N-dimethylformamide (3 ml). 1-Hydroxy-7-azabenzotriazole (111 mg, 0.82 mmol) was added. The solution was cooled to 0° C. N-(3-Dimethylaminopropyl)-N'-ethylcarbodiimide hydrochloride (157 mg, 0.82 mmol) was added. A solution of (2R)-N-Methyl-2-(methylamino)-3-(2-naphthyl)-N-(2-(2-thienyl)ethyl)propionamide (288 mg, 0.82 mmol) in dichloromethane (3 ml) was added. Ethyldiisopropylamine (0.14 ml, 0.82 mmol) was added. The reaction mixture was stirred for 16 h, while it was warming up to room temperature. It was diluted with ethyl acetate (80 ml) and washed with 10% sodium hydrogen sulfate solution (50 ml). The aqueous phase was extracted with ethyl acetate (2×40 ml). The combined organic layers were washed with saturated sodium hydrogen carbonate solution (50 ml) and dried over magnesium sulfate. The solvent was removed in vacuo. The crude product was purified by flash chromatography on silcia (110 g), using ethyl acetate/heptane 1:1 as eluent, to give 479 mg of (1-(3-(N-methyl-N-((1R)-1-(N-methyl-N-(2-(2-thienyl)ethyl)carbamoyl)-2-(2-naphthyl)ethyl)carbamoyl)phenyl)ethyl)carbamic acid tert-butyl ester.

¹H-NMR (CDCl₃, selected peaks): d 1.43 (br, 9 H); 5.91 and 6.02 (both dd, together 1 H).

MS: 600.0 [M+H]⁺.

(1-(3-(N-Methyl-N-((1R)-1-(N-methyl-N-(2-(2-thienyl)ethyl)carbamoyl)-2-(2-naphthyl)ethyl)carbamoyl)phenyl)ethyl)carbamic acid tert-butyl ester (479 mg, 0.80 mmol) was dissolved in dichloromethane (2 ml) and cooled to 0° C. Trifluoroacetic acid (2 ml) was added. The reaction mixture was stirred for 35 min at 0° C. It was diluted with dichloromethane (8 ml). Saturated sodium hydrogen carbonate solution (10 ml) was added carefully. Solid sodium hydrogen carbonate was added until pH 7. Water was added, until a clear solution was obtained. The phases were separated, and the aqueous phase was extracted with dichloromethane (2×50 ml). The combined organic layers were dried over magnesium sulfate. The solvent was removed in vacuo. The crude product was purified by flash chromatography on silica (70 g), using dichloromethane/methanol/25% aqueous ammonia as eluent, to give 293 mg of the title compound.

¹H-NMR (CDCl₃, selected peaks): d 1.15 and 1.27 (both d, together 3 H); 2.87 (s, 3 H); 3.00 and 3.03 (both s, together 3 H); 5.90 and 6.00 (both dd, together 1 H).

MS: 500.0 [M+H]⁺.

HPLC: 34.30 (A1).

36.85 (B1).

For biological testing, the title compound was transferred into its acetate salt, by lyophilization from 0.5N acetic acid (50 ml).

Example 8

(2E)-5-Amino-5-methylhex-2-enoic acid N-((1R)-2-(1,2,3,4-tetrahydroisoquinolin-2-yl)-1 ((2-naphthyl)methyl)-2-oxoethyl)-N-methylamide

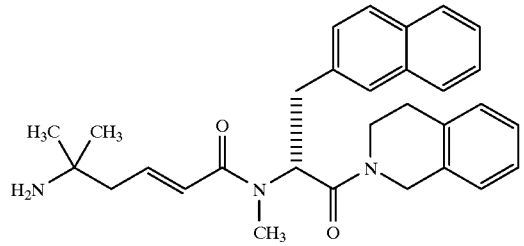

N-((1R)-2-(1,2,3,4-Tetrahydroisoquinolin-2-yl)-1-((2-naphthyl)methyl)-2-oxoethyl)-N-methylcarbamic acid tert-butyl ester

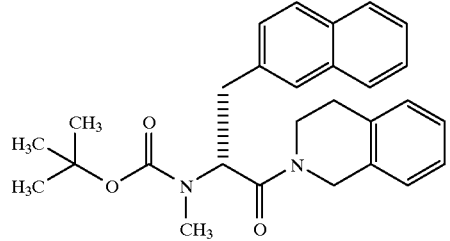

(2R)-2-(N-(tert-Butoxycarbonyl)-N-methylamino)-3-(2-naphthyl)propionic acid (7.41 g, 22.5 mmol) was dissolved in N,N-dimethylformamide (90 ml) and dichloromethane (110 ml). 1-Hydroxy-7-azabenzotriazole (3.06 g, 22.5 mmol) was added. The mixture was cooled to 0° C. N-(3-Dimethylaminopropyl)-N'-ethylcarbodiimide hydrochloride (4.32 g, 22.5 mmol) was added. The solution was stirred for 15 min at 0° C. 1,2,3,4-Tetrahydroqunoline (3.00 g, 22.5 mmol) and ethyldiisopropylamine (3.90 m., 22.5 mmol) were added. The reaction mixture was stirred for 16 h, while it was warming up to room temperature. It was diluted with ethyl acetate (80 ml) and extracted with 10% aquoeous sodium hydrogen sulfate solution (250 ml). The aqueous phase was extracted with ethyl acetate (3×60 ml). The combined organic layers were washed with saturated sodium hydrogen carbonate solution (200 ml) and dried over magnesium sulfate. The solvent was removed in vacuo. The crude product was purified by flash chromatography on silica (130 g), using ethyl acetate/heptane 1:2 as eluent to give 6.12 g of N-((1R)-2-(1,2,3,4-tetrahydroisoquinolin-2-yl)-1-((2-naphthyl)methyl)-2-oxoethyl)-N-methylcarbamic acid tert-butyl ester.

$^1$H-NMR (CDCl$_3$, selected values): d 1.07, 1.22, and 1.28 (all s, together 9 H); 5.14 and 5.50 (m and q, together 1 H); 6.90–7.85 (m, together 11 H).

MS: 445.0 ([M+1]$^+$).

mp: 121–126° C. (ethyl acetate/heptane).

C$_{28}$H$_{32}$N$_2$O$_3$ (444.57)

calc. C 75.65 H 7.26 N 6.03
found C 75.92 H 7.53 N 6.07

(2R)-1-(1,2,3,4-Tetrahydroisoquinolin-2-yl)-2-(methylamino)-3-(2-naphthyl)-1-propanone

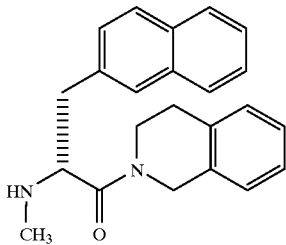

N-((1R)-2-(1,2,3,4-Tetrahydroisoquinolin-2-yl)-1-((2-naphthyl)methyl)-2-oxoethyl)-N-methylcarbamic acid tert-butyl ester (6.12 g, 13.8 mmol) was dissolved in dichloromethane (40 ml). The solution was cooled to 0° C. Trifluoroacetic acid (40 ml) was added. The reaction mixture was stirred for 90 min at 0° C. Dichloromethane (110 ml) and a saturated aqueous solution of sodium hydrogen carbonate (150 ml) were added successively. Solid sodium hydrogen carbonate was added until pH 7 was obtained. The phases were separated. The aqueous phase was extracted with dichloromethane (3×60 ml). The combined organic layers were dried over magnesium sulfate. The solvent was removed in vacuo. The crude product was purified by flash chromatography on silica (130 g), using dichloromethane/methanol/25% aqueous ammonia 100:10:1 as eluent, to give 2.20 g of (2R)-1-(1,2,3,4-tetrahydroisoquinolin-2-yl)-2-(methylamino)-3-(2-naphthyl)-1-propanone.

$^1$H-NMR (CDCl$_3$, selected values): d 2.34 and 2.35 (both s, together 3 H); 4.36 and 4.85 (both d, together 1 H); 6.55–7.80 (m, together 11 H).

MS: 345.2 ([M+1]$^+$).

((3E)-4-(N-((1R)-2-(1,2,3,4-Tetrahydroisoquinolin-2-yl)-1-((2-naphthyl)methyl)-2-oxoethyl)-N-methylcarbamoyl)-1,1-dimethylbut-3-enyl)carbamic acid tert-butyl ester

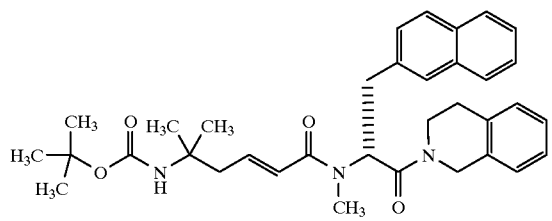

(2E)-5-(tert-Butoxycarbonylamino)-5-methylhex-2-enoic acid (283 mg, 1.16 mmol) was dissolved in N,N-dimethylformamide (5.5 ml) and dichloromethane (6.5 ml). 1-Hydroxy-7-azabenzotriazole (158 mg, 1.16 mmol) was added. The mixture was cooled to 0° C. N-(3-Dimethylaminopropyl)-N'-ethylcarbodiimide hydrochloride (223 mg, 1.16 mmol) was added. The reaction mixture was stirred for 15 min at 0° C. A solution of (2R)-1-(1,2,3,4-tetrahydroisoquinolin-2-yl)-2-(methylamino)-3-(2-naphthyl)-1-propanone (400 mg, 1.16 mmol) in dichloromethane (4 ml) and ethyldiisopropylamine (0.2 ml, 1.16 mmol) were added successively. The reaction mixture was stirred for 16 h, while it was warming up to room temperature. I was diluted with ethyl acetate (60 ml) and washed with 10% aqueous sodium hydrogen sulfate solution (60 ml). The aqueous phase was extracted with ethyl acetate (3×50 ml). The combined organic layers were washed with saturated sodium hydrogen carbonate solution (100 ml) and dried over magnesium sulfate. The solvent was removed in vacuo. The crude product was purified by flash chromatography on silica (80 g), using ethyl acetate/heptane 1:1 as eluent to give 647 mg of ((3E)-4-(N-((1R)-2-(1,2,3,4-tetrahydroisoquinolin-2-yl)-1-((2-naphthyl)methyl)-2-oxoethyl)-N-methylcarbamoyl)-1,1-dimethylbut-3-enyl) carbamic acid tert-butyl ester.

$^1$H-NMR (CDCl$_3$, selected values): d 1.25 and 1.40 (m and s, together 15 H); 2.97 and 3.09 (both s, together 3 H); 6.00 (t, 1 H); 6.07 and 6.23 (both d, together 1 H); 6.65–7.85 (m, together 13 H).

((3E)-4-(N-((1R)-2-(1,2,3,4-Tetrahydroisoquinolin-2-yl)-1-((2-naphthyl)methyl)-2-oxoethyl)-N-methylcarbamoyl)-1,1-dimethylbut-3-enyl)carbamic acid tert-butyl ester (647 mg, 1.14 mmol) was dissolved in dichloromethane (3 ml). The solution was cooled to 0° C. Trifluoroacetic acid (3 ml) was added. The reaction mixture was stirred for 35 min at 0° C. Dichloromethane (12 ml) and a saturated aqueous solution of sodium hydrogen carbonate (14 ml) were added. Solid sodium hydrogen carbonate was added until pH 7 was obtained. The phases were separated. The aqueous phase was extracted with dichloromethane (3×50 ml). The combined organic layers were dried over magnesium sulfate. The solvent was removed in vacuo. The crude product was purified by flash chromatography on silica (80 g), using dichloromethane/methanol/25% aqueous ammonia 100:10:1 as eluent, to give 234 mg of the title compound.

$^1$H-NMR (CDCl$_3$, selected values): d 1.08 and 1.10 (both s, together 6 H); 2.20 and 2.25 (both d, together 2 H); 2.96 and 3.08 (both s, together 3 H); 5.98 (m,1 H); 6.06 and 6.23 (both d, together 1 H); 6.70–7.80 (m, 12 H).

MS: 470 ([M+1]$^+$).

HPLC 33.48 min (A1).

35.43 min (B1).

For biological testing, the title compound was transferred into its acetate salt by lyophilization with 0.5M acetic acid (50 ml).

Example 9

(2E)-5-Methyl-N-methyl-5-(methylamino)-N-((1R)-1-(N-methyl-N-phenethylcarbamoyl)-2-(2-naphthyl)ethyl)hex-2-enamide

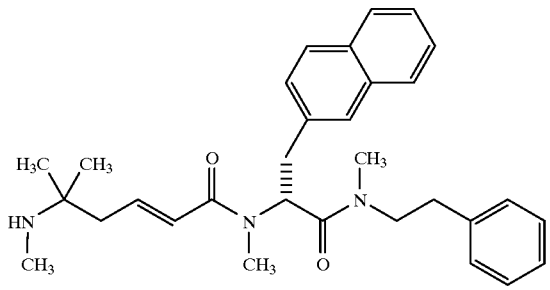

N-Methyl-N-((3E)-4-(N-methyl-N-((1R)-1-(N-methyl-N-phenethylcarbamoyl)-2-(2-naphthyl)ethyl)carbamoyl)-1,1-dimethylbut-3-enyl)carbamic acid tert-butyl ester

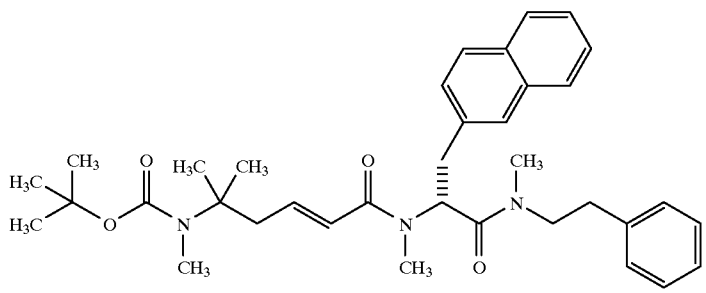

(2E)-5-(N-(tert-Butoxycarbonyl)-N-methylamino)-5-methylhex-2-enoic acid (122 mg, 0.48 mmol) was dissolved in N,N-dimethylformamide (2 ml) and dichloromethane (2 ml). 1-Hydroxy-7-azabenzotriazole 0(65 mg, 0.48 mmol) was added. The solution was cooled to 0° C. N-(3-Dimethylaminopropyl)-N'-ethylcarbodiimide hydrochloride (92 mg, 0.48 mmol) was added. The reaction mixture was stirred for 15 min at 0° C. A solution of (2R)-2-(methylamino)-3-(2-naphthyl)propionic acid N-methyl-N-phenethylamide (165 mg, 0.48 mmol) in dichloromethane (2 ml) and ethyldiisopropylamine (0.083 ml, 0.48 mmol) were added successively. The solution was stirred for 16 h, while it was warming up to room temperature. It was diluted with ethyl acetate (50 ml) and washed with 10% aqueous sodium hydrogen sulfate solution (50 ml). The aqueous phase was extracted with ethyl acetate (2×10 ml). The combined organic layers were washed with saturated aqueous sodium hydrogen carbonate solution (50 ml) and dried over magnesium sulfate. The solvent was removed in vacuo. The crude product was purified by flash chromatography on silica (80 g), using ethyl acetate/heptane 1:1 as eluent to give 204 mg of N-methyl-N-((3E)-4-(N-methyl-N-((1R)-1-(N-methyl-N-phenethylcarbamoyl)-2-(2-naphthyl)ethyl)carbamoyl)-1,1-dimethylbut-3-enyl)carbamic acid tert-butyl ester.

$^1$H-NMR (CDCl$_3$, selected values): d 0.90 and 0.92 (both s, together 6 H); 5.80 and 5.86 (t and dd, together 1 H); 6.12 and 6.21 (both d, together 1 H); 6.80 (m, 1 H); 7.00–7.85 (m, 12 H).

N-Methyl-N-((3E)-4-(N-methyl-N-((1R)-1-(N-methyl-N-phenethylcarbamoyl)-2-(2-naphthyl)ethyl)carbamoyl)-1,1-dimethylbut-3-enyl)carbamic acid tert-butyl ester (182 mg, 0.31 mmol) was dissolved in dichloromethane (2 ml). The solution was cooled to 0° C. Trifluoroacetic acid (2 ml) was added. The reaction mixture was stirred at 0° C. for 20 min. It was diluted with dichloromethane (50 ml). A saturated aqueous solution of sodium hydrogen carbonate (10 ml) was added. Solid sodium hydrogen carbonate was added until pH 7 was obtained. The phases were separated. The aqueous phase was extracted with dichloromethane (2×15 ml). The combined organic layers were dried over magnesium sulfate. The solvent was removed in vacuo. The crude product was purified by flash chromatography on silica (45 g), using dichloromethane/methanol/25% aqueous ammonia 100:10:1 as eluent to give 80 mg of the title compound.

$^1$H-NMR (CDCl$_3$, selected values): d 1.00 and 1.06 (both s, together 6 H); 2.25 and 2.31 (both s, together 3 H); 2.76, 2.87, and 3.05 (all s, together 6 H); 5.77 and 5.85 (t and dd, together 1 H); 6.14 and 6.23 (both d, together 1 H); 6.78 (m, 1 H); 7.00–7.90 (m, 12 H).

HPLC
34.30 min (A1).
36.28 min (B1).

MS: 486.0 ([M+1]$^+$).

For biological testing, the title compound was transferred into its acetate salt by lyophilization with 0.5M acetic acid (50 ml).

Example 10

(2R)-2-(N-((2E)-5-Amino-5-methylhex-2-enoyl)-N-methylamino)-N-(2-(2-(2-hydroxyethoxy)phenyl)ethyl)-N-methyl-3-(2-naphthyl)propionamide

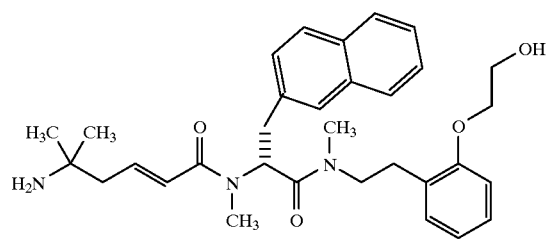

2-(2-Hydroxyphenyl)-N-methylacetamide

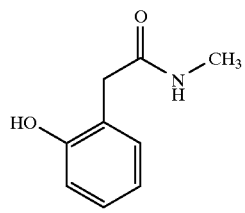

(2-Hydroxyphenyl)acetic acid (9.89 g, 63.7 mmol) and 1-hydroxybenzotriazole hydrate (8.61 g, 63.7 mmol) were dissolved in N,N-dimethylformamide (50 ml) and dichloromethane (200 ml). The solution was cooled to 0° C. N-(3-Dimethylaminopropyl)-N'-ethylcarbodiimide hydrochloride (8.67 g, 63.7 mmol) was added. The reaction mixture was stirred for 30 min at 0° C. A 8.0M solution of methyl amine (39 ml, 318 mmol) was added. The reaction mixture was stirred for 16 h, while it was slowly warming up to room temperature. It was diluted with ethyl acetate (600 ml) and washed with a 10% aqueous solution of sodium hydrogen sulfate (2×300 ml). The combined aqueous phases were extracted with ethyl acetate. The combined organic layers were washed with saturated sodium hydrogen carbonate solution (300 ml) and dried over magnesium sulfate. The solvent was removed in vacuo. The crude product was purified by flash chromatography on silica (180 g), using ethyl acetate/heptane (1:1) as eluent to give 4.90 g of 2-(2-hydroxyphenyl)-N-methylacetamide.

mp: 105–106° C. (ethyl acetate/heptane).

$^1$H-NMR (CDCl$_3$): d 2.82 (d, 3 H); 3.56 (s, 2 H); 6.20 (br, 1 H); 6.83 (m, 1 H); 7.00 (m, 2 H); 7.18 (m, 1 H); 9.85 (s, 1 H).

Ethyl 2-(2-((N-methylcarbamoyl)methyl)phenoxy)acetate

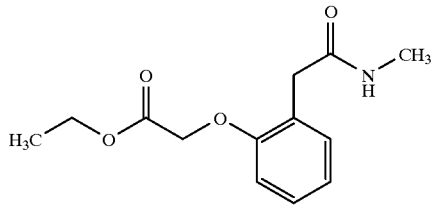

Potassium carbonate (2.81 g, 20.34 mmol) was given to a solution of 2-(2-hydroxyphenyl)-N-methylacetamide (3.36 g, 20.34 mmol) in acetone (150 ml). Ethyl bromoacetate (2.13 ml, 19.32 mmol) and potassium iodide (166 mg, 1.02 mmol) were added successively. The reaction mixture was heated to reflux for 6 h. It was left at room temperature for 16 h. The solid was filtered off. The solvent was removed in vacuo. The crude product was purified by flash chromatography on silica (80 g), using ethyl acetate/dichloromethane (1:1) as eluent, to give 5.00 g of ethyl 2-(2-((N-methylcarbamoyl)methyl)phenoxy)acetate.

$^1$H-NMR (CDCl$_3$): d 1.33 (t, 3 H); 2.74 (d, 3 H); 3.61 (s, 2 H); 4.30 (q, 2 H); 4.70 (s, 2 H); 6.68 (br, 1 H); 6.76 (d, 1 H); 6.98 (t, 1 H); 7.24 (t, 1 H); 7.32 (d, 1 H).

2-(2-(2-(Methylamino)ethyl)phenoxy)ethanol

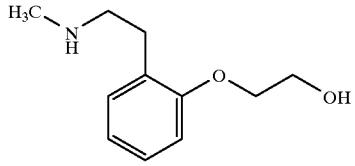

At 0° C. a solution of ethyl 2-(2-((N-methylcarbamoyl)methyl)phenoxy)acetate (5.00 g, 19.9 mmol) in tetrahydrofuran (75 ml) was added dropwise to a suspension of sodium borohydride (2.26 g, 59.7 mmol) in tetrahydrofuran (75 ml). A solution of iodine (5.05 g, 19.9 mmol) in tetrahydrofuran (150 ml) was added dropwise. The solution was warmed to room temperature and heated to reflux for 16 h. It was cooled to 0° C. Methanol (150 ml) was added dropwise. The solvent was removed in vacuo. The solid residue was dissolved in 20% aqueous sodium hydroxide solution/tert-butyl methyl ether (150 ml/150 ml). The phases were separated. The aqueous phase was extracted with tert-butyl methyl ether (3×150 ml). The combined organic layers were dried over magnesium sulfate. The solvent was removed in vacuo. The crude product was purified by flash chromatography on silica (80 g), using dichloromethane/methanol/10% aqueous ammonia (first: 100:10:1, then 70:30:3) as eluent, to give 1.124 g of 2-(2-(2-(Methylamino)ethyl)phenoxy)ethanol.

$^1$H-NMR (CDCl$_3$): d 2.40 (s, 3 H); 2.82 (m, 2 H); 2.92 (m, 2 H); 3.05 (br, 2 H); 3.94 (m, 2 H); 4.10 (m, 2 H); 6.87 (d, 1 H); 6.92 (t, 1 H); 7.17 (m, 2 H).

N-((1R)-1-(N-(2-(2-(2-Hydroxyethoxy)phenyl)ethyl)-N-methylcarbamoyl)-2-(2-naphthyl)ethyl)-N-methylcarbamic acid tert-butyl ester

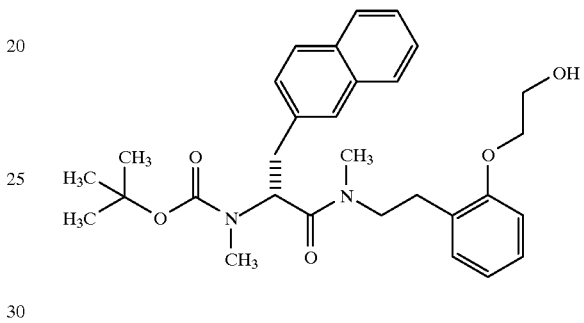

At 0° C. N-(3-Dimethylaminopropyl)-N'-ethylcarbodiimide hydrochloride (558 mg, 2.91 mmol) was given to a solution of (2R)-2-(N-(tert-butoxycarbonyl)-N-methylamino)-3-(2-naphthyl)propionic acid (959 g, 2.91 mmol) and 1-Hydroxy-7-azabenzotriazole (396 mg, 2.91 mmol) in N,N-dimethylformamide (5 ml) and dichloromethane (5 ml). The solution was stirred for 20 min at 0° C. A solution of 2-(2-(2-(Methylamino)ethyl)phenoxy)ethanol (608 mg, 2.91 mmol) in dichloromethane (5 ml) and ethyldiisopropylamine (0.50 ml, 2.91 mmol) were added successively. The reaction mixture was stirred for 16 h, while it was warming up to room temperature. It was diluted with ethyl acetate (150 ml) and washed with a 10% aqueous sodium hydrogen sulfate solution (70 ml). The aqueous phase was extracted with ethyl acetate (2×30 ml). The combined organic layers were washed with saturated sodium hydrogen carbonate soltuion (150 ml) and dried over magnesium sulfate. The solvent was removed in vacuo. The crude product was purified by flash chromatography on silica (110 g), using ethyl acetate/heptane (1:1) as eluent, to give 1.02 g of N-((1R)-1-(N-(2-(2-(2-hydroxyethoxy)phenyl)ethyl)-N-methylcarbamoyl)-2-(2-naphthyl)ethyl)-N-methylcarbamic acid tert-butyl ester.

$^1$H-NMR (CDCl$_3$, selected values): d 1.00, 1.22, and 1.29 (all s, together 9 H); 4.88, 5.02, 5.20, and 5.39 (t, m, q, and t, together 2 H).

MS: 507.2 ([M+H]$^+$).

(2R)-N-(2-(2-(2-Hydroxyethoxy)phenyl)ethyl)-N-methyl-2-(methylamino)-3-(2-naphthyl)propionamide

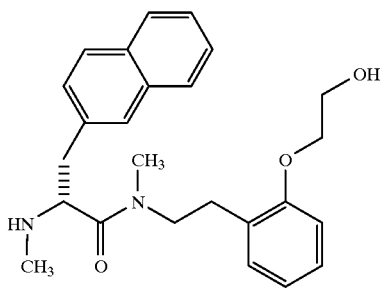

At 0° C., trifluoroacetic acid (4 ml) was added to a solution of N-((1R)-1-(N-(2-(2-(2-hydroxyethoxy)phenyl)ethyl)-N-methylcarbamoyl)-2-(2-naphthyl)ethyl)-N-methylcarbamic acid tert-butyl ester (986 mg, 1.95 mmol) in dichloromethane (4 ml). The solution was stirred for 3 h at 0° C. Dichloromethane (50 ml) was added. A saturated solution of sodium hydrogen carbonate (30 ml) was added. Solid sodium hydrogen carbonate was added until pH 7 was obtained. Water was added until a clear solution was obtained. The phases were separated. The aqueous phase was extracted with dichloromethane (2×20 ml). The combined organic layers were dried over magnesium sulfate. The solvent was removed in vacuo. The crude product was purified by flash chromatography on silica (80 g), using dichloromethane/methanol/25% aqueous ammonia (100:10:1) as eluent, to give 730 mg of (2R)-N-(2-(2-(2-hydroxyethoxy)phenyl)ethyl)-N-methyl-2-(methylamino)-3-(2-naphthyl)propionamide.

$^1$H-NMR (CDCl$_3$, selected values): d 2.25 and 2.30 (both s, together 3 H); 2.50 and 2.89 (both s, together 3 H).

(3E)-4-(N-((1R)-1-(N-(2-(2-(2-Hydroxyethoxy)phenyl) ethyl)-N-methylcarbamoyl)-2-(2-naphthyl)ethyl)-N-methylcarbamoyl)-1,1-dimethylbut-3-enylcarbamic acid tert-butyl ester ethyl acetate (2×50 ml). The combined organic layers were washed with saturated aqueous sodium hydrogen carbonate solution (200 ml) and dried over magnesium sulfate. The solvent was removed in vacuo. The crude product was purified by flash chromatography on silica (60 g), using ethyl acetate/heptane (first: 2:1 (500 ml), then: 3:1) as elutent, to give 378 mg of (3E)-4-(N-((1R)-1-(N-(2-(2-(2-hydroxyethoxy)phenyl)ethyl)N-methylcarbamoyl)-2-(2-naphthyl)ethyl)-N-methylcarbamoyl)-1,1-dimethylbut-3-enylcarbamic acid tert-butyl ester.

$^1$H-NMR (CDCl$_3$, selected values): d 1.32 and 1.40 (both s, together 9 H); 2.91 and 2.97 (both s, together 3 H); 3.02 and 3.05 (both s, together 3 H); 4.80 and 4.90 (both t, together 1 H); 5.69 and 5.87 (both dd, together 1 H); 6.05 and 6.22 (both d, together 1 H).

(3E)-4-(N-((1R)-1-(N-(2-(2-(2-Hydroxyethoxy)phenyl) ethyl)-N-methylcarbamoyl)-2-(2-naphthyl)ethyl)-N-methylcarbamoyl)-1,1-dimethylbut-3-enylcarbamic acid tert-butyl ester (347 mg, 0.55 mmol) was dissolved in dichloromethane (3 ml). The solution was cooled to 0° C. Trifluoroacetic acid (3 ml) was added. The reaction mixture was stirred at 0° C. for 30 min. A saturated aqueous solution of sodium hydrogen carbonate (6 ml) was added dropwise. Solid sodium hydrogen carbonate was added until pH 7 was obtained. The phases were separated. The aqueous phase was extracted with dichloromethane (2×30 ml). The combined organic layers were dried over magnesium sulfate. The solvent was removed in vacuo. The crude product was purified by flash chromatography on silica (15 g), using dichloromethane/methanol/25% aqueous ammonia (first: 100:10:1, then: 50:10:1) as eluent, to give 218 mg of the title compound.

$^1$H-NMR (CDCl$_3$, selected values): d 1.04 and 1.12 (both s, together 6 H); 2.93, 2.99, 3.02, and 3.07 (all s, together 6 H); 5.68 and 5.87 (both dd, together 1 H); 6.05 and 6.25 (both d, together 1 H).

MS: 532.2 ([M+H]$^+$).

HPLC:

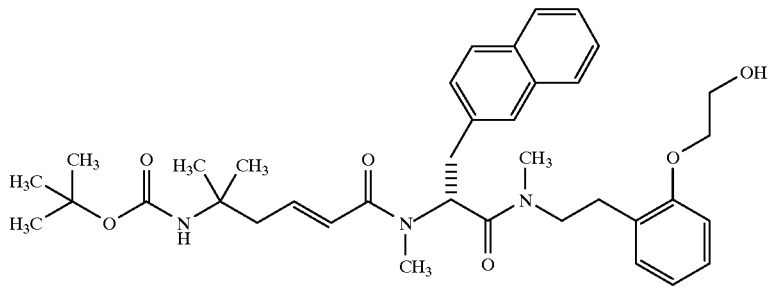

At 0° C. N-(3-Dimethylaminopropyl)-N'-ethylcarbodiimide hydrochloride (125 mg, 0.65 mmol) was added to a solution of (2E)-5-(tert-butoxycarbonylamino)-5-methylhex-2-enoic acid (158 mg, 0.65 mmol) and 1-hydroxy-7-azabenzotriazole (88 mg, 0.65 mmol) in N,N-dimethylformamide (3 ml) and dichloromethane (3 ml). The solution was stirred for 20 min at 0° C. A solution of (2R)-N-(2-(2-(2-hydroxyethoxy)phenyl)ethyl)-N-methyl-2-(methylamino)-3-(2-naphthyl)propionamide (265 mg, 0.65 mmol) in dichlromethane (3 ml) and ethyldiisopropylamine (0.11 ml, 0.65 mmol) were added successively. The reaction mixture was stirred for 16 h, while it was warming up to room temperature. It was diluted with ethyl acetate (200 ml) and washed with 10% aqueous sodium hydrogen sulfate solution (100 ml). The aqueous phase was extracted with 32.75 min (A1).

33.82 min (B1).

For biological testing, the title compound was transferred into its acetate salt by lyophilization with 0.5M acetic acid (50 ml).

Example 11

(2R)-2-(N-((2E)-5-Amino-5-methylhex-2-enoyl)-N-methylamino)-N-methyl-3-(2-naphthyl)-N-(2-(2-methylsulfonylaminophenyl)ethyl)propionamide

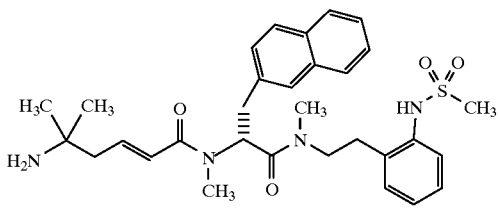

N-Methyl-2-(2-nitrophenyl)acetamide

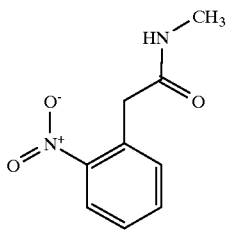

(2-Nitrophenyl)acetic acid (10.0 g, 55.21 mmol) was dissolved in N,N-dimethylformamide (15 ml) and dichloromethane (50 ml). 1-Hydroxybenzotriazole hydrate (7.46 g, 55.21 mmol) was added. The solution was cooled to 0° C. N-(3-Dimethylaminopropyl)-N'-ethylcarbodiimide hydrochloride (10.58 g, 55.21 mmol) was added. The solution was stirred for 15 min at 0° C. A 8.0M solution of methylamine in ethanol (10.3 ml, 82.81 mmol) and ethyldiisopropylamine (9.55 ml, 55.21 mmol) were added successively. The reaction mixture was stirred for 16 h, while it was warming up to room temperature. It was diluted with ethyl acetate (180 ml) and washed with 10% aqueous sodium hydrogen sulfate solution (100 ml). The aqueous phase was extracted with ethyl acetate (2×40 ml). The combined organic layers were washed with saturated aqueous sodium hydrogen carbonate solution (200 ml) and dried over magnesium sulfate. The solvent was removed in vacuo. The crude product was purified by flash chromatography on silica (200 g), using dichloromethane/methanol/25% aqueous ammonia (100:10:1) as eluent to give 8.01 g of N-methyl-2-(2-nitrophenyl)acetamide.

mp: 147° C. (dichloromethane/methanol/25% aqueous ammonia).

$^1$H-NMR (CDCl$_3$) d 2.80 (d, 3 H); 3.82 (s, 2 H); 5.85 (br, 1 H); 7.40–7.65 (m, 3 H); 8.04 (d, 1 H).

MS: 388.8 ([2M+H]$^+$), 195.2 ([M+H]$^+$).

C$_9$H$_{10}$N$_2$O$_3$ (194.2)

calc.: C 55.62 H 5.19 N 14.43 found: C 55.86 H 5.30 N 14.39

N-Methyl-N-(2-(2-nitrophenyl)ethyl)amine

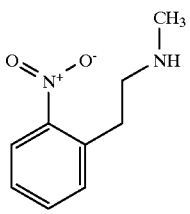

At 0° C., a solution of N-methyl-2-(2-nitrophenyl)acetamide (7.00 g, 36.05 mmol) in tetrahydrofuran (410 ml) was added dropwise to a suspension of sodium borohydride (1.63 g, 43.25 mmol) in tetrahydrofuran (110 ml). A solution of iodine (4.57 g, 18.02 mmol) in tetrahydrofuran (150 ml) was added dropwise. The reaction mixture was warmed to reflux for 16 h. It was cooled to 0° C. Methanol (310 ml) was added dropwise. The solvent was removed in vacuo. The residue was dissolved in 20% aqueous sodium hydoxide solution (300 ml) and tert-butyl methyl ether (200 ml). The phases were separated. The aqueous phase was extracted with tert-butyl methyl ether (2×100 ml). The combined organic layers were dried over magnesium sulfate. The solvent was removed in vacuo. The crude product was purified by flash chromatography on silica (160 g), using dichloromethane/methanol/25% aqueous ammonia (100:10:1) as eluent, to give 1.28 g of N-methyl-N-(2-(2-nitrophenyl)ethyl)amine.

$^1$H-NMR (CDCl$_3$) d 2.49 (s, 3 H); 2.50 (br, 1 H); 2.93 (t, 2 H); 3.12 (t, 2 H); 7.39 (m, 2 H); 7.55 (m, 1 H); 7.91 (d, 1 H).

MS: 181.2 ([M+H]$^+$).

N-Methyl-N-(2-(2-nitrophenyl)ethyl)carbamic acid tert-butyl ester

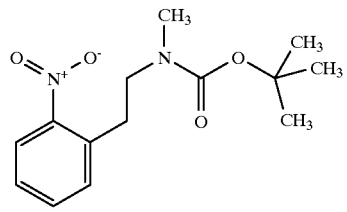

To a solution of N-methyl-N-(2-(2-nitrophenyl)ethyl)amine (529 mg, 2.9 mmol) in a 1N aqueous sodium hydroxide solution (2.9 ml, 2.9 mmol) and tetrahydrofuran (3.0 ml), a solution of di-tert-butyl dicarbonate(769 mg, 3.5 mmol) was added dropwise. The reaction mixture was stirred for 16 h at room temperature. It was diluted with water (50 ml) and ethyl acetate (50 ml). The phases were separated. The aqueous phase was extracted with ethyl acetate (3×50 ml). The combined organic layers were washed with saturated aqeous sodium hydrogen carbonate solution (50 ml) and dried over magnesium sulfate. The solvent was removed in vacuo. The crude product was purified by flash chromatography on silica (50 g), using ethyl acetate/heptane (1:1) as eluent, to give 924 mg of N-methyl-N-(2-(2-nitrophenyl)ethyl)carbamic acid tert-butyl ester.

$^1$H-NMR (CDCl$_3$) d 1.35 and 1.44 (both br, together 9 H); 2.85 (br, 3 H); 3.10 (br, 2 H); 3.56 (m, 2 H); 7.20–7.50 (br, 2 H); 7.55 (t, 1 H); 7.97 (br, 1 H).

N-(2-(2-Aminophenyl)ethyl)-N-methylcarbamic acid tert-butyl ester

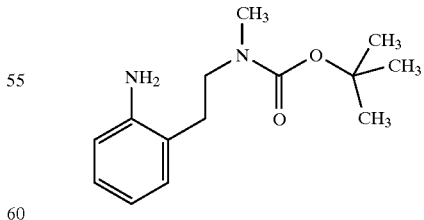

N-Methyl-N-(2-(2-nitrophenyl)ethyl)carbamic acid tert-butyl ester (924 mg, 3.3 mmol) was dissolved in ethanol (60 ml). 10% palladium on carbon (200 mg) was added. The mixture was hydrogenated at room temperature at 1 atmosphere for 16 h. The catalyst was filtered off through a plug of celite. The solvent was removed in vacuo. The crude product was purified by flash chromatography on silica (60 g), using ethyl acetate/heptane (1:2) as eluent, to give 723 mg of N-(2-(2-aminophenyl)ethyl)-N-methylcarbamic acid tert-butyl ester.

$^1$H-NMR (CDCl$_3$) d 1.47 (s, 9 H); 2.75 (t, 2 H); 2.90 (s, 3 H); 3.35 (br, 2 H); 3.71 (br, 1 H); 4.23 (br, 1 H); 6.68 (m, 2 H); 7.00 (d, 1 H); 7.05 (t, 1 H).

MS: 151.2 ([M+H]$^+$).

N-(2-(2-(Methylsulfonylamino)phenyl)ethyl)-N-methylcarbamic acid tert-butyl ester

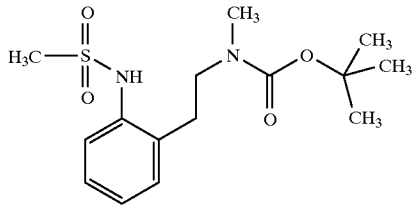

A solution of N-(2-(2-aminophenyl)ethyl)-N-methylcarbamic acid tert-butyl ester (723 mg, 2.9 mmol) and triethylamine (0.48 ml, 3.5 mmol) in dichloromethane (10 ml) was cooled to −78° C. A solution of methanesulfonyl chloride (0.22 ml, 2.9 mmol) in dichloromethane (2 ml) was added dropwise. The reaction mixture was stirred for 16 h, while it was warming up to room temperature. It was diluted with ethyl acetate (50 ml) and washed with 10% aqueos sodium hydrogen sulfate solution (150 ml). The aqueous phase was extracted with ethyl acetate (3×80 ml). The combined organic layers were washed with saturated aqueous sodium hydrogen carbonate solution (150 ml) and dried over magnesium sulfate. The solvent was removed in vacuo. The crude product was purified by flash chromatography on silica (60 g), using ethyl acetate/heptane (1:1) as eluent, to give 870 mg of N-(2-(2-(methylsulfonylamino)phenyl)ethyl)-N-methylcarbamic acid tert-butyl ester.

$^1$H-NMR (CDCl$_3$) d 1.50 (s, 9 H); 2.87 (m, 2 H); 2.91 (s, 3 H); 3.02 (s, 3 H); 3.30 (br, 2 H); 7.05–7.30 (m, 3 H); 7.57 (br, 1 H); 8.65 (br, 1 H).

N-(2-(2-(Methylamino)ethyl)phenyl)methanesulfonamide

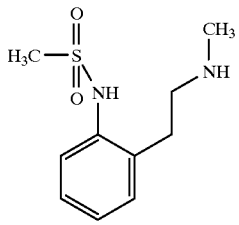

At 0° C., trifluoroacetic acid (6 ml) was added to a solution of N-(2-(2-(methylsulfonylamino)phenyl)ethyl)-N-methylcarbamic acid tert-butyl ester (870 mg, 2.6 mmol) in dichloromethane (6 ml). The reaction mixture was stirred for 50 min. Dichloromethane (24 ml) was added. A saturated aqueous solution of sodium hydrogen carbonate (34 ml) was added. Solid sodium hydrogen carbonate was added, until pH 7 was obtained. The phases were separated. The aqueous phase was extracted with dichloromethane (3×50 ml). The combined organic layers were dried over magnesium sulfate. The solvent was removed in vacuo. The crude product was purified by flash crhomatography on silica (60 g), using dichloromethane/methanol/25% aqueous ammonia (100:10:1) as eluent to give 308 mg of N-(2-(2-(methylamino)ethyl)phenyl)methanesulfonamide.

$^1$H-NMR (CDCl$_3$) d 2.51 (s, 3 H); 2.84 (m, 2 H); 2.94 (m, 2 H); 3.00 (s, 3 H); 5.70–6.70 (br, 1 H); 7.03 (m, 1 H); 7.12 (d, 1 H); 7.22 (t, 1 H); 7.53 (d, 1 H).

N-((1R)-1-(N-(2-(2-(Methylsulfonylamino)phenyl)ethyl)-N-methylcarbamoyl)-2-(2-naphthyl)ethyl)-N-methylcarbamic acid tert-butyl-ester

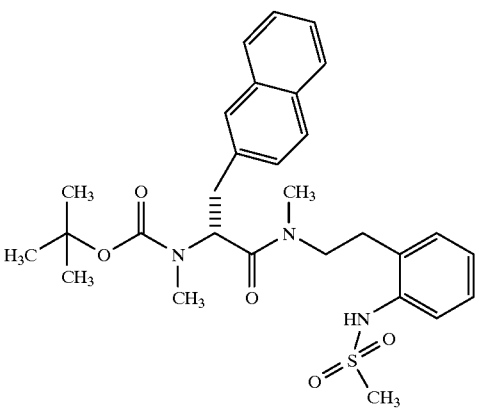

(2R)-2-(N-(tert-Butoxycarbonyl)-N-methylamino)-3-(2-naphthyl)propionic acid (444 mg, 1.35 mmol) and successively 1-hydroxy-7-azabenzotriazole (1 84 mg, 1.35 mmol) were dissolved in N,N-dimethylformamide (5 ml) and dichloromethane (7 ml). The solution was cooled to 0° C. N-(3-Dimethylaminopropyl)-N'-ethylcarbodiimide hydrochloride (259 mg, 1.35 mmol) was added. The reaction mixture was stirred for 15 min at 0° C. A solution of N-(2-(2-(methylamino)ethyl)phenyl)methanesulfonamide (308 mg, 1.35 mmol) was added. Ethyldiisopropylamine (0.23 ml, 1.35 mmol) was added. The reaction mixture was stirred for 16 h, while it was warming up to room temperature. It was diluted with ethyl acetate and washed with 10% aqueous sodium hydrogen sulfate solution (70 ml). The aqueous phase was extracted with ethyl acetate (2×50 ml). The combined organic layers were washed with a saturated aqueous solution of sodium hydrogen carbonate (150 ml) and dried over magnesium sulfate. The solvent was removed in vacuo. The crude product was purified by flash chromatography on silica (60 g), using ethyl acetateiheptane (1:1) as eluent, to give 245 mg of N-((1R)-1-(N-(2-(2-(methylsulfonylamino)phenyl)ethyl)-N-methylcarbamoyl)-2-(2-naphthyl)ethyl)-N-methylcarbamic acid tert-butyl-ester.

$^1$H-NMR (CDCl$_3$, selected values) d 1.15, 1.20, and 1.35 (all s, together 9 H); 4.83, 5.06, and 5.42 (all t, together 1 H); 8.07, 8.70, and 8.89 (all br, together 1 H).

MS: 540.0 ([M+H]$^+$).

(2R)-N-(2-(2-(Methylsulfonylamino)phenyl)ethyl)-N-methyl-2-(methylamino)-3-(2-naphthyl)propionamide

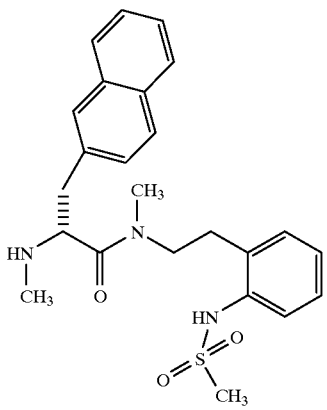

At 0° C., trifluoroacetic acid (1.5 ml) was added to a solution of N-((1R)-1-(N-(2-(2-(methylsulfonylamino)phenyl) ethyl)-N-methylcarbamoyl)-2-(2-naphthyl)ethyl)-N-methylcarbamic acid tert-butyl-ester (245 mg, 0.45 mmol) in dichloromethane (1.5 ml). The reaction mixture was stirred for 1.75 h at 0° C. Dichloromethane (5 ml) and a saturated aqueous solution of sodium hydrogen carbonate (6 ml) were added successively. Solid soidum hydrogen carbonate was added until pH 7 was obtained. The phases were separated. The aqueous phase was extracted with dichloromethane (3×50 ml). The combined organic layers were dried over magnesium sulfate. The solvent was removed in vacuo. The crude product was purified by flash chromatography on silica (30 g), using dichloromethane/methanol/25% aqueous ammonia (100:10:1) as eluent, to give 155 mg of (2R)-N-(2-(2-(methylsulfonylamino)phenyl)ethyl)-N-methyl-2-(methylamino)-3-(2-naphthyl)propionamide.

$^1$H-NMR (CDCl$_3$, selected values) d 2.35 and 2.51 (both s, together 3 H); 2.59 and 2.79 (both s, together 3 H); 2.94 and 3.07 (both s, together 3 H); 3.80 and 3.95 (dd and t, together 1 H).

((3E)-4-(N-((1R)-1-(N-(2-(2-(Methylsulfonylamino) phenyl)ethyl)-N-methylcarbamoyl)-2-(2-naphthyl)ethyl)-N-methylcarbamoyl)-1,1-dimethylbut-3-enyl)carbamic acid tert-butyl ester A solution of (2E)-5-(tert-butoxycarbonylamino)-5-methylhex-2-enoic acid (86 mg, 0.35 mmol) and 1-hydroxy-7-azabenzotriazole (48 mg, 0.35 mmol) in N,N-dimethylformamide (1.5 ml) and dichloromethane (1.8 ml) was cooled to 0° C. N-(3-Dimethylaminopropyl)-N'-ethylcarbodiimide hydrochloride (68 mg, 0.35 mmol) was added. The reaction mixture was stirred for 15 min at 0° C. A solution of (2R)-N-(2-(2-(methylsulfonylamino)phenyl) ethyl)-N-methyl-2-(methylamino)-3-(2-naphthyl) propionamide (155 mg, 0.35 mmol) in dichloromethane (2 ml) and ethyldiisopropylamine (0.06 ml, 0.35 mmol) were added successively. The reaction mixture was stirred for 16 h, while it was warming up to room temperature. It was diluted with ethyl acetate (50 ml) and washed with 10% aqueous sodium hydrogen sulfate solution (50 ml). The aqueous phase was extracted with ethyl acetate (3×20 ml). The combined organic layers were washed with saturated aqueous sodium hydrogen carbonate solution (50 ml) and dried over magnesium sulfate. The solvent was removed in vacuo. The crude product was purified by flash chromatography on silica (40 g), using ethyl acetate/heptane (2:1), as eluent, to give 174 mg of ((3E)-4-(N-((1R)-1-(N-(2-(2-(methylsulfonylamino)phenyl)ethyl)-N-methylcarbamoyl)-2-(2-naphthyl)ethyl)-N-methylcarbamoyl)-1,1-dimethylbut-3-enyl)carbamic acid tert-butyl ester.

$^1$H-NMR (CDCl3, selected values) d 5.58 and 5.88 (t and dd, together 1 H); 6.16 and 6.28 (both d, together 1 H); 6.87 (m, 1 H).

At 0° C. trifluoroacetic acid (2 ml) was given to a solution of ((3E)-4-(N-((1R)-1-(N-(2-(2-(methylsulfonylamino) phenyl)ethyl)-N-methylcarbamoyl)-2-(2-naphthyl)ethyl)-N-methylcarbamoyl)-1,1-dimethylbut-3-enyl)carbamic acid tert-butyl ester (168 mg, 0.25 mmol) in dichloromethane (2 ml). The reaction mixture was stirred at 0° C. for 40 min. A saturated aqueous solution of sodium hydrogen carbonate (6 ml) was added. Solid sodium hydrogen carbonate was added until pH 7 was obtained. Water was added, until a clear solution was obtained. The phases were separated. The aqueous phase wwas extracted with dichloromethane (3×20 ml). The combined organic layers were dried over magnesium sulfate. The solvent was removed in vacuo. The crude product was purified by flash chromatography on silica (15 g), using dichloromethanelmethanol/25% aqueous ammonia (100:10:1) as eluent to give 82 mg of the title compound.

$^1$H-NMR (CDCl$_3$, selected values) d 1.08 and 1.15 (both s, together 1 H); 2.93 and 2.95 (both s, together 3 H); 2.99 and 3.05 (both s, together 3 H); 3.12 and 3.13 (both s, together 3 H); 5.57 and 5.88 (t and dd, together 1 H); 6.18 and 6.30 (both d, together 1 H).

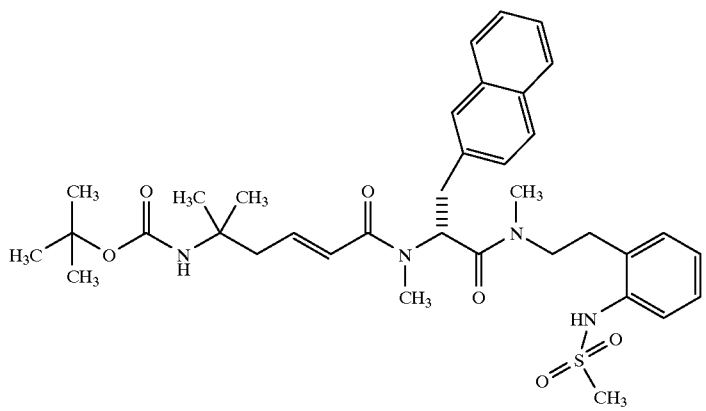

MS: 565.0 ([M+H]$^+$).
HPLC
32.08 min (A1).
32.53 min (B1).

For biological testing, the title compound was transferred into its acetate salt by lyophilization with 0.5M acetic acid (40 ml).

Example 12

(2E)-5-Amino-N-((1R)-2-(biphenyl-4-yl)-1-(N-methyl-N-(2-(2-thienyl)ethyl)carbamoyl)ethyl)-5-methyl-N-methylhex-2-enamide

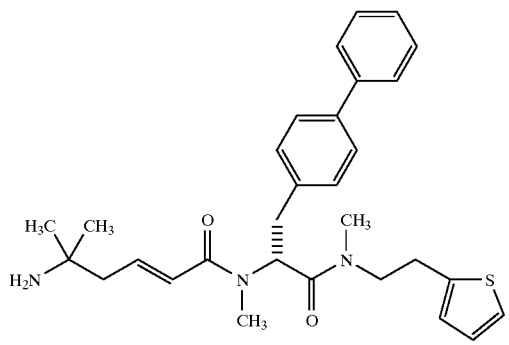

(2R)-3-(Biphenyl-4-yl)-2-(N-tert-butyoxcarbony)-N-methylamino)-propionic acid

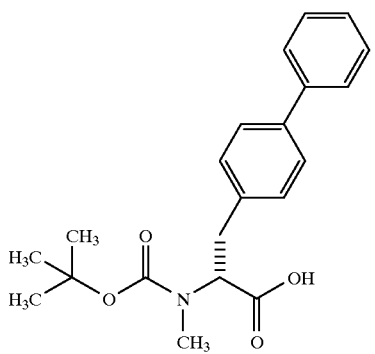

(2R)-3-(Biphenyl-4-yl)-2-(tert-butyoxcarbonylamino) propionic acid (5.0 g, 14.7 mmol) was dissolved in tetrahydrofurane (50 ml). Iodomethane (7.3 ml, 117.3 mmol) was added. The solution was cooled to 0° C. A 60% dispersion of sodium hydride in mineral oil (2.0 g, 44.0 mmol) was added portionwise. The reaction mixture was stirred for 8 days at room temperature. Tetrahydrofurane (100 ml) was added. The reaction mixture was cooled to 0° C. Methanol (50 ml) and successively water (20 ml) were added dropwise. The solvent was removed in vacuo. The resiude was dissolved in tert-butyl methyl ether (30 ml) and a saturated aqueous solution of sodium hydrogen carbonate (50 ml). The phases were separated. The aqueous phase was acidified to pH 3 with 5% aqueous citric acid. It was extracted with ethyl acetate (2×100 ml). These extracts were washed with a 5% aqueous sodium thiosulfate solution (2×100 ml) and with brine (100 ml). They were dried over magnesium sulfate. The solvent was removed in vacuo, to give 3.96 g of crude (2R)-3-(biphenyl-4-yl)-2-(N-(tert-butoxycarbonyl)-N-methylamino)-propionic acid, which was used for the further steps without purification.

$^1$H-NMR (DMSO d$^6$): d 1.24 and 1.29 (both s, together 9 H); 2.64 and 2.66 (both s, together 3 H); 2.95–3.40 (m, 2 H); 4.67 and 4.85 (both dd, together 1 H); 7.20–7.70 (m, 9 H); 12.83 (br, 1 H).

HPLC: 44.98 min (A1).

N-((1R)-2-(Biphenyl-4-yl)-1-(N-methyl-N-(2-(2-thienyl)ethyl)carbamoyl)ethyl)-N-methylcarbamic acid tert-butyl ester

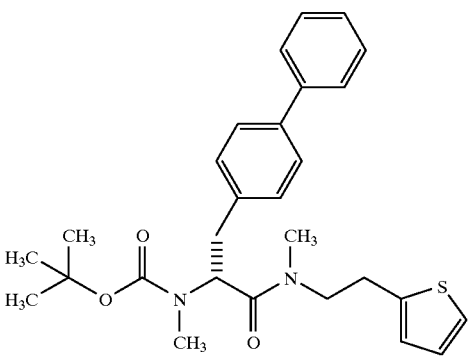

(2R)-3-(Biphenyl-4-yl)-2-(N-(tert-butoxycarbonyl)-N-methylamino)-propionic acid (753 mg, 2.12 mmol) and 1-hydroxy-7-azabenzotriazole (289 mg, 2.12 mmol) were dissolved in N,N-dimethylformamide (6 ml) and dichloromethane (6 ml). The solution was cooled to 0° C. N-(3-Dimethylaminopropyl)-N'-ethylcarbodiimide hydrochloride (406 mg, 2.12 mmol) was added. The solution was stirred for 15 min at 0° C. A solution of N-methyl-N-(2-(2-thienyl)ethyl)amine (300 mg, 2.12 mmol) in dichloromethane (6 ml) was added. Ethyldiisopropylamine (0.37 ml, 2.12 mmol) was added. The solution was stirred for 16 h, while it was warmin up to room temperature. It was diluted with ethyl acetate (300 ml) and washed with 10% aqueous sodium hydrogen sulfate solution (50 ml). The aqueous phase was extracted with ethyl acetate (3×20 ml). The combined organic layers were washed with a saturated aqueous sodium hydrogen carbonate solution (60 ml) and dried over magnesium sulfate. The solvent was removed in vacuo. The crude product was purified by flash chromatography on silcia (60 g), using ethyl acetate/heptane (1:2) as eluent to give 1.03 g of N-((1R)-2-(biphenyl-4-yl)-1-(N-methyl-N-(2-(2-thienyl)ethyl)carbamoyl)ethyl)-N-methylcarbamic acid tert-butyl ester.

$^1$H-NMR (CDCl$_3$, selected values): d 1.13, 1.21, 1.30, 1.36 (all s, together 9 H); 4.79, 4.97, and 5.31 (dd, dd, and m, together 1 H); 6.70–7.60 (m, 12 H).

(2R)-3-(Biphenyl-4-yl)-N-methyl-2-(methylamino)-N-(2-(2-thienyl)ethyl)propanamide

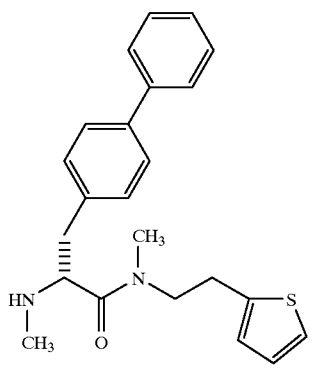

At 0° C., trifluoroacetic acid (4 ml) was added to a solution of N-((1R)-2-(biphenyl-4-yl)-1-(N-methyl-N-(2-(2-thienyl) ethyl)carbamoyl)ethyl)-N-methylcarbamic acid tert-butyl ester (910 mg, 1.90 mmol) in dichloromethane (4 ml). The reaction mixture was stirred for 3 h at 0° C. A saturated solution of sodium hydrogen carbonate (8 ml) was added. Solid sodium hydrogen carbonate was added, until pH 7 was obtained. Water was added, until a clear solution was obtained. The phases were separated. The aqueous phase was extracted with dichloromethane (2×30 ml). The combined organic layers were dried over magnesium sulfate. The solvent was removed in vacuo. The crude produduct was purified by flash chromatogrphy on silica (60 g), using dichloromethane/methanol/25% aqueous ammonia (100:10:1) as eluent, to give 674 mg of (2R)-3-(biphenyl-4-yl)-N-methyl-2-(methylamino)-N-(2-(2-thienyl)ethyl) propionamide.

$^1$H-NMR (CDCl$_3$, selected values): d 2.20 and 2.30 (both s, together 6 H); 2.59 and 2.90 (both s, together 3 H); 6.69, 6.78, 6.90, 7.12, and 7.20–7.60 (all m, together 12 H).

(3E)-4-(N-((1R)-2-(Biphenyl-4-yl)-1-(N-methyl-N-(2-(2-thienyl)ethyl)carbamoyl)ethyl)-N-methylcarbamoyl)-1,1-dimethylbut-3-enylcarbamic acid tert-butyl ester

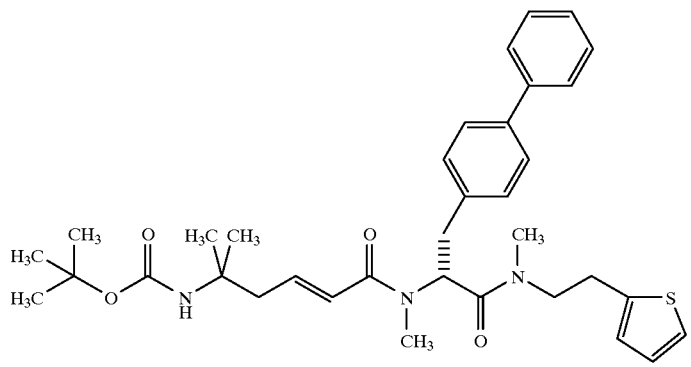

A solution of (2E)-5-(tert-butoxycarbonylamino)-5-methylhex-2-enoic acid (202 mg, 0.83 mmol) and 1-hydroxy-7-azabenzotriazole (113 mg, 0.83 mmol) in N,N-dimethyformamide (3 ml) and dichloromethane (3 ml) was cooled to 0° C. N-(3-Dimethylaminopropyl)-N'-ethylcarbodiimide hydrochloride (159 mg, 0.83 mmol) was added. The reaction mixture was stirred for 10 min at 0° C. A solution of (2R)-3-(biphenyl-4-yl)-N-methyl-2-(methylamino)-N-(2-(2-thienyl)ethyl)propionamide (314 mg, 0.83 mmol) in dichloromethane (3 ml) and ethyldiisopropylamine (0.14 ml, 0.83 mmol) were added successively. The reaction mixture was stirred for 16 h, while it was warming up to room temperature. It was diluted with ethyl acetate (100 ml) and washed with a 10% aqueous solution of sodium hydrogen sulfate (100 ml). The aqueous solution was extracted with ethyl acetate (2×50 ml). The combined organic layers were washed with a saturated solution of sodium hydrogen carbonate (100 ml) and dried over magnesium sulfate. The solvent was removed in vacuo. The crude product was purified on silica (80 g), using ethyl acetate/heptane (1:1 (500 ml), then 2:1) as eluent, to give 374 mg of (3E)-4-(N-((1R)-2-(biphenyl-4-yl)-1-(N-methyl-N-(2-(2-thienyl)ethyl)carbamoyl)ethyl)-N-methylcarbamoyl)-1,1-dimethylbut-3-enylcarbamic acid tert-butyl ester.

$^1$H-NMR (CDCl$_3$, selected values): d 1.25 and 1.26 (both s, together 6 H); 1.39 and 1.40 (both s, together 9 H); 2.85, 2.89, 3.01, and 3.02 (all s, together 6 H); 5.78 (m, 1 H); 6.20 and 6.26 (both d, together 1 H); 6.67–6.90, 7.10, and 7.20–7.60 (all m, together 14 H).

At 0° C., trifluoroacetic acid (3 ml) was added to a solution of (3E)-4-(N-((1R)-2-(biphenyl-4-yl)-1-(N-methyl-N-(2-(2-thienyl)ethyl)carbamoyl)ethyl)-N-methylcarbamoyl)-1,1-dimethylbut-3-enylcarbamic acid tert-butyl ester in dichloromethane (3 ml). The reaction mixture was stirred for 30 min at 0° C. Dichloromethane (30 ml) was added. A saturated aqueous solution of sodium hydrogen carbonate (10 ml) was added. Solid sodium hydrogen carbonate was added until pH 7. Water (30 ml) was added. The phases were separated. The aqueous phase was extracted with dichloromethane (3×15 ml). The combined organic layers were dried over magnesium sulfate. The solvent was removed in vacuo. The crude product was purified by flash chromatography on silica (50 g), using dichloromethane/methanol/25% aqueous ammonia as eluent, to give 152 mg of the title compound.

$^1$H-NMR (CDCl$_3$, selected values): d 1.09 and 1.22 (both s, together 6 H); 2.21 and 2.27 (both d, together 2 H); 2.85, 2.90, 3.07, and 3.08 (all s, together 6 H); 5.78 (m, 1 H); 6.20 and 6.26 (both d, together 1 H); 6.65–6.95, 7.09, and 7.20–7.60 (all m, together 13 H).

MS: 504.0 ([M+H]$^+$).
HPLC
37.87 min (A1).
38.52 min (B1).

For biological testing, the title compound was transferred into its acetate salt, by lyophilization with 0.5M acetic acid (40 ml).

Example 13

(2E)-N-((1R)-1-(N-(2-(2-(2-Hydroxyethoxy)phenyl) ethyl)-N-methylcarbamoyl)-2-(2-naphthyl)ethyl)-N-methyl-5-methyl-5-(methylamino)hex-2-enamide

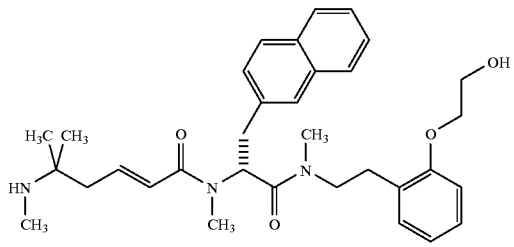

N-((3E)-4-(N-((1R)-1-(N-(2-(2-(2-Hydroxyethoxy)phenyl) ethyl)-N-methylcarbamoyl)-2-(2-naphthyl)ethyl)-N-methylcarbamoyl)-1,1-dimethylbut-3-enyl)-N-methylcarbamic acid tert-butyl ester

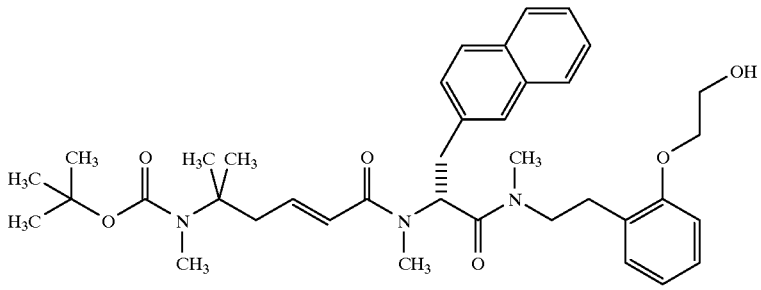

(2E)-5-(N-(tert-Butoxycarbonyl)-N-methylamino)-5-methylhex-2-enoic acid (133 mg, 0.52 mmol) was dissolved in N,N-dimethylformamide (2 ml) and dichloromethane (2 ml). 1-Hydroxy-7-azabenzotriazole (71 mg, 0.52 mmol) was added. The solution was cooled to 0° C. N-(3-Dimethylaminopropyl)-N'-ethylcarbodiimide hydrochloride (100 mg, 0.52 mmol) was added. The solution was stirred for 10 min at 0° C. A solution of (2R)-N-(2-(2-(2-hydroxyethoxy)phenyl)ethyl)-N-methyl-2-(methylamino)-3-(2-naphthyl)propionamide (262 mg, 0.52 mmol) in dichloromethane (2 ml) and ethyldiisopropylamine (0.09 ml, 0.52 mmol) were added successively. The reaction mixture was stirred for 16 h, while it was warming up to room temperature. It was diluted with ethyl acetate (30 ml) and washed with 10% sodium hydrogen sulfate solution (20 ml). The aqueous phase was extracted with ethyl acetate (2×20 ml). The combined organic layers were washed with saturated sodium hydrogen carbonate solution (30 ml) and dried over magnesium sulfate. The solvent was removed in vacuo. The crude product was purified by flash chromatography on silica (100 g), using ethyl acetate/heptane (2:1) as eluent, to give 261 mg of N-((3E)-4-(N-((1R)-1-(N-(2-(2-(2-hydroxyethoxy)phenyl)ethyl)-N-methylcarbamoyl)-2-(2-naphthyl)ethyl)-N-methylcarbamoyl)-1,1-dimethylbut-3-enyl)-N-methylcarbamic acid tert-butyl ester.

$^1$H-NMR (CDCl$_3$, selected values): d 1.25, 1.26, 1.32, 1.33, 1.36, and 1.43 (all s, together 15 H); 2.61, 2.75, 2.90, 2.91, 3.02, and 3.04 (all s, together 9 H); 4.85 and 5.02 (both t, together 1 H); 5.69 and 5.88 (both dd, together 1 H); 6.02 and 6.22 (both d, together 1 H); 6.60–7.85(m, 12).

At 0° C., trifluoroacetic acid (2 ml) was added to a solution of N-((3E)-4-(N-((1R)-1-(N-(2-(2-(2-hydroxyethoxy)phenyl)ethyl)-N-methylcarbamoyl)-2-(2-naphthyl)ethyl)-N-methylcarbamoyl)-1,1-dimethylbut-3-enyl)-N-methylcarbamic acid tert-butyl ester (236 mg, 0.37 mmol) in dichloromethane (2 ml). The reaction mixture was stirred for 40 min at 0° C. A saturated solution of sodium hydrogen carbonate (5 ml) was added. Solid sodium hydrogen carbonate was added, until pH 7 was obtained. Water (30 ml) and dichloromethane (30 ml) were added. The phases were separated. The aqueous phase was extracted with dichloromethane (3×20 ml). The combined organic layers were dried over magnesium sulfate. The solvent was removed in vacuo. The crude product was purified by flash chromatography on silica (60 g), using dichloromethane/methanol/25% aqueous ammonia (100:10:1) as eleuent to give 118 mg of the title comound.

$^1$H-NMR (CDCl$_3$, selected values): d 1.02 and 1.10 (both s, together 6 H); 2.27 and 2.32 (both s, together 3 H); 2.91, 2.98, 3.02, and 3.06 (all s, together 6 H); 5.65 and 5.86 (both dd, together 1 H); 6.10 and 6.25 (both d, together 1 H); 6.55–7.90 (m, 12 H).

MS: 546.0 ([M+H]$^+$).

HPLC
33.47 min (A1).
34.25 min (B1).

For biological testing, the title compound was transferred into its acetate salt, by lyophilization with 0.5M acetic acid (40 ml).

Example 14

3-Aminomethyl-N-[(1R)-1-(N-{2-[2-(2-hydroxyethoxy)phenyl]ethyl}-N-methylcarbamoyl)-2-(2-naphthyl)ethyl]benzamide

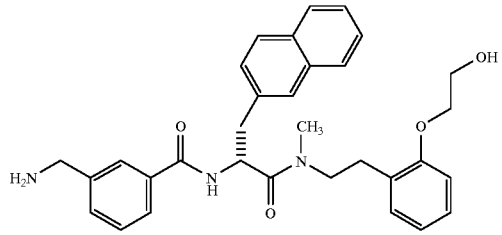

[(1R)-1-(N-{2-[2-(2-Hydroxyethoxy)phenyl]ethyl}-N-methylcarbamoyl)-2-(2-naphthyl)ethyl]carbamic acid tert-butyl ester

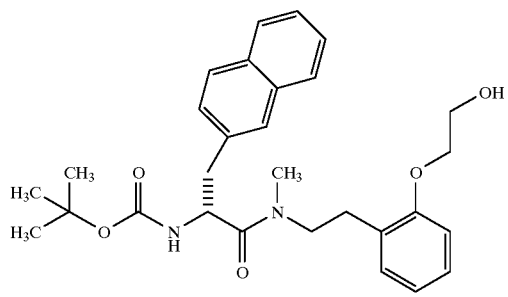

(2R)-2-(tert-Butoxycarbonylamino)-3-(2-naphthyl)propionic acid (654 mg, 2.07 mmol) was dissolved in N,N-dimethylformamide (4 ml) and dichloromethane (4 ml). 1-Hydroxy-7-azabenzotriazole (282 mg, 2.07 mmol) was added. The solution was cooled to 0° C. N-( 3-Dimethylaminopropyl)-N'-ethylcarbodiimide hydrochloride (397 mg, 2.07 mmol) was added. The reaction mixture was stirred for 15 min at 0° C. A solution of 2-(2-(2-(methylamino)ethyl)phenoxy)ethanol (434 mg, 2.07 mmol) in dichloromethane (4 ml) and ethyldiisopropylamine (0.36 ml, 2.07 mmol) were added successively. The reaction mixture was stirred for 16 h, while it was warming up to room temperature. It was diluted with ethyl acetate (50 ml)

and washed with a 10% aqueous solution of sodium hydrogen sulfate (50 ml). The aqueous phase was extracted with ethyl acetate (2×20 ml). The combined organic layers were washed with a saturated aqueous solution of sodium hydrogen carbonate (50 ml) and dried over magnesium sulfate. The solvent was removed in vacuo. The crude product was purified by flash chromatography on silica (70 g), using ethyl acetate/heptane 1:1 as eluent, to give 539 mg of [(1R)-1-(N-{2-[2-(2-hydroxyethoxy)phenyl]ethyl}-N-methylcarbamoyl)-2-(2-naphthyl)ethyl]carbamic acid tert-butyl ester.

$^1$H-NMR (CDCl$_3$): d 1.39 and 1.41 (both s, together 9 H); 2.60 and 2.94 (both s, together 3 H); 5.45 and 5.50 (both s, together 1 H).

(2R)-2-Amino-N-{2-[2-(2-hydroxyethoxy)phenyl]ethyl}-N-methyl-3-(2-naphthyl)propionamide

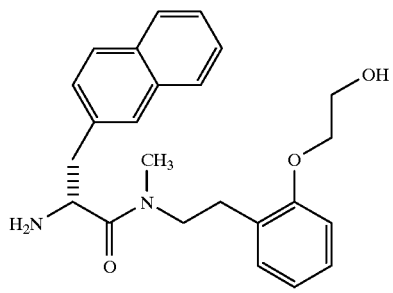

A solution of [(1R)-1-(N-{2-[2-(2-hydroxyethoxy)phenyl]ethyl}-N-methylcarbamoyl)-2-(2-naphthyl)ethyl]carbamic acid tert-butyl ester (519 mg, 1.85 mmol) in dichloromethane (3 ml) was cooled to 0° C. Trifluoroacetic acid (3 mL) was added. The reaction mixture was stirred at 0° C. for 40 min. Dichloromethane (20 ml) was added. A saturated solution of sodium hydrogen carbonate (10 ml) was added dropwise. Solid sodium hydrogen carbonate was added, until pH 7 was obtained. The phases were separated. The aqueous phase was extracted with dichloromethane (3×20 ml). The combined organic layers were dried over magnesium sulfate. The solvent was removed in vacuo. The crude product was purified by flash chromatography on silica (60 g), using dichloromethane/methanol/25% aqueous ammonia, to give 377 mg of (2R)-2-amino-N-{2-[2-(2-hydroxyethoxy)phenyl]ethyl}-N-methyl-3-(2-naphthyl)propionamide.

$^1$H-NMR (CDCl$_3$): d 2.73 and 2.85 (both s, together 3 H); 3.50 (t, 1 H); 7.60 and 7.65 (both s, together 1 H).

((3-((1R)-1-(N-(2-(2-(2-Hydroxyethoxy)phenyl)ethyl)-N-methylcarbamoyl)-2-(2-naphthyl)ethylcarbamoyl)phenyl)methyl)carbamic acid tert-butyl ester 3-(tert-Butoxycarbonylaminomethyl)benzoic acid (113 mg, 0.45 mmol) and 7-aza-1-hydroxybenzotriazole (61 mg, 0.45 mmol) were dissolved in N,N-dimethylformamide (1 ml) and dichloromethane (1 ml). The solution was cooled to 0° C. N-(3-Dimethylaminopropyl)-N'-ethylcarbodiimide hydrochloride (86 mg, 0.45 mmol) was added. The reaction mixture was stirred for 15 min at 0° C. A solution of (2R)-2-amino-N-{2-[2-(2-hydroxyethoxy)phenyl]ethyl}N-methyl-3-(2-naphthyl)propionamide (175 mg, 0.45 mmol) and ethyldiisopropylamine (0.08 ml, 0.45 mmol) were added successively. The reaction mixture was stirred for 16 h, while it was warming up to room temperature. It was diluted with ethyl acetate (50 ml) and washed with a 10% aqueous solution of sodium hydrogen sulfate (50 ml). The aqueous phase was extracted with ethyl acetate (2×15 ml). The combined organic layers were washed with a saturated aqueous solution of sodium hydrogen carbonate (50 ml) and dried over magnesium sulfate. The solvent was removed in vacuo. The crude product was purified by flash chromatography on silica (40 g), using ethyl acetate/heptane 3:1 as eluent, to give 211 mg of ((3-((1R)-1-(N-(2-(2-(2-hydroxyethoxy)phenyl)ethyl)-N-methylcarbamoyl)-2-(2-naphthyl)ethylcarbamoyl)phenyl)methyl)carbamic acid tert-butyl ester.

$^1$H-NMR (CDCl$_3$): d 1.45 (s, 9 H); 2.68 and 2.95 (both s, together 3 H); 4.88 and 4.95 (both br, together 1 H); 5.46 (m, 1 H).

A solution of ((3-((1R)-1-(N-(2-(2-(2-hydroxyethoxy)phenyl)ethyl)-N-methylcarbamoyl)-2-(2-naphthyl)ethylcarbamoyl)phenyl)methyl)carbamic acid tert-butyl ester (193 mg, 0.31 mmol) in dichloromethane (2 ml) was cooled to 0° C. Trifluoroacetic acid (2 ml) was added. The reaction mixture was stirred for 20 min at 0° C. It was diluted with dichloromethane (10 ml). A saturated aqueous solution of sodium hydrogen carbonate (10 ml) was added. Solid sodium hydrogen carbonate was added until pH 7 was obtained. The phases were separated. The aqueous phase was extracted with dichloromethane (3×10 ml). The combined organic layers were dried over magnesium sulfate. The solvent was removed in vacuo. The crude product was purified by flash chromatography on silica (15 g), using dichloromethane/methanol/25% aqueous ammonia as eluent, to give 130 mg of the title compound.

$^1$H-NMR (CDCl$_3$): d 2.75 and 3.04 (both s, together 3 H); 3.86 and 3.90 (both s, together 2 H); 5.51 (m, 1 H).

HPLC:

32.63 min (A1);

39.5 min (B1).

MS: 525.8 ([M+H]$^+$).

For biological testing, the title compound was transferred into its acetate salt by lyophilization with 0.5M acetic acid (40 ml).

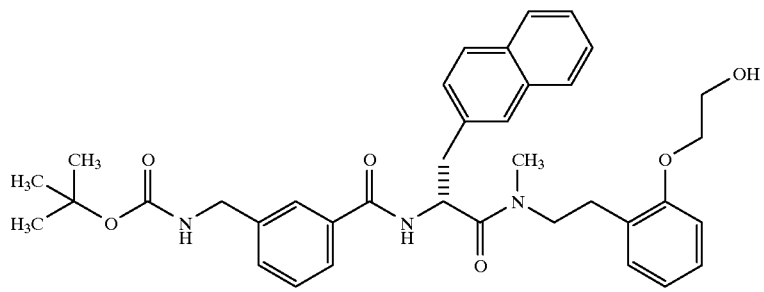

Example 15

(2E)-5-Amino-5-methylhex-2-enoic acid N-((1R)-1-(N-(2-(2-(2-hydroxyethoxy)phenyl)ethyl)-N-methylcarbomoyl)-2-(2-naphthyl)ethyl)amide

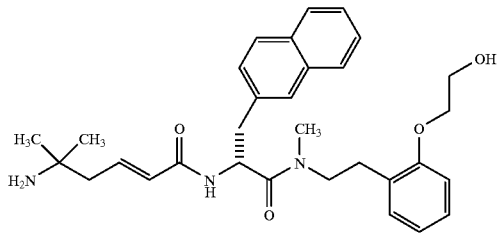

{(3E)-4-[(1R)-(N-{[2-Hydroxyethoxy)phenyl)]ethyl}-N-methylcarbamoyl)-2-(2-naphthyl)ethylcarbamoyl]-1,1-dimethylbut-3-enyl}carbamic acid tert-butyl ester

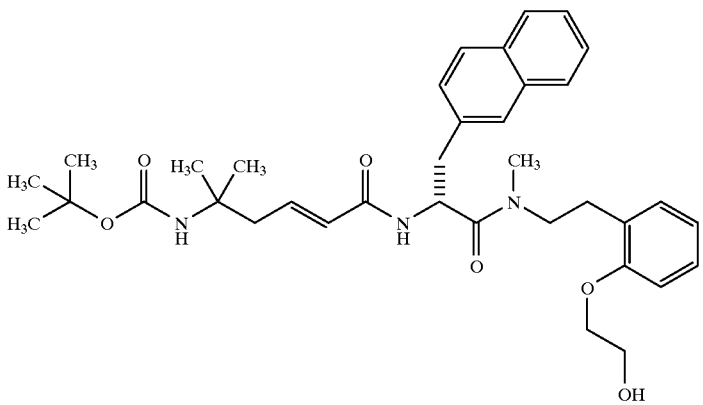

(2E)-5-(tert-Butoxycarbonylamino)-5-methylhex-2-enoic acid (95 mg, 0.39 mmol) was dissolved in dichloromethane (1 ml) and N,N-dimethylformamide (1 ml). 1-Hydroxy-7-azabenzotriazole (55 mg, 0,39 mmol) was added. The solution was cooled to 0° C. N-(3-Dimethylaminopropyl)-N'-ethylcarbodiimide hydrochloride (75 mg 0.39 mmol) was added. The reaction mixture was stirred for 20 min at 0° C. A solution of (2R)-2-amino-N-{2-[2-(2-hydroxyethoxy)phenyl]ethyl}-N-methyl-3-(naphthyl)propionamide (155 mg, 0.39 mmol) in dichloromethane (1 ml) and ethyldiisopropylamine (0.07 ml, 0.39 mmol) were added successively. The reaction mixture was stirred for 16 h, while it was warming up to room temperature. It was diluted with ethyl acetate (30 ml) and washed with 10% aqueous sodium hydrogen sulfate solution (30 ml). The aqueous phase was extracted with ethyl acetate (2×20 ml). The combined organic layers were washed with a saturated aqueous solution of sodium hydrogen carbonate solution (30 ml) and dried over magnesium sulfate. The solvent was removed in vacuo. The crued product was purified by flash chromatography on silica (12 g), using ethyl acetate/heptane (2:1) as eluent to give 147 mg of {(3E)-4-[(1R)-1-(N-{2-[2-(2-hydroxyethoxy)phenyl]ethyl}-N-methylcarbamoyl)-2-(2-naphthyl)ethylcarbamoyl]-1,1-dimethylbut-3-enyl}carbamic acid tert-butyl ester.

$^1$H-NMR (CDCl$_3$): d 1.42 (s, 9 H); 2.58 and 2.92 (both s, together 3 H); 5.31 and 5.37 (both q, together 1 H); 5.80 and 5.87 (both d, together 1 H).

{(3E)-4-[(1R)-1-(N-{2-[2-(2-Hydroxyethoxy)phenyl]ethyl}-N-4methylcarbamoyl)-naphthyl)ethylcarbamoyl]-1,1-dimethylbut-3-enyl}carbamic acid tert-butyl ester (129 mg, 0.21 mmol) was dissolved in dichloromethane (2 ml). The solution was cooled to 0° C. Trifluoroacetic acid (2 ml) was added. The solution was stirred for 15 min at 0° C. It was diluted with dichloromethane (10 ml). A saturated aqueous solution of sodium hydrogen carbonate (10 ml) was added. Solid sodium hydrogen carbonate was added, until pH 7 was obtained. The phases were separated. The aqueous phase was extracted with dichloromethane (3×10 ml). The combined organic layers were dried over magnesium sulfate. The solvent was removed in vacuo. The crude product was purified by flash chromatography on silica (25 g), using dichloromethane/methanol/25% aqueous ammonia as eluent, to give 71 mg of the title compound.

$^1$H-NMR (CDCl$_3$): d 1.13 and 1.14 (both s, together 6 H); 2.24 ("t", 2 H); 2.62 and 2.92 (both s, together 3 H); 5.32 and 5.39 (both q, together 1 H); 5.86 and 5.91 (both d, totether 1 H).

HPLC 31.92 min (A1).

36.57 min (B1).

MS: 518.0 ([M+H]$^+$).

For biological testing, the title compound was transferred into its acetate salt, by lyophilization with 0.5M acetic acid (40 ml).

Example 16

(2E)-5-Amino-5-methylhex-2-enoic acid N-((1R)-1-{N-[2-(2-(benzenesulfonylamino)phenyl)ethyl]-N-methylcarbamoyl}-2-(2-naphthyl)ethyl)-N-methylamide

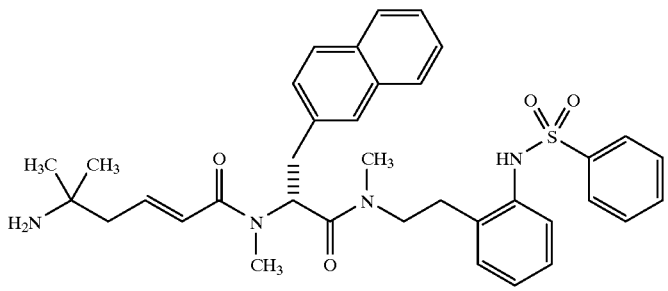

N-[2-(2-(Phenylsulfonylamino)phenyl)ethyl]-N-methylcarbamic acid tert-butyl ester

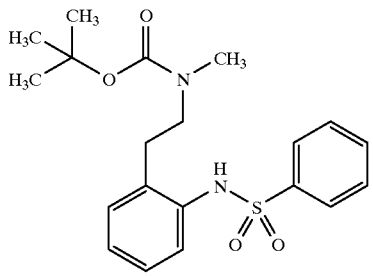

N-(2-(2-Aminophenyl)ethyl)-N-methylcarbamic acid tert-butyl ester (555 mg, 2.22 mmol) and triethylamine (0.40 ml, 2.66 mmol) were dissolved in dichloromethane (12 ml) and cooled to −78° C. A solution of benzenesulfonyl chloride (0.28 ml, 2.22 mmol) in dichloromethane (3 ml) was added dropwise. The solution was stirred for 16 h, while it was warming up to room temperature. It was diluted with ethyl acetate (40 ml) and washed with 10% aqueous sodium hydrogen sulfate solution (20 ml). The aqueous phase was extracted with ethyl acetate (2×15 ml). The combined organic layers were washed with saturated aqueous sodium hydrogen carbonate solution (30 ml) and dried over magnesium sulfate. The solvent was removed in vacuo. The crude product was purified by flash chromatography on silica (30 g), using ethyl acetate/heptane 1:3 as eluent, to give 557 mg of N-[2-(2-(phenylsulfonylamino)phenyl)ethyl]-N-methylcarbamic acid tert-butyl ester.

$^1$H-NMR (CDCl$_3$, selected values): d 1.55 (br, 9 H); 2.82 (br, 3 H); 8.80 (br., 1 H).

N-[2-(2-(Methylamino)ethyl)phenyl]benzenesulfonamide

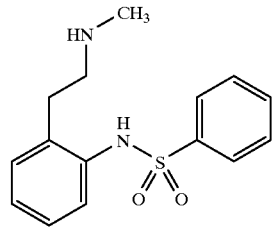

N-[2-(2-(Phenylsulfonylamino)phenyl)ethyl]-N-methylcarbamic acid tert-butyl ester (547 mg, 1.4 mmol) was dissolved in dichloromethane (5 ml). 3.1N hydrogen chloride in ethyl acetate (3 ml, 9.3 mmol) was added. The solution was stirred at room temperature for 1 h. Another portion of 3.1N hydrogen chloride in ethyl acetate (5 ml, 15.3 mmol) was added. The solution was stirred for another 3.5 h. The solvent was removed in vacuo. The crude product was purified by flash chromatography on silcia (7 g), using dichloromethane/methanol/25% aqueous ammonia 50:10:1 as eluent, to give 521 mg of N-[2-(2-(methylamino)ethyl)phenyl]benzenesulfonamide.

$^1$H-NMR (CDCl$_3$, selected values): d 2.42 (m, 2 H), 2.50 (s, 3 H); 2.82 (m, 2 H).

N-((1R)-1-{N-[2-(2-(Phenylsulfonylamino)phenyl)ethyl]-N-methylcarbamoyl}-2-(2-naphthyl)ethyl)-N-methylcarbamic acid tert-butyl ester

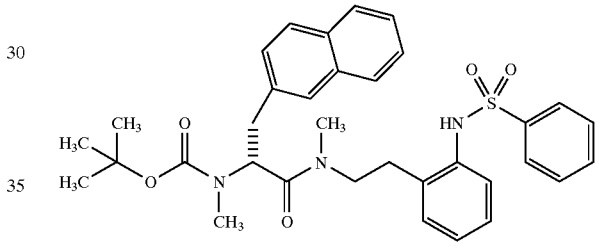

(2R)-2-(N-(tert-Butoxycarbonyl)-N-methylamino)-3-(2-naphthyl)propionic acid (517 mg, 1.57 mmol) and 1-hydroxy-7-azabenzotriazole (214 mg, 1.57 mmol) were dissolved in dichloromethane (6 ml) and N,N-dimethylformamide (6 ml). The mixture was cooled to 0° C. N-(3-Dimethylaminopropyl)-N'-ethylcarbodiimide hydrochloride (301 mg, 1.57 mmol) was added. The reaction mixture was stirred for 15 min at 0° C. A solution of N-[2-(2-(methylamino)ethyl)phenyl]benzenesulfonamide (457 mg, 1.57 mmol) in dichloromethane (6 ml) and ethyldiisopropylamine (0.27 ml, 1.57 mmol) were added successively. The reaction mixture was stirred for 16 h, while it was warming up to room temperature. It was diluted with ethyl acetate (100 ml) and washed with a 10% aqueous sodium hydrogen sulfate solution (100 ml). The aqueous phase was extracted with ethyl acetate (2×30 ml). The combined organic layers were washed with a saturated aqueous solution of sodium hydrogen carbonate and dried over magnesium sulfate. The solvent was removed in vacuo. The crude product was purified by flash chromatography on silica (25 g), using ethyl acetate/heptane 1:1 as eluent, to give 785 mg of N-((1R)-1-{N-[2-(2-(phenylsulfonylamino)phenyl)ethyl]-N-methylcarbamoyl}-2-(2-naphthyl)ethyl)-N-methylcarbamic acid tert-butyl ester.

$^1$H-NMR (CDCl$_3$, selected values): d 4.80, 5.05, and 5.43 (dd, t, and t, together 1 H).

(2R)-N-[2-(2-(Phenylsulfonylamino)phenyl)ethyl]-N-methyl-2-(methylamino)-3-(2-naphthyl)propionamide

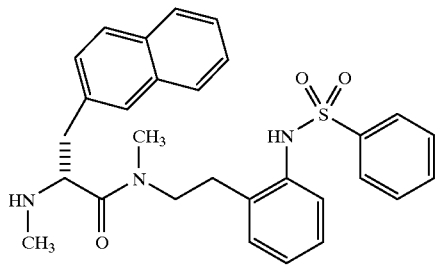

At 0° C., trifluoroacetic acid (4 ml) was given to a solution of N-((1R)-1-{N-[2-(2-(phenylsulfonylamino)phenyl) ethyl]-N-methylcarbamoyl}-2-(2-naphthyl)ethyl)-N-methylcarbamic acid tert-butyl ester (647 mg, 1.08 mmol) in dichloromethane (4 ml). The reaction mixture was stirred for 2.5 h at 0° C. It was diluted with dichloromethane (15 ml). A saturated aqueous solution of sodium hydrogen carbonate (15 ml) was added. Solid sodium hydrogen carbonate was added until pH 7 was obtained. The phases were separated. The aqueous phase was extracted with dichloromethane (2×15 ml). The combined organic layers were dried over magnesium sulfate. The solvent was removed in vacuo. The crude product was purified by flash chromatography on silica (20 g), using dichloromethane/methanol/25% aqueous ammonia 200:10:1 as eluent to give 434 mg of (2R)-N-[2-(2-(phenylsulfonylamino)phenyl)ethyl]-N-methyl-2-(methylamino)-3-(2-naphthyl)propionamide.

¹H-NMR (CDCl₃, selected values): d 2.37, 2.43, 2.52, and 2.75 (all s, together 6 H); 3.72 and 3.89 (dd and t, together 1 H).

{(3E)-4-[N-((1R)-1-{N-[2-(2-(Phenylsulfonylamino) phenyl)ethyl]-N-methylcarbamoyl}-2-2-naphthyl)ethyl)-N-methylcarbamoyl]-1,1-dimethylbut-3-enyl}carbamic acid tert-butyl ester ethyl acetate (2×30 ml). The combined organic layers were washed with a saturated aqueous solution of sodium hydrogen carbonate (60 ml) and dried over magnesium sulfate. The solvent was removed in vacuo. The crude product was purified by flash chromatography on silica (50 g), using ethyl acetate/heptane 1:1 as eluent, to give 363 mg of {(3E)-4-[N-((1R)-1-{N-[2-(2-(phenylsulfonylamino) phenyl)ethyl]-N-methylcarbamoyl}-2-(2-naphthyl)ethyl)-N-methylcarbamoyl]-1,1-dimethylbut-3-enyl}carbamic acid tert-butyl ester.

¹H-NMR (CDCl₃, selected values): d 1.25 and 1.40 (both m, together 15 H); 2.85 and 2.86 (both s, together 3 H); 3.12 and 3.18 (both s, together 3 H); 5.62 and 5.87 (t and dd, together 1 H); 6.20 and 6.31 (both d, together 1 H).

A solution of {(3E)-4-[N-((1R)-1-{N-[2-(2-(phenylsulfonylamino)phenyl)ethyl]-N-methylcarbamoyl}-2-(2-naphthyl)ethyl)-N-methylcarbamoyl]-1,1-dimethylbut-3-enyl}carbamic acid tert-butyl ester (330 mg, 0.45 mmol) in dichloromethane (3 ml) was cooled to 0° C. Trifluoroacetic acid (3 ml) was added. The reaction mixture was stirred for 40 min at 0° C. It was diluted with dichloromethane (20 ml). A saturated aqueous solution of sodium hydrogen carbonate (6 ml) was added. Solid sodium hydrogen carbonate was added until pH 7 was obtained. The phases were separated. The aqueous phase was extracted with dichloromethane (3×20 ml). The combined organic layers were dried over magnesium sulfate. The solvent was removed in vacuo. The crude product was purified by flash chromatography on silica (20 g), using dichloromethane/methanol/25% aqueous ammonia 100:10:1 as eluent, to give 252 mg of the title compound.

¹H-NMR (CDCl₃, selected values): d 1.09 and 1.12 (both s, together 6 H); 2.84 and 2.86 (both s, together 3 H); 3.15 and 3.20 (both s, together 3 H); 5.65 and 5.87 (t and dd, together 1 H); 6.22 and 6.32 (both d, together 1 H).

HPLC 37.87 min (A1).

40.23 min (B1).

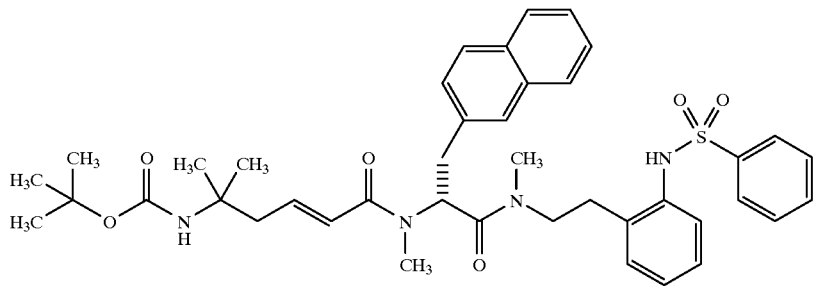

At 0° C., N-(3-Dimethylaminopropyl)-N'-ethylcarbodiimide hydrochloride (138 mg, 0.72 mmol) was added to a solution of (2E)-5-(tert.-butoxycarbonylamino)-5-methylhex-2-enoic acid (175 mg, 0.72 mmol) and 1-hydroxy-7-azabenzotriazole (98 mg, 0.72 mmol) in dichloromethane (3 ml) and N,N-dimethylformamide (3 ml). The reaction mixture was stirred for 20 min at 0° C. A solution of (2R)-N-[2-(2-(phenylsulfonylamino)phenyl)ethyl]-N-methyl-2-(methylamino)-3-(2-naphthyl)propionamide (363 mg, 0.72 mmol) in dichloromethane (3ml) and ethyldiisopropylamine (0.13 ml) were added successively. The reaction mixture was stirred for 3 d, while it was warming up to room temperature. It was diluted with ethyl acetate (60 ml) and washed with a 10% aqueous solution of sodium hydrogen sulfate (60 ml). The aqueous phase was extracted with

MS: 627.2 ([M+H]⁺).

For biological testing, the title compound was transferred into its acetate salt, by lyophilization with 0.5M acetic acid (40 ml).

Example 17

2-Amino-N-(2-(2-(N-((2R)-2-(N-((2E)-5-Amino-5-methylhex-2-enoyl)-N-methylamino)-3-(2-naphthyl) propionyl)-N-methylamino)ethyl)phenyl)acetamide

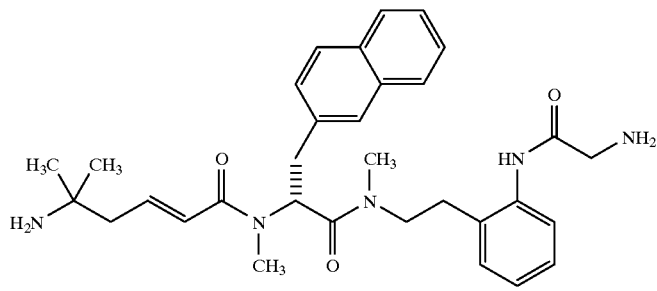

({2-[2-(N-(tert-Butoxycarbonyl)-N-methylamino)ethyl] phenylcarbamoyl}methyl)carbamic acid ((9-fluorenyl) methyl) ester

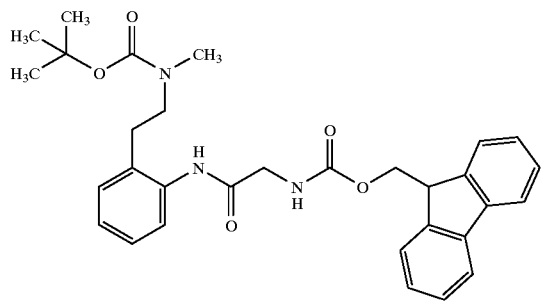

2-(((9-Fluorenyl)methoxycarbonyl)amino)acetic acid (2.49 g, 2.79 mmol) was suspended in dichloromethane (40 ml). The suspension was cooled to 0° C. N-(3-Dimethylaminopropyl)-N'-ethylcarbodiimide hydrochloride (802 mg, 4.19 mmol) was added. The reaction mixture was stirred for 30 min at 0° C. A solution of N-(2-(2-aminophenyl)ethyl)-N-methylcarbamic acid tert-butyl ester (698 mg, 2.79 mmol) in dichloromethane (15 ml) was added. The reaction mixture was stirred for 16 h, while it was warming up to room temperature. It was diluted with dichloromethane (100 ml) and washed with brine (100 ml). The aqueous solution was extracted with dichloromethane (2×30 ml). The combined organic layers were dried over magnesium sulfate. The solvent was removed in vacuo. The crude product was purified by flash chromatography on silica (80 g), using ethyl acetate/heptane (1:1) as eluent, to give 1.412 g of ({2-[2-(N-(tert-butoxycarbonyl)-N-methylamino)ethyl] phenylcarbamoyl}methyl)carbamic acid ((9-fluorenyl) methyl) ester.

¹H-NMR (CDCl₃, seleceted values): d 1.50 (br, 9 H); 2.80 (m, 2 H); 2.98 (br, 3 H); 3.22 (m, 2 H); 4.25 (m, 3 H); 4.40 (m, 2 H); 6.32 (br, 1 H); 9.20 (br, 1 H).

{[2-(2-(Methylamino)ethyl)phenylcarbamoyl] methyl}carbamic acid 9H-((fluoren-9-yl)methyl) ester

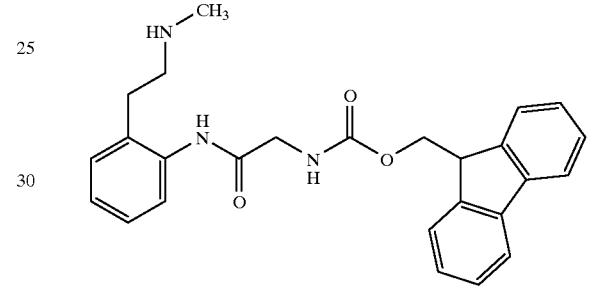

({2-[2-(N-(tert-Butoxycarbonyl)-N-methylamino)ethyl] phenylcarbamoyl}methyl)carbamic acid ((9-fluorenyl) methyl) ester (1.342 g, 2.53 mmol) was dissolved in 3.0M hydrogen chloride in ethyl acetate (10 ml). The reaction mixture was stirred for 2 h at room temperature. Diethyl ether (40 ml) was added. The precipitation was filtered off and dried in vacuo to give 857 mg of crude {[2-(2-(methylamino)ethyl)phenylcarbamoyl]methyl}carbamic acid 9H-((fluoren-9-yl)methyl) ester as hydrochloride, which was used for the next step without purification.

¹H-NMR (DMSO-d₆, seleceted values): d 2.99 (br, 4 H); 9.05 (br, 2 H); 9.68 (br, 1 H).

N-{(1R)-1-[N-(2-{2-[2-((Fluoren-9-ylmethoxycarbonyl) amino)acetylamino]phenyl}ethyl)-N-methylcarbamoyl]-2-(2-naphthyl)ethyl}-N-methylcarbamic acid tert-butyl ester

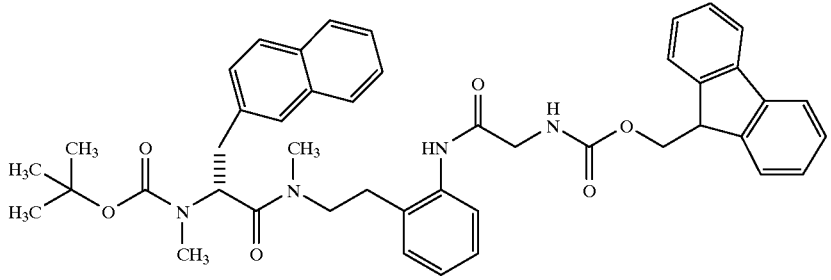

(2R)-2-(N-(tert-Butoxycarbonyl)-N-methylamino)-3-(2-naphthyl)propionic acid (590 mg, 1.79 mmol) and 1-hydroxy-7-azabenzotriazole (243 mg, 1.79 mmol) were dissolved in dichloromethane (12 ml) and N,N-dimethylformamide (6 ml). The solution was cooled to 0° C. N-(3-Dimethylaminopropyl)-N'-ethylcarbodiimide hydrochloride (343 mg, 1.79 mmol) was added. The solution was stirred for 25 min at 0° C. The hydrochloride of {[2-(2-(methylamino)ethyl)phenylcarbamoyl]methyl}carbamic acid 9H-((fluoren-9-yl)methyl) ester (834 mg, 1.79 mmol) and ethyldiisopropylamine (0.62 ml, 3.58 mmol) were added successively. The reaction mixture was stirred for 16 h, while it was warming up to room temperature. It was diluted with ethyl acetate (30 ml) and washed with 10% aqueous sodium hydrogen sulfate solution (30 ml). The aqueous phase was extracted with ethyl acetate (3×30 ml). The combined organic layers were washed with a saturated aqueous solution of sodium hydrogen carbonate (30 ml) and dried over magnesium sulfate. The solvent was removed in vacuo. The crude product was purified by flash chromatography on silica (60 g), using ethyl acetate/heptane (1:1) as eluent, to give 1.293 g of N-{(1R)-1-[N-(2-{2-[2-((fluoren-9-ylmethoxycarbonyl)amino)acetylamino]phenyl}ethyl)-N-methylcarbamoyl]-2-(2-naphthyl)ethyl}-N-methylcarbamic acid tert-butyl ester.

$^1$H-NMR (CDCl$_3$, selected values): d (1.25 and 1.30, both br, togetether 9 H); 2.85, 3.03 and 3.04 (all s, togetether 6 H); 5.08 and 5.45 (both t, together 1 H); 9.31 and 9.45 (both s, together 1 H).

[(2-{2-[N-Methyl-N-((2R)-2-methylamino-3-(2-naphthyl)propionyl)amino]ethyl}phenylcarbamoyl)methyl]carbamic acid (fluoren-9-yl)methyl ester N-{(1R)-1-[N-(2-{2-[2-((Fluoren-9-ylmethoxycarbonyl)amino)acetylamino]phenyl}ethyl)-N-methylcarbamoyl]-2-(2-naphthyl)ethyl}-N-methylcarbamic acid tert-butyl ester (1.18 g, 1.59 mmol) was dissolved in 3.0M hydrogen chloride in ethyl acetate (8 ml). The reaction mixture was stirred for 2.25 h at room temperature. The solvent was removed in vacuo. The residue was washed with diethyl ether (3×20 ml) and dried in vacuo to give 1.198 g of crude [(2-{2-[N-methyl-N-((2R)-2-methylamino-3-(2-naphthyl)propionyl)amino]ethyl}phenylcarbamoyl)methyl]carbamic acid (fluoren-9-yl)methyl ester as hydrochloride, which was used for the next step without purification.

$^1$H-NMR (DMSO-d$_6$, seleceted values): d 4.41 and 4.67 (both m, together 1 H).

(3E)-4-(N-((1R)-1-(N-(2-(2-((((9-Fluorenyl)methoxycarbonyl)amino)acetylamino)phenyl)ethyl)-N-methylcarbmoyl)-2-(2-naphthyl)ethyl)-N-methylcarbamoyl)-1,1-dimethylbut-3-enylcarbamic acid tert-butyl ester

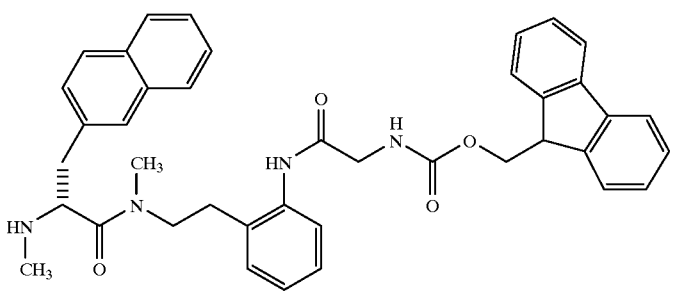

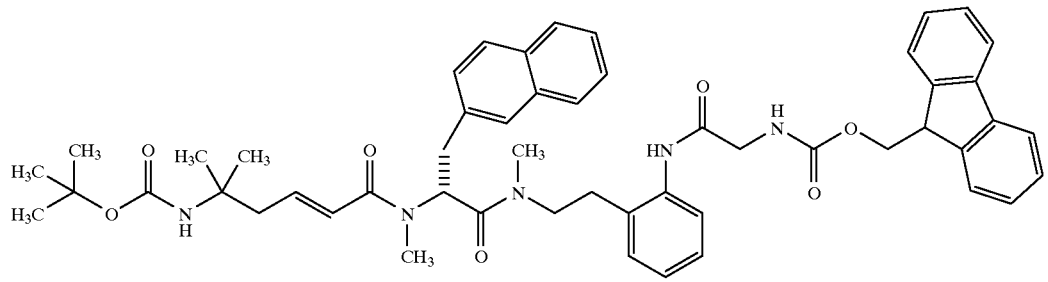

(2E)-5-(tert-Butoxycarbonylamino)-5-methylhex-2-enoic acid (200 mg, 0.82 mmol) and 1-hydroxy-7-azabenzotriazole (112 mg, 0.82 mmol) were dissolved in dichloromethane (4 ml) and N,N-dimethylformamide (2 ml). The solution was cooled to 0° C. N-(3-Dimethylaminopropyl)-N'-ethylcarbodiimide hydrochloride (157 mg, 0.82 mmol) was added. The reaction mixture was stirred for 20 min at 0° C. The hydrochloride of crude [(2-{2-[N-methyl-N-((2R)-2-methylamino-3-(2-naphthyl)propionyl)amino]ethyl}phenylcarbamoyl)methyl]carbamic acid (fluoren-9-yl)methyl ester (553 mg, 0.82 mmol) and ethyldiisopropylamine (0.28 ml, 1.64 mmol) were added successively. The reaction mixture was stirred for 16 h, while it was warming up to room temperature. It was diluted with ethyl acetate (50 ml) and washed with 10% aqueous sodium hydrogen sulfate solution (50 ml). The aqueous phase was extracted with ethyl acetate (2×20 ml). The combined organic layers were washed with a saturated aqueous solution of sodium hdyrogen carbonate (50 ml) and dried over magnesium sulfate. The solvent was removed in vacuo. The crude product was purified by flash chromatography on silca (40 g), using ethyl acetate/heptane (2:1) as eluent, to give 265 mg of (3E)-4-(N-((1R)-1-(N-(2-(2-((((9H-9-fluorenyl)methoxycarbonyl)amino)acetylam ino)phenyl)ethyl)-N-methylcarbmoyl)-2-(2-naphthyl)ethyl)-N-methylcarbamoyl)-1,1-dimethylbut-3-enylcarbamic acid tert-butyl ester.

$^1$H-NMR (CDCl$_3$, selected values): d 5.51 and 5.94 (t and dd, together 1 H); 6.13 and 6.25 (both d, together 1 H); 6.25 (br, 1 H); 6.75 and 6.83 (both m, together 1 H).

(3E)-4-(N-((1R)-1-(N-(2-(2-(2-Aminoacetylamino)phenyl)ethyl)-N-methylcarbamoyl)-2-(2-naphthyl)ethyl)-N-methylcarbamoyl)-1,1-dimethylbut-3-enylcarbamic acid tert-butyl ester 0.40 mmol) in dichloromethane (2.8 ml). The reaction mixture was stirred for 1.2 h at room temperature. It was diluted with dichloromethane (40 ml) and washed with brine (50 ml). The aqueous phase was extracted wtih dichloromethane (3×20 ml). The combined organic layers were washed with buffer of sodium dihyrogen phosphate and dipotassium hydrogen phosphate (pH 6.4, 3×30 ml) and successively with brine (20 ml). They were dried over magnesium sulfate. The solvent was removed in vacuo. The crude product was purified by flash chromatography on silica (40 g), using dichloromethane/methanol/25% aqueous ammonia (100:10:1) as eluent, to give 185 mg of (3E)-4-(N-((1R)-1-(N-(2-(2-(2-methylcarbamoyl)-1,1-dimethylbut-3-enylcarbamic acid tert-butyl ester.

$^1$H-NMR (CDCl$_3$, selected values): d 1.14, 1.15, 1.23, and 1.24 (all s, together 6 H); 1.39 and 1.40 (both s, together 9 H); 2.90, 2.94, 3.02, and 3.10 (all s, together 6 H); 5.64 and 5.90 (t and dd, together 1 H); 6.12 and 6.26 (both d, together 1 H); 6.63 and 6.82 (both m, together 1 H); 9.42 and 9.53 (both br, together 1 H).

(3E)-4-(N-((1R)-1-(N-(2-(2-(2-Aminoacetylamino)phenyl)ethyl)-N-methylcarbamoyl)-2-(2-naphthyl)ethyl)-N-methylcarbamoyl)-1,1-dimethylbut-3-enylcarbamic acid tert-butyl ester (175 mg, 0.27 mmol) was dissolved in dichloromethane (2 ml). The solution was cooled to 0° C. Trifluoroacetic acid (2 ml) was added. The reaction mixture was stirred for 25 min at 0° C. Dichloromethane (20 ml) and ethanol (20 ml) were added successively. The solvent was removed in vacuo without warming. The residue was dissolved in dichlromethane (40 ml) and the solvent was removed in vacuo. The last procedure was repeated. The crude product was purified by flash chromatography on silica (15 g), using dichloromethane/methanol/25% aqueous ammonia /(first: 100:10:1, then: 100:20:2) as eluent, to give 128 mg of the title compound.

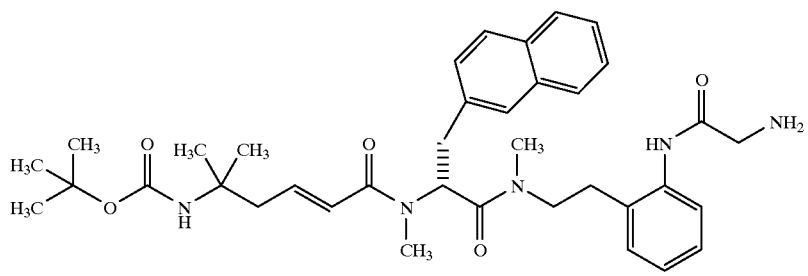

At room temperature tris(2-aminoethyl)amine (2.99 ml, 19.8 mmol) was added to a solution of (3E)-4-(N-((1R)-1-(N-(2-(2-((((9-naphthyl)ethyl)-N-methylcarbamoyl)-1,1-dimethylbut-3-enylcarbamic acid tert-butyl ester (346 mg, $^1$H-NMR (CDCl$_3$, selected values): d 1.03 and 1.12 (both s, together 6 H); 2.92, 2,94, 3.01, and 3.12 (all s, together 6 H); 5.62 and 5.90 (t and dd, together 1 H); 6.10 and 6.25

(both d, together 1 H); 6.70 and 6.89 (both m, together 1 H); 9.48 and 9.52 both br, together 1 H).

HPLC:

7.15 min (H8).

For biological testing, the title compound was transferred into its acetate salt by lyophilization with 0.5M acetic acid (40 ml).

HPLC-method H8:

The RP-analysis was performed using UV detections at 214, 254, 276, and 301 nm on a 218TP54 4.6 mm×150 mm C-18 silica column, which was eluted at 1 mL/min at 42° C. The column was equilibrated with 5% acetonitrile, 85% water and 10% of a solution of 0.5% trifluoroacetic acid in water and eluted by a linear gradient from 5% acetonitrile, 85% water and 10% of a solution of 0.5% trifluoroacetic acid to 90% acetonitrile and 10% of a solution of 0.5% trifluoroacetic acid over 15 min.

Example 18

(2R)-2-(N-((2E)-5-Amino-5-methylhex-2-enoyl)-N-methylamino)-N-(2-(2-(3-hydroxypropoxy)phenyl)ethyl)-N-methyl-3-(2-naphthyl)propionamide

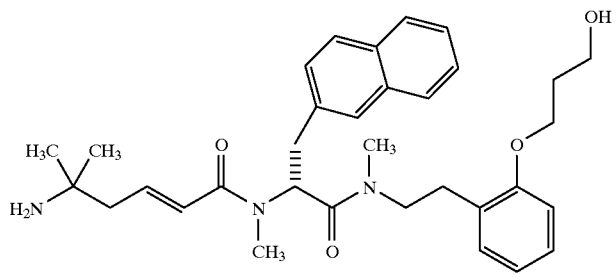

2-(2-Benzyloxyphenyl)-N-methylacetamide

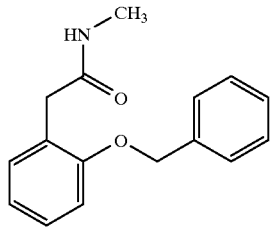

2-(2-Benzyloxyphenyl)acetic acid (15.0 g, 62 mmol) was dissolved in dichloromethane (270 ml) and N,N-dimethylformamide (70 ml). 1-Hydroxybenzotriazole (8.37 g, 62 mmol) was added. The solution was cooled to 0° C. N-(3-Dimethylaminopropyl)-N'-ethylcarbodiimide hydrochloride (11.89 g, 62 mmol) was added. The reaction mixture was stirred for 20 min. A 8.0M solution of methylamine in ethanol (38.8 ml, 310 mmol) was added. The solution was stirred for 16 h, while it was warming up to room temperature. It was diluted with ethyl acetate (500 ml) and washed with a 10% aqueous solution of sodium hydrogen sulfate solution (500 ml). The aqueous phase was extracted with ethyl acetate (2×300 ml). The combined organic layers were washed with a saturated aqueous solution of sodium hydrogen carbonate (400 ml) and dried over magnesium sulfate. The solvent was removed in vacuo. The remaining crystals were washed with a mixture of ethyl acetate/heptane 1:4 (100 ml). They were dried in vacuo. They were dissolved in ethyl acetate. The solution was washed with a saturated aqueous solution of sodium hydrogen carbonate (2×500 ml) and dried over magnesium sulfate. The solvent was removed in vacuo to give 10.24 g of 2-(2-benzyloxyphenyl)-N-methylacetamide.

$^1$H-NMR (DMSO-$d_6$): d 2.57 and 2.58 (both s, together 3 H); 3.44 (s, 2 H); 5.60 and 5.61 (both s, together 2 H); 6.89 (t, 1 H); 7.03 (d, 1 H); 7.19 (m, 2 H); 7.30 (m, 1 H); 7.38 (m, 2 H); 7.45 (m, 2 H); 7.69 (br, 1 H).

N-(2-(2-Benzyloxyphenyl)ethyl)-N-methylamine

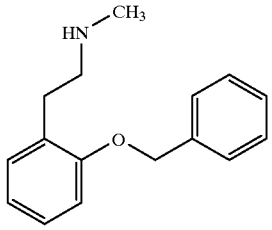

At 0° C., a solution of 2-(2-benzyloxyphenyl)-N-methylacetamide (9.39 g, 36.8 mmol) in tetrahydrouflran (150 ml) was added dropwise to a suspension of sodium borohydride (1.67 g, 44.12 mmol) in tetrahydrofuran (100 ml). After the addition was finished, a solution of iodine (4.67 g, 18.39 mmol) in tetrahydrofuran (200 ml) was added dropwise. The solution was warmed to reflux for 16 h. It was cooled to 0° C. Methanol (200 ml) was added dropwise. The solvent was removed in vacuo. The residue was dissolved in an aqueous 20% sodium hydroxide solution (200 ml) and tert-butyl methyl ether (200 ml). The phases were separated. The aqueous phase was extracted with tert-butyl methyl ether (3×75 ml). The combined organic layers were dried over magnesium sulfate. The solvent was removed in vacuo. The crude product was purified by flash chromatography on silica (400 9), using dichloromethane/methanol/25% aqueous ammonia as eluent (100:10:1), to give 4.38 g of N-(2-(2-benzyloxyphenyl)ethyl)-N-methylamine.

$^1$H-NMR (CDCl$_3$): d 2.40 (s, 3 H); 2.70 (br, 1 H); 2.87 (m, 4 H); 5.07 (s, 2 H); 6.89 (m, 2 H); 7.18 (m, 2 H); 7.35 (m, 5 H).

N-(2-(2-Benzyloxyphenyl)ethyl)-N-methylcarbamic acid tert-butyl ester

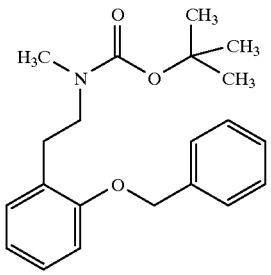

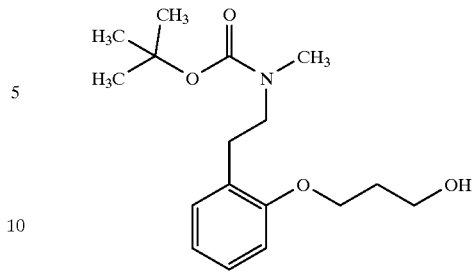

A solution of di-tert-butyl dicarbonate (3.80 g, 17.4 mmol) in tetrahydrofuran (8.7 ml) was added dropwise to a solution of N-(2-(2-benzyloxyphenyl)ethyl)-N-methylamine (3.82 g, 15.8 mmol) in tetrahydrofuran (8.7 ml) and an 1N aqueous sodium hydroxide solution (17.4 ml, 17.4 mmol). The reaction mixture was stirred for 16 h at room temperature. It was diluted with ethyl acetate (200 ml) and water (200 ml). The phases were separated. The aqueous phase was extracted with ethyl acetate (200 ml). The combined organic layers were washed with a saturated aqueous solution of sodium hydrogen carbonate (400 ml) and dried over magensium sulfate. The solvent was removed in vacuo. The crude product was purified by flash chromatography on silica (225 g), using ethyl acetate/heptane 1:4 as eluent, to give 4.73 g of N-(2-(2-benzyloxyphenyl)ethyl)-N-methylcarbamic acid tert-butyl ester.

$^1$H-NMR (CDCl$_3$): d 1.32 and 1.42 (both br, tohgether 9 H); 2.74 and 2.86 (both br, together 5 H); 3.43 (t, 2 H); 5.08 (s, 2 H); 6.89 (m, 2 H); 7.17 (br, 2 H); 7,40 (m, 5 H).

N-(2-(2-Hydroxyphenyl)ethyl)-N-methylcarbamic acid tert-butyl ester

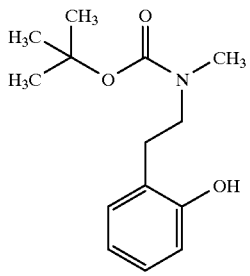

N-(2-(2-Benzyloxyphenyl)ethyl)-N-methylcarbamic acid tert-butyl ester (4.66 g, 13.65 mmol) was dissolved in ethanol (35.6 ml) and was hydrogenated at room pressure in the presence of 10% palladium on activated carbon for 16 h. The reaction mixture was filtered through a plug of celite. The celite was washed with ethyl acetate (50 ml). The liquid phases were collected. The solvents were removed in vacuo. The crude product was purified by flash chromatography on silica (300 g), using ethyl acetate/heptane (1:2) as eluent, to give 2.84 g of N-(2-(2-hydroxyphenyl)ethyl)-N-methylcarbamic acid tert-butyl ester.

$^1$H-NMR (CDCl$_3$): d 1.45 (s, 9 H); 2.86 (t, 2 H); 2.90 (s, 3 H); 3.34 (br, 2 H); 6.81 (t, 1 H); 6.87 (br, 1 H), 7.03 (d, 1 H), 7.12 (t, 1 H).

{2-[2-(3-Hydroxypropoxy)phenyl]ethyl}-N-methylcarbamic acid tert-butyl ester

N-(2-(2-Hydroxyphenyl)ethyl)-N-methylcarbamic acid tert-butyl ester (702 mg, 2.79 mmol) was dissolved in N,N-dimethylformamide (6 ml). Potassium carbonate (1.93 g, 13.97 mmol) and cesium chloride (24 mg, 0.14 mmol) were added. 3-bromo-1-propanol (0.28 ml, 3.07 mmol) was added. The reaction mixture was stirred at 80° C. for 16 h. It was cooled to room temperature and diluted with ethyl acetate (75 ml) and water (75 ml). The phases were separated. The aqueous phase was extracted with ethyl acetate (2×50 ml). The combined organic layers were washed with a 10% aqueous solution of sodium hydrogen sulfate solution (70 ml) and a saturated aqueous solution of sodium hydrogen carbonate (70 ml). They were dried over magnesium sulfate. The solvent was removed in vacuo. The crude product was purified by flash chromatography on silica (80 g), using ethyl acetate/heptane (1.1) as eluent, to give 606 mg of {2-[2-(3-hydroxypropoxy)phenyl]ethyl}-N-methylcarbamic acid tert-butyl ester.

$^1$H-NMR (CDCl$_3$): d 1.39 (br, 9 H); 2.06 (m, 2 H); 2.82 (br, 5 H); 3.45 (br, 2 H); 3.90 (br, 2 H); 4.14 (t, 2 H); 6.85 (m, 2 H); 7.09 (br, 1 H); 7.17 (t, 1 H).

3-[2-(2-Methylaminoethyl)phenoxy]propan-1-ol

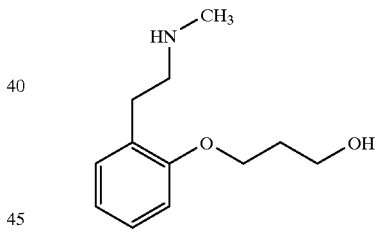

{2-[2-(3-Hydroxypropoxy)phenyl]ethyl}-N-methylcarbamic acid tert-butyl ester (0.587 g, 1.90 mmol) was dissolved in dichloromethane (5 ml). The solution was cooled to 0° C. Trifluoroacetic acid (5 ml) was added. The reaction mixture was stirred for 30 min at 0° C. Dichloromethane (50 ml) was added. A saturated aqueous solution of sodium hydrogen carbonate (50 ml) was added dropwise. Solid sodium hydrogen carbonate was added, until pH 7 was obtained. The phases were separated. The aqueous solution was extracted with dichloromethane (3×70 ml). The aqueous phase was made basic to pH 14 with a 20% aqueous sodium hydroxide solution. It was extracted with tert-butyl methyl ether (3×100 ml). The tert-butyl methyl ether extracts were combined and dried over magnesium sulfate. The solvent was removed in vacuo to give 227 mg of crude 3-[2-(2-methylaminoethyl)phenoxy]propan-1-ol. The crude product was use d in the next step without further purification.

$^1$H-NMR (CDCl$_3$): d 1.19 (s, 1 H); 2.03 (m, 2 H); 2,25 (br, 1 H); 2.39 (s, 3 H); 2.83 (m, 4 H); 3.87 (m, 2 H); 4.10 (m, 2 H); 5.90 (m, 2 Hr; 7.15 (m, 2 H).

103

N-[(1R)-1-(N-{2-[2-(3-Hydroxypropoxy)phenyl]ethyl}-N-methylcarbamoyl)-2-(2-naphthyl)ethyl]-N-methylcarbamic acid tert-butyl ester

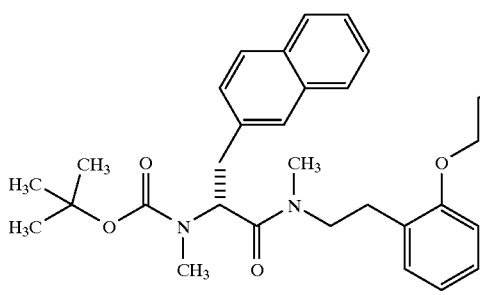

(2R)-2-(N-(tert-Butoxycarbonyl)-N-methylamino)-3-(2-naphthyl)propionic acid (357 mg, 1.08 mmol) and 1-hydroxy-7-azabenzotriazole (148 mg, 1.08 mmol) were dissolved in N,N-dimethylformamide (2 ml) and dichloromethane (2 ml). The solution was cooled to 0° C. N-(3-Dimethylaminopropyl)-N'-ethylcarbodiimide hydrochloride (208 mg, 1.08 mmol) was added. The reaction mixture was stirred for 20 min at 0° C. A solution of 3-[2-(2-methylaminoethyl)phenoxy]propan-1-ol (227 mg, 1.08 mmol) in dichloromethane (2 ml) and ethyldiisopropyoamine (0.2 ml, 1.08 mmol) were added. The reaction mixture was stirred for 16 h, while it was warming up to room temperature. It was diluted with ethyl acetate (100 ml) and washed with a 10% aqueous solution of sodium hydrogen sulfate (100 ml). The aqueous phase was extracted with ethyl acetate (2×50 ml). The combined organic layeres were washed with a saturated aqueous solution of sodium hydrogen carbonate (100 ml) and dried over magnesium sulfate. The solvent was removed in vacuo. The crude product was purified by flash chromatography on silica (30 g), using ethyl acetate/heptane (2:1) as eluent, to give 383 mg of N-[(1R)-1-(N-{2-[2-(3-hydroxypropoxy)phenyl]ethyl}-N-methylcarbamoyl)-2-(2-naphthyl)ethyl]-N-methylcarbamic acid tert-butyl ester.

$^1$H-NMR (CDCl$_3$, selected values): d 0.98, 1.05, 1.18, and 1.26 (all s, together 9 H); 4.28, 4.98, 5.18, and 5.32 (m, m, dd, and t, together 1 H).

104

(2R)-N-(2-(2-(3-Hydroxypropoxy)phenyl)ethyl)-N-methyl-2-(methylamino)-3-(2-naphthyl)propionamide

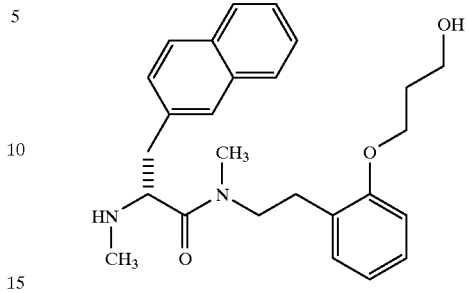

A solution of N-[(1R)-1-(N-{2-[2-(3-hydroxypropoxy)phenyl]ethyl}-N-methylcarbamoyl)-2-(2-naphthyl)ethyl]-N-methylcarbamic acid tert-butyl ester (383 mg, 0.74 mmol) in dichloromethane (4 ml) was cooled to 0° C. Trifluoroacetic acid (4 ml) was added. The reaction mixture was stirred for 105 min at 0° C. Dichloromethane (40 ml) was added. A saturated aqueous solution of sodium hydrogen carbonate (40 ml) was added dropwise. Solid sodium hydrogen carbonate was added, until pH 7 was obtained. The phases were separated. The aqueous phase was extracted with dichloromethane (3×60 ml). The combined organic layers were dried over magnesium sulfate. The solvent was removed in vacuo. The crude product was purified by flash chromatography on silica (30 g), using dichloromethane/methanol/25% aqueous ammonia (100:10:1) as eluent, to give 216 mg of (2R)-N-(2-(2-(3-hydroxypropoxy)phenyl)ethyl)-N-methyl-2-(methylamino)-3-(2-naphthyl)propionamide.

$^1$H-NMR (CDCl$_3$, selected values): d 2.00 (m, 2 H); 2.12 and 2.19 (both s, together 3 H); 2.47 and 2.91 (both s, together 3 H).

((3E)-4-N-{[1R)-1-(N-{2-[2-(3-Hydroxypropoxy)phenyl]ethyl}-N-methylcarbamoyl)-2-(2-naphthyl)ethyl]-N-methylcarbamoyl}-1,1-dimethylbut-3-enyl)carbamic acid tert-butyl ester

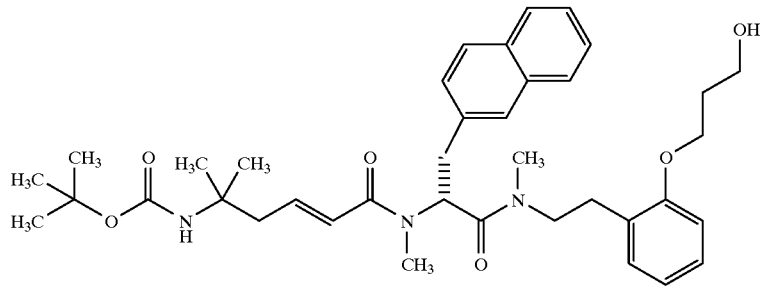

(2E)-5-(tert-butoxycarbonylamino)-5-methylhex-2-enoic acid (125 mg, 0.514 mmol) and 1-hydroxy-7- azabenzotriazole (70 mg, 0.514 mmol) were dissolved in dichloromethane (2 ml) and N,N-dimethylformamide (2 ml). The solution was cooled to 0° C. N-(3-Dimethylaminopropyl)-N'-ethylcarbodiimide hydrochloride (99 mg, 0.514 mmol) was added. The reaction mixture was stirred for 20 min at 0° C. A solution of (2R)-N-(2-(2-(3-hydroxypropoxy)phenyl)ethyl)-N-methyl-2-(methylamino)-3-(2-naphthyl)propionamide (216 mg, 0.514 mmol) in dichloromethane (2 ml) and ethyldiisopropylamine (0.09 ml, 0.514 mmol) were added. The reaction mixture was stirred for 16 h, while it was warming up to room temperature. It was diluted with ethyl acetate (70 ml) and washed with a 10% aqueous solution of sodium hydrogen sulfate solution (70 ml). The aqueous phase was extracted with ethyl acetate (2×40 ml). The combined organic layers were washed with a saturated aqueous solution of sodium hydrogen carbonate and dried over magnesium sulfate. The solvent was removed in vacuo. The crude product was purified by flash chromatography on silica (15 g), using ethyl acetate/heptane (3:1) as eluent, to give 270 mg of ((3E)-4-N-{[1R)-1-(N-{2-[2-(3-hydroxypropoxy)phenyl]ethyl}-N-methylcarbamoyl)-2-(2-naphthyl)ethyl]-N-methylcarbamoyl}-1,1-dimethylbut-3-enyl)carbamic acid tert-butyl ester.

$^1$H-NMR (CDCl$_3$, selected values): d 1.05, 1.11, 1.34, and 1.41 (all s, together 15 H); 2.82, 2.90, and 3.02 (all s, together 6 H); 5.46 and 5.83 (dd and t, together 1 H); 5.95 and 6.20 (both d, together 1 H); 6.45 (m, 1 H).

A solution of ((3E)-4-N-{[1R)-1-(N-{2-[2-(3-hydroxypropoxy)phenyl]ethyl}-N-methylcarbamoyl)-2-(2-naphthyl)ethyl]-N-methylcarbamoyl}-1,1-dimethylbut-3-enyl)carbamic acid tert-butyl ester (176 mg, 0.27 mmol) in dichloromethane (2 ml) was cooled to 0° C. Trifluoroacetic acid (2 ml) was added. The reaction mixture was stirred at 0° C. for 35 min. Dichloromethane (20 ml) was added. A saturated solution of sodium hydrogen carbonate (30 ml) was added dropwise. Solid sodium hydrogen carbonate was added, until pH 7 was obtained. The phases were separated. The aqueous phase was extracted with dichloromethane (3×30 ml). The combined organic layers were dried over magnesium sulfate. The solvent was removed in vacuo. The crude product was purified by flash chromatography on silica, using dichloromethane/methanol/25% aqueous ammonia (100:10:1) as eluent to give 64 mg of the title compound.

$^1$H-NMR (CDCl$_3$, selected values): d 0.98, 0.99, 1.10, and 1.11 (all s, together 6 H); 2.82, 2.85, 2.91, and 3.03 (all s, together 6 H); 5.47 and 5.84 (both dd, together 1 H); 5.95 and 6.19 (both d, together 1 H); 6.55 (m, 1 H).

HPLC:

32.57 min (A1).

34.60 min (B1).

MS: 546.0 ([M+H]$^+$).

For biological testing, the title compound was transferred into its acetate salt by lyophilization with 0.5M actic acid (40 ml).

Example 19

1-((2R)-2-(N-((2E)-5-Amino-5-methylhex-2-enoyl)-N-methyl amino)-3-(2-naphthyl)propionyl-2-benzyl-4-ethylsemi-carbazide

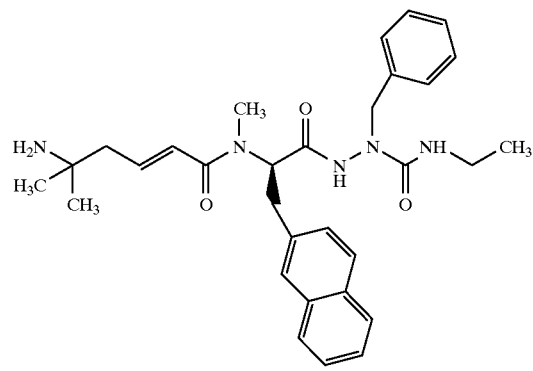

N'-Benzylidenehydrazinecarboxylic acid tert-butyl ester:

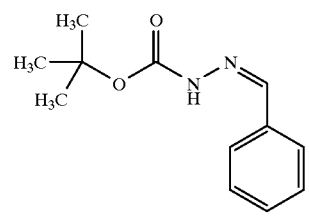

To a solution of t-butyl carbazate (2.0 g, 15.1 mmol) in 99% ethanol (20 ml) was added benzaldehyde (1.6 g, 15.1 mmol) and the mixture was stirred for 30 min. Then the mixture was cooled to 0° C. and the precipitate was separated and washed with cold ethanol and dried in vacuo to give 2.7 g (81%) of N'-benzylidenehydrazinecarboxylic acid tert-butyl ester.

$^1$H-NMR (CDCl$_3$): d 1.5 (s, 9H) 7.35 (m, 3H) 7.65 (m, 2H) 7.85 (s, 1H) 8.0 (s, 1 H)

N'-Benzylhydrazinecarboxylic acid tert-butyl ester:

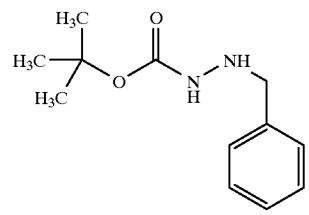

To a solution of N'-benzylidenehydrazinecarboxylic acid tert-butyl ester (2.7 g, 12.3 mmol) in tetrahydrofuran (100 ml) was added 10% palladium on carbon (0.3 g) and the mixture was hydrogenated with 280 ml of hydrogen for 40 min at atmospheric pressure. The mixture was filtered through a plug of celite and the filtrate was concentrated in vacuo to give 2.63 g of N'-benzylhydrazinecarboxylic acid tert-butyl ester.

¹H-NMR (CDCl₃): d 1.5 (s, 9H) 4.0 (s, 2H) 4.2 (b, 1H) 6.1 (b, 1H) 7.2–7.4 (m, 5H).

2-Benzyl-1-tert-butoxycarbonyl-4-ethylsemicarbazide:

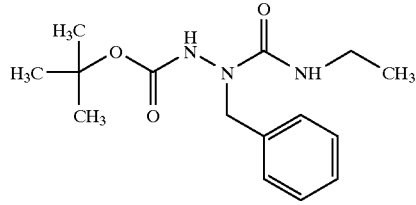

To a solution of N'-benzylhydrazinecarboxylic acid tert-butyl ester (2.5 g, 11.8 mmol) in 99% ethanol (40 ml) was added ethyl isocyanate (1.1 g, 15.2 mmol) and the mixture was stirred for 2 h. Then the mixture was concentrated in vacuo and chromatographed on silica (20 g) with petrol ether/ethyl acetate 3:2 to give 3.0 g of 2-benzyl-1-tert-butoxycarbonyl-4-ethylsemicarbazide.

¹H-NMR (CDCl₃): d 1.1 (t, 3H) 1.45 (s, 9H) 3.3 (m, 2H) 3.9–5.0 (b, 2H) 5.35 (t, 1H) 5.9 (s, 1H) 7.2–7.4 (m, 5H).

¹³C-NMR (CDCl₃): 15.0 (—CH₂$\underline{C}$H₃), 27.6 (—C($\underline{C}$H₃)₃) 34.9 (—$\underline{C}$H₂CH₃) 50.0 (—$\underline{C}$(CH₃)₃) 81.7 (—$\underline{C}$H₂—C₆H₅) 127.3–128.6 (—C₂—$\underline{C}$H₆H₅) 135.9 (—CH₂—$\underline{C}$₆H₅) 154.0 (—O$\underline{C}$ON) 157.1 (—N$\underline{C}$ON).

2-Benzyl-4-ethylsemicarbazide:

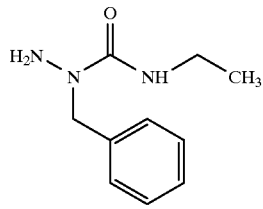

A solution of of 2-benzyl-1-tert-butoxycarbonyl-4-ethylsemicarbazide (2.8 g, 9.6 mmol) in 50% trifluoroacetic acid in dichloromethane (10 ml) was stirred for 10 min at room temperature. Then saturated sodium bicarbonate was added until pH >7 and the aqueous layer was extracted with dichloromethane (2×10 ml) and the combined organic layers were dried (magnesium sulfate) and concentrated in vacuo. The obtained oil was chromatographed on silica (100 g) with ethyl acetate as eluent to give 1.7 g of 2-benzyl-4-ethylsemicarbazide.

¹H-NMR (CDCl₃): d 1.15 (t, 3H) 3.3 (m, 2H) 4.7 (s, 2H) 7.2–7.4 (m, 5H).

2-Benzyl-1-[(2R)-2-(N-(tert-butoxycarbonyl)-N-methylamino)-3-(2-naphthyl)propionyl]-4-ethylsemicarbazide:

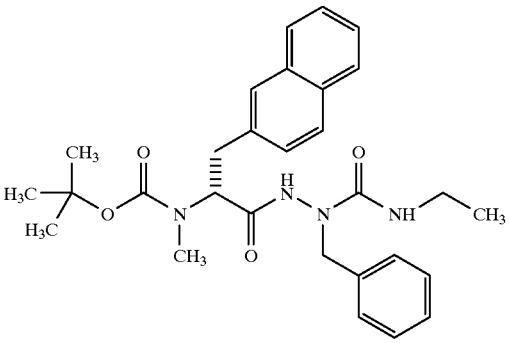

To a solution of (2R)-2-(N-tert-butoxycarbonyl-N-methylamino)-3-(2-naphthyl)propionic acid (2.6 g, 7.9 mmol) in dichloromethane (20 ml) was added 1-hydroxy-7-azabenzotriazole (1.1 g, 8.0 mmol) and 1-ethyl-3-dimethylaminopropyl carbodiimide hydrochloride (1.6 g, 8.6 mmol) and the mixture was stirred at 30 min at room temperature. Then 2-benzyl-4-ethylsemicarbazide (1.3 g, 6.6 mmol) and diisopropylethylamine (1.5 ml, 8.6 mmol) in dichloromethane (20 ml) were added and the mixture was stirred overnight. The mixture was washed with saturated sodium bicarbonate (2×50 ml), dried (magnesium sulfate) and concentrated in vacuo. The obtained product was chromatographed on silica (100 g) with petrol ether/ethyl acetate 1:1 to give 3.0 g (90%) of 2-benzyl-1-[(2R)-2-(N-(tert-butoxycarbonyl)-N-methylamino)-3-(2-naphtyl)propionyl]-4-ethylsemicarbazide.

¹H-NMR (CDCl₃): d 0.9 (t, 3H) 1.45 (s, 9H) 2.65 (s, 3H) 3.1 (m, 2H) 3.2 (m, 1H) 3.3 (dd, 2H) 4.4 (b, 2H) 4.9 (b, 1H) 5.2 (b, 1H) 6.9–7.8 (m, 12H).

2-Benzyl-1-[(2R)-2-N-methylamino-3-(2-naphthyl)propionyl]-4-ethylsemicarbazide:

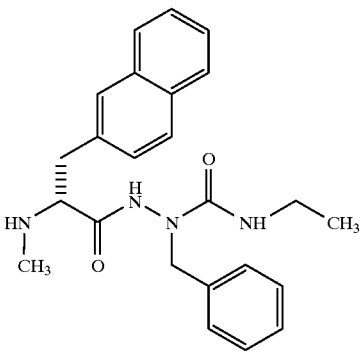

To a solution of of 2-benzyl-1-[(2R)-2-(N-(tert-butoxycarbonyl)-N-methylamino)-3-(2-naphthyl)propionyl]-4-ethylsemicarbazide (2.9 g, 5.7 mmol) in dichloromethane (15 ml) at 0° C. was added trifluoroacetic acid (5 ml) and the mixture was allowed to stir for 3 h at 0° C. Then sodium bicarbonate was added until pH >7 and the aqueous layer was extracted with dichloromethane (3×25 ml) and the combined organic layers were dried (magnesium sulfate) and concentrated to 2.0 g of 2-benzyl-1-[(2R)-2-N-methylamino-3-(2-naphthyl)propionyl]-4-ethylsemicarbazide.

¹H-NMR (CDCl₃): d 0.9 (t, 3H) 2.1 (s, 3H) 3.0 (m, 2H) 3.3 (dd, 2H) 4.6 (t, 1H) 4.7 (dd, 2H) 7.1–7.8 (m, 12H) 8.3 (s, 1H).

2-Benzyl-1-((2R)-2-(N-((2E)-5-(N-tert-butoxycarbonyl) amino-5-methylhex-2-enoyl)-N-methylamino)-3-(2-naphthyl)propionyl)-4-ethylsemicarbazide:

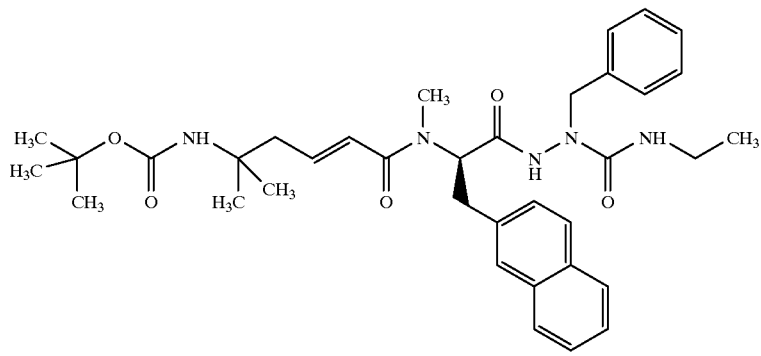

To a solution of (2E)-5-(tert-butoxycarbonylamino)-5-methylhex-2-enoic acid (0.5 g, 2.1 mmol) in dichloromethane (20 ml) were added 1-hydroxy-7-azabenzotriazole (336 mg, 2.5 mmol) and 1-ethyl-3-dimethylaminopropylcarbodiimide hydrochloride (5.5 g, 2.9 mmol) and the mixture was stirred at 30 min at room temperature. Then 2-benzyl- 1-[(2R)-2-N-methylamino-3-(2-naphthyl)propionyl]-4-ethylsemicarbazide (0.5 g, 1.2 mmol) and diisopropylethylamine (0.4 ml, 2.3 mmol) in dichloromethane (20 ml) were added and the mixture was stirred overnight. The mixture was washed with saturated sodium bicarbonate (2×20 ml), dried (magnesium sulfate) and concentrated in vacuo. The obtained product was chromatographed on silica (20 g) with petrol ether/ethyl acetate 1:1 to give 0.68 g of 2-benzyl-1-((2R)-2-(N-((2E)-5-(N-tert-butoxycarbonyl)amino-5-methylhex-2-enoyl)-N-methylamino)-3-(2-naphthyl)propionyl)-4-ethylsemicarbazide.

$^{1}$H-NMR (CDCl$_3$): d 0.9 (t, 3H) 1.25 (s, 6H) 1.4 (s, 9H) 2.65 (d, 2H) 2.9 (s, 3H) 3.0 (m, 2H) 3.1 (m, 1H) 3.5 (m, 1H) 4.4 (s, 1H) 4.7 (b, 1H) 5.4 (b, 1H) 5.1 (b, 1H) 6.1 (d, 1H) 6.8 (m, 1H) 6.9–7.8 (m, 12H).

To a solution of 2-benzyl-1-((2R)-2-(N-((2E)-5-(N-tert-butoxycarbonyl)amino-5-methylhex-2-enoyl)-N-methylamino)-3-(2-naphthyl)propionyl)-4-ethylsemicarbazide (0.66 g, 1.0 mmol) in dichloromethane (5 ml) was added trifluoroacetic acid (2.5 ml) at 0° C. and stirred for 2 h. Then sodium bicarbonate was added until pH >7 and the aqueous layer was extracted with dichloromethane (2×10 ml) and the combined organic layers were dried (magnesium sulfate) and concentrated in vacuo. The obtained product was dissolved in water (20 ml) and 1N acetic acid (2 ml) and the mixture was lyophilized to 0.5 g of the acetate salt of the title compound.

HPLC (A1): R$_t$=31.3 min (B1): R$_t$=33.0 min

LC-MS: 530.2 (M+H)$^+$ $^{1}$H-NMR (DMSO) (selected peaks): d 0.9 (t, 3H) 1.1 (s, 6H) 2.7 (s, 3H) 6.25 (d, 1H) 6.6 (m, 1H) 7.2–7.9 (m, 12H).

Example 20

1-((2S)-2-(N-(2-(((2R)-pyrrolidin-2-yl)methoxy)acetyl)-N-methylamino)-3-(2-naphthyl)propionyl-2-benzyl-4-ethyl semicarbazide

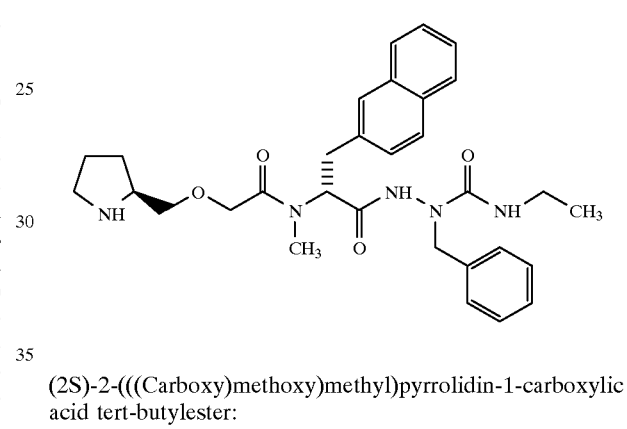

(2S)-2-(((Carboxy)methoxy)methyl)pyrrolidin-1-carboxylic acid tert-butylester:

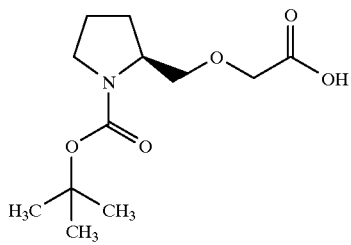

To a solution of N-t-butyloxycarbonyl-(S)-prolinol (5.0 g, 25 mmol) in 1,2-dichloroethane (500 ml) rhodium(II)acetate (180 mg) was added and the mixture was heated to 80° C. Ethyldiazoacetate (3.9 ml, 37 mmol) in 1,2-dichloroethane (180 ml) was added over a period of 90 min and the mixture was heated at 80° C. for 3 hours. Then another portion of ethyl diazoacetate (1.3 ml, 12 mmol) in 1,2-dichloroethane (40 ml) was added and the mixture was refluxed for 6 hours. The mixture was cooled to room temperature and washed with saturated sodium bicarbonate (2×100 ml) and brine (100 ml), dried (magnesium sulfate) and concentrated in vacuo. The crude product was chromatographed on silica (300 g) with petrol ether/ethyl acetate 4:1 as eluent to give 4.7 g of (2S)-2-(((ethoxycarbonyl)methoxy)methyl) pyrrolidin-1-carboxylic acid tert-butylester. The obtained product was dissolved in 1M lithium hydroxide in water/methanol 1:3 (50 ml) and stirred at room temperature overnight. The mixture was concentrated in vacuo, water (20 mL) was added and washed with ether (20 mL). The aqueous phase was acidified to pH 4 with 1M aqueous hydrogen chloride, extracted with ethyl acetate (2×100 ml) and the combined organic layers were dried (magnesium sulfate) and concentrated in vacuo to give 3.6 g of (2S)-2-(((carboxy)methoxy)methyl)-pyrrolidin-1-carboxylic acid tert-butyl ester.

1H-NMR (CDCl₃): d 1.45 (2, 9H) 1.90 (m, 4H) 3.55 (t, 2H) 3.60 (m, 3H) 4.10 (s, 2H) 10.6 (s, 1H).

To a solution of (2S)-2-(((carboxy)methoxy)methyl)-pyrrolidin-1-carboxylic acid tert-butylester (0.97 g, 3.7 mmol) in dichloromethane (15 ml) were added 1-hydroxy-7-azabenzotriazole (0.51 g, 3.7 mmol) and 1-ethyl-3-dimethylaminopropylcarbodiimide hydrochloride (0.79 g, 4.1 mmol) and the mixture was stirred at 30 min at room temperature. Then 2-benzyl-1-[(2R)-2-methylamino-3-(2-naphthyl)propionyl]-4-ethylsemicarbazide (0.75 g, 1.9 mmol) and diisopropylethylamine (0.42 ml, 2.4 mmol) in dichloromethane (15 ml) were added and the mixture was stirred overnight. The mixture was washed with saturated sodium bicarbonate (2×20 ml), dried (magnesium sulfate) and concentrated in vacuo. The obtained product was chromatographed on silica (20 g) with petrol ether/ethyl acetate 1:1. The chromatographed product was dissolved in dichloromethane (10 ml) and trifluoroacetic acid (2.5 ml) was added at 0° C. and stirred for 2 h. Then sodium bicarbonate was added until pH >7 and the aqueous layer was extracted with dichloromethane (2×10 ml) and the combined organic layers were dried (magnesium sulfate) and concentrated in vacuo. The obtained product was dissolved in water (20 ml) and 1N acetic acid (2 ml) and the mixture was lyophilized to 0.88 g of the acetate salt of the title compound.

HPLC (A1): R$_t$=31.1

(B1): R$_t$=32.6

LC-MS: 546.0 (M+H)⁺

Example 21

1-((2R)-2-(N-((2-Amino-2-methylpropoxy)acetyl)-N-methylamino)-3-(2-naphthyl)propionyl)-2-benzyl-4-ethylsemicarbazide

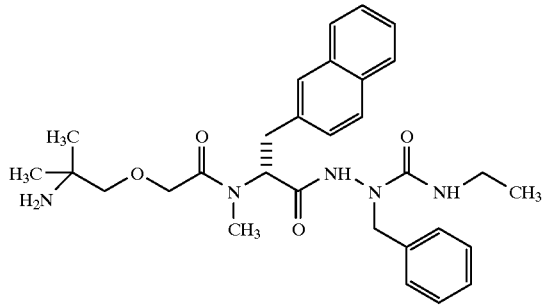

(2-t-Butoxycarbonylamino-2-methylpropoxy)acetic acid:

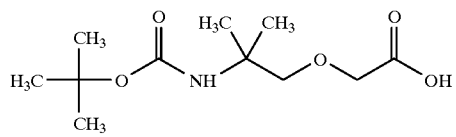

A solution of 2-t-butoxycarbonylamino-2-methylpropanol (5.0 g, 26.46 mmol) and rhodium(II)acetate (90 mg) in dichloroethane (500 ml) was heated to 80° C. Then ethyl diazoacetate (4.0 g, 34.78 mmol) was added over a period of 1 h and the mixture was stirred at reflux for 3 h. Another portion of rhodium(II)acetate (90 mg) was added and the mixture was refluxed for another 5 h. The mixture was cooled overnight and saturated sodium bicarbonate (500 ml) was added, the layers were separated and the organic layer was washed twice with saturated sodium bicarbonate (2×200 ml) and dried (magnesium sulfate) and concentrated in vacuo. The obtained product was dissolved in 1M lithium hydroxide in methanol/water 3:1 (200 ml) and stirred overnight. The solvent was removed in vacuo to a minimum, water (50 ml) was added (pH >9) and the mixture was washed with ether (100 ml). Then 1M hydrochloric acid was added until pH <4 and the mixture was extracted with ethyl acetate (100 ml) and the combined organic layers were dried (magnesium sulfate) and concentrated in vacuo to give 2.5 g of (2-t-butoxycarbonylamino-2-methylpropoxy) acetic acid.

H1-NMR (CDCl₃): d 1.3 (s, 6H) 1.45 (s, 9H) 3.5 (s, 2H) 4.15 (s, 2H) 9.9 (b, 1H).

To a solution of (2-t-butoxycarbonylamino-2-methylpropoxy) acetic acid (0.93 g, 3.7 mmol) in dichloromethane (15 ml) were added 1-hydroxy-7-azabenzotriazole (0.51 g, 3.7 mmol) and 1-ethyl-3-dimethylaminopropylcarbodiimide hydrochloride (0.79 g, 4.1 mmol) and the mixture was stirred at 30 min at room temperature. Then 2-benzyl-1-[(2R)-2-N-methylamino-3-(2-naphthyl)propionyl]-4-ethylsemicarbazide (0.75 g, 1.9 mmol) and diisopropylethylamine (0.42 ml, 2.4 mmol) in dichloromethane (15 ml) were added and the mixture was stirred overnight. The mixture was washed with saturated sodium bicarbonate (2×20 ml), dried (magnesium sulfate) and concentrated in vacuo. The obtained product was chromatographed on silica (20 g) with petrol ether/ethyl acetate 1:1. The chromatographed product was dissolved in dichloromethane (10 ml) and trifluoroacetic acid (2.5 ml) was added at 0° C. and stirred for 2 h. Then sodium bicarbonate was added until pH >7 and the aqueous layer was extracted with dichloromethane (2×10 ml)and the combined organic layers were dried (magnesium sulfate) and concentrated in vacuo. The obtained product was dissolved in water (20 ml) and 1N acetic acid (2 ml) and the mixture was lyophilized to 0.98 g of the acetate salt of the title compound.

HPLC (A1): R$_t$=31.0

(B1): R$_t$=32.6

LC-MS: 534.2 (M+H)⁺

Example 22

(3R)-4-((2E)-5-Amino-5-methylhex-2-enoyl)-3-((2-naphthyl)methyl)-1-phenethylpiperazin-2-one

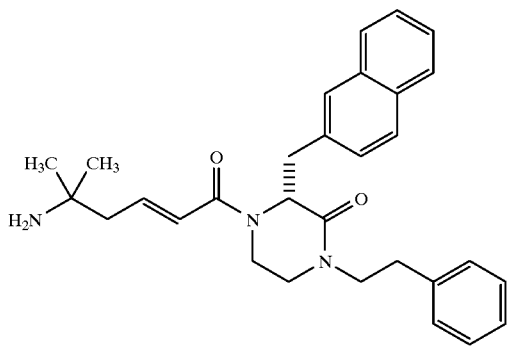

(2R)-2-((2-(tert-Butoxycarbonylamino)ethyl)amino)-3-(2-naphthyl)propionic acid methylester.

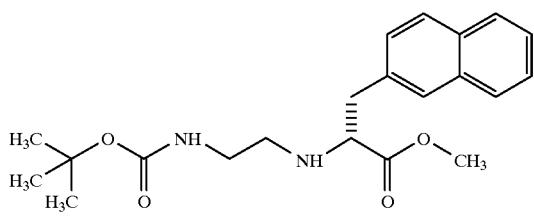

(2R)-2-Amino-3-(2-naphthyl)propionic acid (5, 0 g, 23 mmol) was added to methanol (150 ml) and thionylchloride (2.0 ml; 23 mmol) was added dropwise and the mixture was stirred overnight and then refluxed for 2.5 h. The solvent was removed in vacuo and the residue was dissolved in a mixture of methanol (95 ml) and acetic acid (5 ml). (2-Oxoethyl) carbamic acid tert-butyl ester (3.4 g, 23 mmol, prepared as in Dueholm et al. Org. Prep. Proced. Int. (1993), 457), sodium cyanoborohydride (1.9 g, 31 mmol) and molecular sieves (50 g, Fluka, 3Å) were added and the mixture was left overnight. The mixture was filtered and the filtrate was added to water (200 ml) and extracted with methylene chloride (3×100 ml). The combined organic phases were dried (magnesium sulphate), and the solvent was removed in vacuo. The residue was chromatographed on silica (3×30 cm) to afford 3.55 g of (2R)-2-((2-(tert-butoxycarbonylamino)ethyl)amino)-3-(2-naphthyl) propionic acid methylester.

$^1$H-NMR: (CDCl$_3$): d 1.39 (s, 9H); 2.56 (m, 1H); 2.75 (m, 1H); 3.09 (m, 3H); 3.59 (m, 1H); 3.65 (s, 3H); 7.28–7.81 (7 arom. H)

(3R)-3-((2-Naphthyl)methyl)piperazin-2-one.

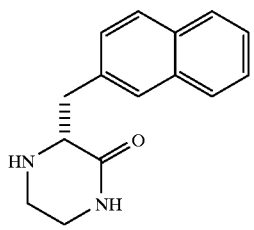

(2R)-2-((2-(tert-butoxycarbonylamino)ethyl)amino)-3-(2-naphthyl)propionic acid methylester (3.4 g, 9.1 mmol) was stirred for 1 h in a mixture of TFA (5 ml) and methylene chloride(5 ml). The volatiles were removed in vacuo and the residue was dissolved in a mixture of water (40 ml) and methanol (100 ml). Sodium hydrogencarbonate (2.3 g) was added and the mixture was stirred overnight. The solvent was removed in vacuo and the residue was dissolved in water (40 ml) and extracted with ethyl acetate (10×50 ml). The combined organic phases were dried (magnesium sulphate) and the solvent was removed in vacuo to afford 1.96 g of (3R)-3-((2-naphthyl)methyl)piperazin-2-one.

$^1$H-NMR: (CDCl$_3$; selected peaks for major rotamer): d 2.95 (m, 1H); 3.05 (m, 2H); 3.24 (m, 1H); 3.39 (m, 1H); 3.59 (dd, 1H); 3.72 (dd, 1H)

(2R)-2-(2-Naphthyl)methyl-3-oxo-4-phenethylpiperazine-1-carboxylic acid tert-butyl ester

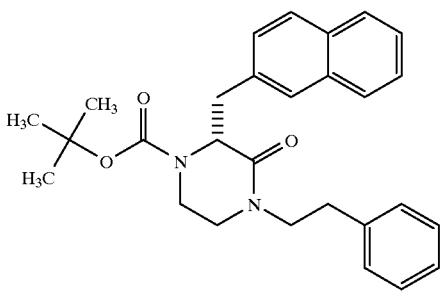

(3R)-3-((2-Naphthyl)methyl)piperazin-2-one (1.9 g; 7.9 mmol) and di-tert-butyl dicarbonate (2.1 g; 9.5 mmol) was suspended in a mixture of THF (20 ml) and aqueous sodium hydroxide (1M, 8 ml) and stirred overnight. The solvent was removed in vacuo and water (30 ml) was added. The aqueous phase was extracted with ethyl acetate (2×50 ml). The combined organic phases were dried (magnesium sulphate) and the solvent was removed in vacuo. The residue was dissolved in a mixture of DMSO (15 ml) and potassium hydroxide (1.3 g). (2-bromoethyl)benzene (2.2 g, 11 mmol) was added and the mixture was stirred for 1 h. Water (30 ml) and methylene chloride (60 ml) were added. The organic phase was washed with water (5×10 ml) and the solvent was removed in vacuo. The residue was chromatographed on silica (3×40 cm) using ethyl acetate/heptane (1:2) as eluent to afford 1.25 g of (2R)-2-(2-naphthyl)methyl-3-oxo-4-phenethylpiperazine-1-carboxylic acid tert-butyl ester.

$^1$H-NMR: (CDCl$_3$; selected peaks for major rotamer): d 1.15 (s, 9H); 2.76 (t, 2H); 3.39 (t, 3H);

(2R)-2-(2-naphthyl)methyl-3-oxo-4-phenethylpiperazine-1-carboxylic acid tert-butyl ester (1.2 g; 2.7 mmol) was dissolved in a mixture of TFA (5 ml) and methylene chloride (5 ml) and stirred for 15 min. Methylene chloride (30 ml) and aqueous sodium hydrogencarbonate (saturated) was added to pH 8. The mixture was extracted with methylene chloride (3×10 ml) and the combined aqueous phases were dried (magnesium sulphate) and the solvent was removed in vacuo. Part of the residue (400 mg 1.2 mmol) were added to a mixture of (2E)-5-(tert-butoxycarbonylamino)-5-methylhex-2-enoic acid (282 mg; 1.2 mmol); HOAt (158 mg; 1.2 mmol), EDAC (245 mg; 1.3 mmol) and DIEA (150 mg; 1.2 mmol) and stirred overnight. Methylene chloride (50 ml) was added and the mixture was washed with aqueous sodium hydrogensulphate (10%; 50 ml); aqueous sodium hydrogencarbonate (saturated; 50 ml) and water (50 ml). The organic phase was dried (magnesium sulphate) and the solvent removed in vacuo. The residue was chromatographed on silica (2×20 cm) and the residue was dissolved in a mixture of TFA (2 ml) and methylene chloride (2 ml) and stirred for 5 min. Methylene chloride and an aqueous solution of sodium hydrogenarbonate (sat.) was added to pH 8. The mixture was extracted with methylene chloride (2×10 ml). The organic phase was dried (magnesium sulphate) and the solvent was removed in vacuo to afford 310 mg of the title compound.

$^1$H-NMR: (CDCl$_3$; selected peaks for major rotamer): d 0.99 (s, 6H); 4.51 (dd, 1H); 5.61 (d, 1H); 6.56 (m, 1H)

HPLC: (method A1): R$_t$=32.47 min.

PDMS: m/z 470.5 (M+H)$^+$

We claim:

1. A compound of formula I

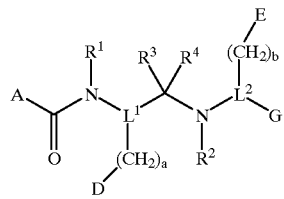
(I)

wherein

A is A$^1$ or A$^2$;

G is G$^1$ or G$^2$;

D is

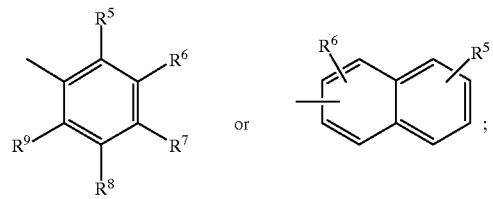
or wherein R$^5$, R$^6$, R$^7$, R$^8$, and R$^9$ independently are hydrogen, halogen, aryl, C$_{1-6}$-alkyl or C$_{1-6}$-alkoxy;

E is hydrogen, —O—(CH$_2$)$_l$—R$^{10a}$,

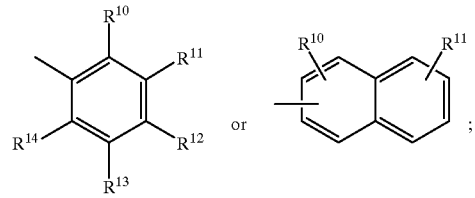
or wherein R$^{10}$, R$^{11}$, R$^{12}$, R$^{13}$ and R$^{14}$ independently are hydrogen, halogen, aryl, C$_{1-6}$-alkyl, C$_{1-6}$-alkoxy, —CONR$^{15}$R$^{16}$, —(CH$_2$)$_v$—NR$^{15}$SO$_2$R$^{17}$, —(CH$_2$)$_v$—NR$^{15}$COR$^{16}$, —(CH$_2$)$_v$—OR$^{17}$, —(CH$_2$)$_v$—OCOR$^{16}$, —(CH(R$^{15}$)R$^{16}$, —(CH$_2$)$_v$—NR$^{15}$—CS—NR$^{16}$R$^{18}$, —(CH$_2$)$_v$—NR$^{15}$—CO—NR$^{16}$R$^{18}$, R$^{15}$ and R$^{16}$ independently are hydrogen or C$_{1-6}$-alkyl optionally substituted with halogen, —N(R$^{26}$)R$^{27}$, hydroxyl, C$_{1-6}$-alkoxy, C$_{1-6}$-alkoxycarbonyl, C$_{1-6}$-alkyl-carbonyloxy or aryl, or R$^{16}$ is

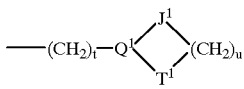

wherein

Q$^1$ is —CH<,

T$^1$ and J$^1$ are independently —CH$_2$—, —CO—, or a valence bond, t and u are independently 0, 1, 2, 3 or 4;

R$^{17}$ is C$_{1-6}$ alkyl or phenyl optionally substituted with hydroxyl or aryl;

R$^{18}$ is C$_{1-6}$ alkyl;

R$^{26}$ and R$^{27}$ are independently hydrogen or C$_{1-6}$-alkyl;

v is 0, 1, 2 or 3;

R$^{10a}$ is hydrogen, aryl optionally substituted with halogen or C$_{1-6}$-alkyl, or C$_{1-6}$-alkyl optionally substituted with halogen or C$_{1-6}$-alkyl, l is 0, 1, 2, or 3;

A$^1$ is

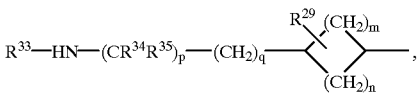

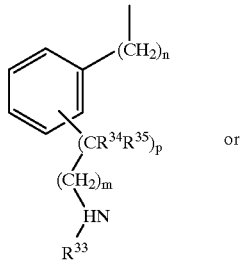
or

R$^{33}$—NH—(CR$^{34}$R$^{35}$)$_p$—(CH$_2$)$_{\overline{m}}$—M—(CHR$^{36}$)$_o$—(CH$_2$)$_{\overline{n}}$— wherein R$^{29}$, R$^{33}$, R$^{34}$, R$^{35}$ and R$^{36}$ are independently hydrogen or C$_{1-6}$ alkyl optionally substituted with halogen, amino, hydroxyl or aryl;

R$^{34}$ and R$^{35}$ may optionally form —(CH$_2$)$_i$—Z—(CH$_2$)$_j$—, wherein i and j independently are 1 or 2 and Z is a valence bond;

n, m and q are independently 0, 1, 2, or 3;

o and p are independently 0 or 1;

M is —CR$^{37}$=CR$^{38}$—, —O—, —S—, or a valence bond;

R$^{37}$ and R$^{38}$ are independently hydrogen, or C$_{1-6}$-alkyl optionally substituted with aryl;

$A^2$ is

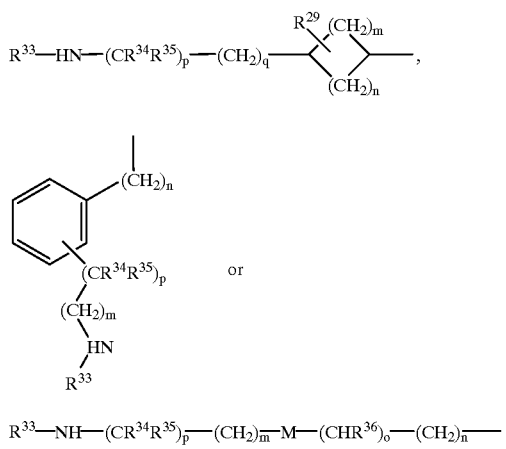

$R^{33}$—NH—$(CR^{34}R^{35})_p$—$(CH_2)_m$—M—$(CHR^{36})_o$—$(CH_2)_n$— wherein $R^{29}$, $R^{33}$, $R^{34}$, $R^{35}$ and $R^{36}$ are independently hydrogen or $C_{1-6}$-alkyl optionally substituted with halogen, amino, hydroxyl or aryl;

$R^{34}$ and $R^{35}$ may optionally form —$(CH_2)_i$—Z—$(CH_2)_j$—, wherein i and j independently are 1 or 2 and Z is a valence bond;

n, m and q are independently 0, 1, 2, or 3;

o and p are independently 0 or 1;

M is —$CR^{37}$=$CR^{38}$—, —O—, or —S—;

$R^{37}$ and $R^{38}$ are independently hydrogen, or $C_{1-6}$-alkyl optionally substituted with aryl;

$G^1$ is hydrogen, halogen, aryl, $C_{1-6}$—alkyl, $C_{1-6}$—alkoxy, —$CONR^{39}R^{40}$, —$(CH_2)_e$—$NR^{39}SO_2R^{41}$, —$(CH_2)_e$—$NR^{39}COR^{40}$, —$(CH_2)_e$—$OR^{41}$, —$(CH_2)_e$—$OCOR^{40}$, —$CH(R^{39})R^{40}$, —$CON^{39}$—$NR^{40}R^{42}$, —$(CH_2)_e$—$NR^{39}$—CS—$NR^{40}R^{42}$, —$(CH_2)_e$—$NR^{39}$—CO—$NR^{40}R^{42}$, $R^{39}$ and $R^{40}$ independently are hydrogen or $C_{1-6}$-alkyl optionally substituted with halogen, —$N(R^{50})R^{51}$, hydroxyl, $C_{1-6}$-alkoxy, $C_{1-6}$-alkoxycarbonyl, $C_{1-6}$-alkylcarbonyloxy or aryl, or $R^{40}$ is

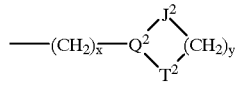

wherein $Q^2$ is —CH<, $J^2$ and $T^2$ are independently —$CH_2$—, —CO—, or a valence bond, x and y are independently 0, 1, 2, 3 or 4;

$R^{41}$ is $C_{1-6}$ alkyl substituted with aryl;

$R^{42}$ is $C_{1-6}$ alkyl;

$R^{50}$ and $R^{51}$ are independently hydrogen or $C_{1-6}$-alkyl;

e and f are independently 0, 1, 2 or 3;

$G^2$ is hydrogen or $C_{1-6}$-alkyl;

$R^1$ is hydrogen, or $C_{1-6}$-alkyl;

$R^2$ is hydrogen, —C(=O)—$R^{54}$ or $C_{1-6}$-alkyl;

$R^{54}$ is hydrgen or $C_{1-6}$-alkyl, $R^3$ and $R^4$ are taken together to form =S or =O;

$L^1$ is $CR^{57}$;

$L^2$ is $CR^{58}$ or N;

$R^{57}$ and $R^{58}$ independently are hydrogen, $C_{1-6}$-alkyl, optionally substituted with hydroxyl, halogen, $C_{1-6}$-alkoxy, or aryl;

a and b independently are 0, 1, 2, or 3;

with the proviso that:
when G is $G^2$ and $L^1$ is $CR^{57}$ and $L^2$ is $CR^{58}$, then A is $A^2$;
when G is $G^1$ and $L^1$ is $CR^{57}$ and $L^2$ is $CR^{58}$, then A is $A^1$ and $R^2$ is —C(=O)—$R^{54}$
when $L^2$ is N, then G is $G^1$ and A is $A^1$;
or a pharmaceutically acceptable salt thereof.

2. The compound according to claim 1, wherein A is
$R^{33}$—NH—$(CR^{34}R^{35})_{p(CH2)_m}$—M—$(CHR^{36})_o$—$(CH_2)_n$—
wherein $R^{33}$ is hydrogen or $C_{1-6}$ alkyl optionally substituted with hydroxyl, $R^{34}$ and $R^{35}$ are independently of each other $C_{1-6}$ alkyl, $R^{36}$ is hydrogen, M is —$CR^{37}$=$CR^{38}$—or —O—, wherein $R^{37}$ and $R^{38}$ are hydrogen or $C_{1-6}$ alkyl, p is 1, m is 1, o is 0 or 1 and n is 0 or 1.

3. The compound according to claim 1, wherein A is

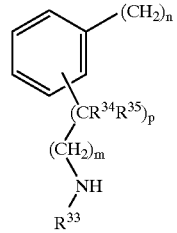

wherein $R^{33}$ is hydrogen or $C_{1-6}$ alkyl, $R^{34}$ and $R^{35}$ independently of each other are hydrogen or $C_{1-6}$ alkyl, m is 0 or 1, n is 0 or 1, and p is 0 or 1.

4. The compound according to claim 1, wherein D is

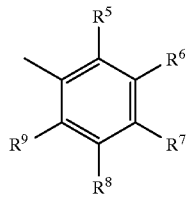

wherein $R^5$, $R^6$, $R^7$, $R^8$ and $R^9$ independently of each other are hydrogen or aryl.

5. The compound according to claim 1, wherein D is

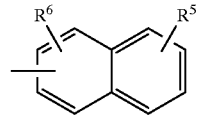

wherein $R^5$ and $R^6$ independently of each other are hydrogen or $C_{1-6}$ alkyl.

6. The compound according to claim 1, wherein E is

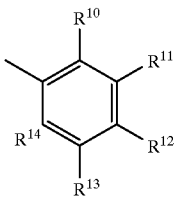

wherein $R^{10}$, $R^{11}$, $R^{12}$, $R^{13}$ and $R^{14}$ independently of each other are hydrogen, —(CH$_2$)$_v$—NR$^{15}$SO$_2$R$^{17}$, —(CH$_2$)$_v$—NR$^{15}$COR$^{16}$ or —(CH$_2$)$_v$—OR$^{17}$, wherein v is 0 or 1, $R^{15}$ is hydrogen or $C_{1-6}$ alkyl, $R^{16}$ is hydrogen or $C_{1-6}$ alkyl optionally substituted with —N(R$^{26}$)R$^{27}$, wherein $R^{26}$ and $R^{27}$ independently of each other are hydrogen or $C_{1-6}$ alkyl, $R^{17}$ is $C_{1-6}$ alkyl or phenyl optionally substituted with hydroxyl or phenyl.

7. The compound according to claim 1, wherein G is hydrogen or —CONR$^{39}$R$^{40}$, wherein $R^{39}$ and $R^{40}$ independently of each other are hydrogen or $C_{1-6}$ alkyl.

8. The compound according to claim 1, wherein $R^2$ is hydrogen, —C(=O)—R$^{54}$ or $C_{1-6}$ alkyl, wherein $R^{54}$ is $C_{1-6}$ alkyl.

9. The compound according to claim 1, wherein $R^3$ and $R^4$ are taken together to form =O.

10. The compound according to claim 1, wherein a is 1.

11. The compound according to claim 1, wherein b is 0 or 1.

12. The compound according to claim 1, wherein $L^1$ is —CH—.

13. The compound according to claim 1, wherein $L^1$ is —CH— or >N—.

14. The compound according to claim 1, selected from the group consisting of 1-((2R)-2-(N-((2E)-5-amino-5-methylhex-2-enoyl)-N-methylamino)-3-(2-naphthyl)propionyl)-2-benzyl-4-ethylsemicarbazide, 1-((2R)-2-(N-((2-amino-2-methylpropoxy)acetyl)-N-methylamino)-3-(2-naphthyl)propionyl)-2-benzyl-4-ethylsemicarbazide, (2R)-2-(N-((2E)-5-Amino-5-methylhex-2-enoyl)-N-methylamino)-3-(2-naphthyl)propionic acid N-methyl-N-phenethylamide, or the trifluoroacetate salt thereof, (2R)-2-(N-((2E)-5-Amino-5-methylhex-2-enoyl)-N-methylamino)-3-(2-naphthyl)propionic acid N-methyl-N-(2-(2-(methylsulfonylamino)phenyl)ethyl)amide, (2R)-2-(N-((2E)-5-((2R)-2-hydroxypropylamino)-5-methylhex-2-enoyl)-N-methylamino)-N-methyl-3-(2-naphthyl)-N-phenethylpropionamide, or the trifluoroacetate salt thereof, (2E)-5-Amino-5-methylhex-2-enoic acid N-((1R)-2-(N-acetyl-N-((1R)-1-(methylcarbamoyl)-2-phenylethyl) amino)-1-((2-naphthyl)methyl)ethyl)amide, (2E)-5-Amino-5-methylhex-2-enoic acid N-methyl-N-((1R)-1-(N-methyl-N-(3-phenylpropyl)carbamoyl)-2-(2-naphthyl)ethyl)amide, (2E)-5-Methyl-N-methyl-5-(methylamino)-N-((1R)-1-(N-methyl-N-phenethylcarbamoyl)-2-(2-naphthyl)ethyl)hex-2-enamide, (2R)-2-(N-((2E)-5-Amino-5-methylhex-2-enoyl)-N-methylamino)-N-(2-(2-(2-hydroxyethoxy)phenyl)ethyl)-N-methyl-3-(2-naphthyl)propionamide, (2R)-2-(N-((2E)-5-Amino-5-methylhex-2-enoyl)-N-methylamino)-N-methyl-3-(2-naphthyl)-N-(2-(2-methylsulfonylaminophenyl)ethyl)propionamide, (2E)-N-((1R)-1-(N-(2-(2-(2-Hydroxyethoxy)phenyl)ethyl)-N-methylcarbamoyl)-2-(2-naphthyl)ethyl)-N-methyl-5-methyl-5-(methylamino)hex-2-enamide, 3-Aminomethyl-N-[(1R)-1-(N-{2-[2-(2-hydroxyethoxy)phenyl]ethyl}-N-methylcarbamoyl)-2-(2-naphthyl)ethyl]benzamide, (2E)-5-Amino-5-methylhex-2-enoic acid N-((1R)-1-(N-(2-(2-(2-hydroxyethoxy)phenyl)ethyl)-N-methylcarbomoyl)-2-(2-naphthyl)ethyl)-N-methylamide, (2E)-5-Amino-5-methylhex-2-enoic acid N-((1R)-1-{N-[2-(2-(benzenesulfonylamino)phenyl)ethyl]-N-methylcarbamoyl}-2-(2-naphthyl)ethyl)-N-methylamide, 2-Amino-N-(2-(2-(N-((2R)-2-(N-((2E)-5-Amino-5-methylhex-2-enoyl)-N-methylamino)-3-(2-naphthyl)propionyl)-N-methylamino)ethyl)phenyl)acetamide, (2R)-2-(N-((2E)-5-Amino-5-methylhex-2-enoyl)-N-methylamino)-N-(2-(2-(3-hydroxypropoxy)phenyl)ethyl)-N-methyl-3-(2-naphthyl)propionamide, 3-Aminomethyl-N-[(1R)-1-(N-{2-[2-(2-hydroxyethoxy)phenyl]ethyl}-N-methylcarbamoyl)-2-(2-naphthyl)ethyl]benzamide, and (2E)-5-Amino-5-methylhex-2-enoic acid N-((1R)-1-(N-(2-(2-(2-hydroxyethoxy)phenyl)ethyl)-N-methylcarbomoyl)-2-(2-naphthyl)ethyl)amide; or a pharmaceutically acceptable salt thereof.

15. A pharmaceutical composition comprising, as an active ingredient, a compound according to claim 1 or a pharmaceutically acceptable salt thereof together with a pharmaceutically acceptable carrier or diluent.

16. A method of stimulating the release of growth hormone from the pituitary, the method comprising administering to a subject in need thereof an effective amount of a compound according to claim 1 or a pharmaceutically acceptable salt thereof.

* * * * *

UNITED STATES PATENT AND TRADEMARK OFFICE
CERTIFICATE OF CORRECTION

PATENT NO. : 5,922,770
DATED : July 13, 1999
INVENTOR(S) : Peschke et al.

It is certified that error appears in the above-identified patent and that said Letters Patent is hereby corrected as shown below:

Col. 118, line 17, Claim 2, old Claim 3, change "$(CR^{34}R^{35})_p\ (CH_2)_{(CH2)_m}$" and insert --$(CR^{34}R^{35})_p\ (CH_2)_m$--.

Col. 119, line 32, Claim 13, old Claim 22, change "$L^1$ is" and insert --$L^2$ is--.

Signed and Sealed this

Twenty-first Day of December, 1999

Attest:

Q. TODD DICKINSON

*Attesting Officer*   Acting Commissioner of Patents and Trademarks